(12) United States Patent
Raje et al.

(10) Patent No.: US 10,179,774 B2
(45) Date of Patent: *Jan. 15, 2019

(54) SYNTHESIS OF CHIRALLY PURIFIED SUBSTITUTED BENZOTHIAZOLE DIAMINES

(71) Applicant: KNOPP BIOSCIENCES LLC, Pittsburgh, PA (US)

(72) Inventors: Prasad Raje, North Syracuse, NY (US); Rajendrakumar Reddy Gadikota, North Syracuse, NY (US); Jian-Xie Chen, Manlius, NY (US); Olga V. Lapina, Clifton Park, NY (US); John M. McCall, Boca Grande, FL (US)

(73) Assignee: Knopp Biosciences LLC, Pittsburgh, PA (US)

( * ) Notice: Subject to any disclaimer, the term of this patent is extended or adjusted under 35 U.S.C. 154(b) by 55 days.

This patent is subject to a terminal disclaimer.

(21) Appl. No.: 15/369,230

(22) Filed: Dec. 5, 2016

(65) Prior Publication Data

US 2017/0158649 A1 Jun. 8, 2017

Related U.S. Application Data

(63) Continuation of application No. 13/973,987, filed on Aug. 22, 2013, now abandoned, which is a continuation of application No. 12/049,235, filed on Mar. 14, 2008, now Pat. No. 8,519,148.

(60) Provisional application No. 60/894,829, filed on Mar. 14, 2007, provisional application No. 60/894,814, filed on Mar. 14, 2007.

(51) Int. Cl.
C07D 277/82 (2006.01)

(52) U.S. Cl.
CPC .................. *C07D 277/82* (2013.01)

(58) Field of Classification Search
CPC .................................................. C07D 277/82
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran et al. |
| 4,314,557 A | 2/1982 | Chandrasekaran et al. |
| 4,327,725 A | 5/1982 | Cortese et al. |
| 4,379,454 A | 4/1983 | Campbell et al. |
| 4,395,859 A | 8/1983 | Rohrer |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,588,580 A | 5/1986 | Gale et al. |
| 4,612,008 A | 9/1986 | Wong et al. |
| 4,626,539 A | 12/1986 | Aungst et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,731,374 A | 3/1988 | Griss et al. |
| 4,781,924 A | 11/1988 | Lee et al. |
| 4,783,337 A | 11/1988 | Wong et al. |
| 4,788,062 A | 11/1988 | Gale et al. |
| 4,806,341 A | 2/1989 | Chien et al. |
| 4,816,258 A | 3/1989 | Nedberge et al. |
| 4,843,086 A | 6/1989 | Griss et al. |
| 4,849,226 A | 7/1989 | Gale |
| 4,886,812 A | 12/1989 | Griss et al. |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,024,843 A | 6/1991 | Kuczynski et al. |
| 5,069,909 A | 12/1991 | Sharma et al. |
| 5,071,656 A | 12/1991 | Lee et al. |
| 5,082,668 A | 1/1992 | Wong et al. |
| 5,091,190 A | 2/1992 | Kuczynski et al. |
| 5,112,842 A | 5/1992 | Zierenberg et al. |
| 5,122,382 A | 6/1992 | Gale et al. |
| 5,141,750 A | 8/1992 | Lee et al. |
| 5,284,660 A | 2/1994 | Lee et al. |
| 5,314,694 A | 5/1994 | Gale et al. |
| 5,342,623 A | 8/1994 | Enscore et al. |
| 5,411,740 A | 5/1995 | Lee et al. |
| 5,442,117 A | 8/1995 | Stahley et al. |
| 5,545,413 A | 8/1996 | Kuczynski et al. |

(Continued)

FOREIGN PATENT DOCUMENTS

AU 2006279643 B2 8/2006
AU 2002360600 B2 3/2008

(Continued)

OTHER PUBLICATIONS

Hardy et al. "Genetic Classification of Primary Neurodegenerative Disease" Nov. 6 1998 Science 282 '(5391)1075-1079.

(Continued)

*Primary Examiner* — Amanda L Aguirre
(74) *Attorney, Agent, or Firm* — Pepper Hamilton LLP

(57) ABSTRACT

Methods for preparing chirally purified substituted 4,5,6,7-tetrahydro-benzothiazole diamines such as, for example, (6R)2-amino-4,5,6,7-tetrahydro-6-(propylamino)benzothiazole and purifying a dominant enantiomer of substituted 4,5,6,7-tetrahydro-benzothiazole diamines from entantiomerically enriched mixtures of substituted 4,5,6,7-tetrahydro-benzothiazole diamines are provided herein.

36 Claims, 14 Drawing Sheets

(56) References Cited

U.S. PATENT DOCUMENTS

| | | |
|---|---|---|
| 5,591,454 A | 1/1997 | Kuczynski et al. |
| 5,635,203 A | 6/1997 | Gale et al. |
| 5,650,420 A | 7/1997 | Hall et al. |
| 5,674,895 A | 10/1997 | Guittard et al. |
| 5,719,060 A | 2/1998 | Hutchens et al. |
| 5,792,664 A | 8/1998 | Chait et al. |
| 5,804,215 A | 9/1998 | Cubbage et al. |
| 5,830,497 A | 11/1998 | Yamanaka et al. |
| 5,840,754 A | 11/1998 | Guittard et al. |
| 5,912,268 A | 6/1999 | Guittard et al. |
| 6,043,251 A | 3/2000 | Douillet et al. |
| 6,156,777 A | 12/2000 | Hall et al. |
| 6,187,802 B1 | 2/2001 | Cheetham et al. |
| 6,197,339 B1 | 3/2001 | Ju |
| 6,228,398 B1 | 5/2001 | Devane et al. |
| 6,255,329 B1 | 7/2001 | Maj |
| 6,262,115 B1 | 7/2001 | Guittard et al. |
| 6,284,774 B1 | 9/2001 | Wright et al. |
| 6,294,790 B1 | 9/2001 | Weinberger |
| 6,443,976 B1 | 9/2002 | Flower et al. |
| 6,458,820 B1 | 10/2002 | Hall et al. |
| 6,480,820 B1 | 11/2002 | Clopton et al. |
| 6,541,486 B1 | 4/2003 | Bitler et al. |
| 6,618,138 B2 | 9/2003 | Khoury |
| 6,667,329 B1 | 12/2003 | Maj |
| 6,675,104 B2 | 1/2004 | Paulse et al. |
| 6,727,367 B2 | 4/2004 | Pospisilik |
| 6,730,325 B2 | 5/2004 | Devane et al. |
| 6,750,235 B1 | 6/2004 | Rosenbaum |
| 6,776,984 B1 | 8/2004 | Schwartz |
| 6,793,936 B2 | 9/2004 | Devane et al. |
| 6,902,742 B2 | 6/2005 | Devane et al. |
| 6,919,092 B2 | 7/2005 | Guittard et al. |
| 6,919,373 B1 | 7/2005 | Lam et al. |
| 6,927,036 B2 | 8/2005 | Gallop et al. |
| 6,929,801 B2 | 8/2005 | Klose et al. |
| 6,930,129 B2 | 8/2005 | Lam et al. |
| 7,005,255 B2 | 2/2006 | Kaddurah-Daouk et al. |
| 7,157,480 B2 | 1/2007 | Bennett, Jr. |
| 7,344,733 B2 | 3/2008 | Beier et al. |
| 7,572,596 B2 | 8/2009 | Bowser |
| 7,741,490 B2 | 6/2010 | Castaldi et al. |
| 8,017,598 B2 | 9/2011 | Bozik et al. |
| 8,186,890 B2 | 5/2012 | Lu |
| 8,192,091 B2 | 6/2012 | Hsu et al. |
| 8,408,815 B2 | 4/2013 | Lin et al. |
| 8,519,148 B2 * | 8/2013 | Raje ............... C07D 277/82 548/161 |
| 2002/0004058 A1 | 1/2002 | Yoshii et al. |
| 2002/0103240 A1 | 8/2002 | Pospisilik |
| 2002/0106731 A1 | 8/2002 | Ruben et al. |
| 2002/0151526 A1 | 10/2002 | Gallop et al. |
| 2002/0177626 A1 | 11/2002 | Cook et al. |
| 2003/0013120 A1 | 1/2003 | Patz et al. |
| 2003/0049318 A1 | 3/2003 | Davis et al. |
| 2003/0166696 A1 | 9/2003 | Warsinksy et al. |
| 2003/0203055 A1 | 10/2003 | Rao et al. |
| 2004/0014721 A1 | 1/2004 | Hensley et al. |
| 2004/0031667 A1 | 2/2004 | Dinkel et al. |
| 2004/0033530 A1 | 2/2004 | Awrey et al. |
| 2004/0067991 A1 | 4/2004 | Greig et al. |
| 2004/0097540 A1 | 5/2004 | Peters et al. |
| 2004/0122104 A1 | 6/2004 | Hirsh et al. |
| 2004/0132788 A1 | 7/2004 | Chabrier De Lassauniere et al. |
| 2004/0132826 A1 | 7/2004 | Hirsh et al. |
| 2004/0219213 A1 | 11/2004 | Burnside et al. |
| 2004/0247656 A1 | 12/2004 | Beier et al. |
| 2004/0265370 A1 | 12/2004 | Odidi et al. |
| 2005/0031667 A1 | 2/2005 | Patel et al. |
| 2005/0032856 A1 | 2/2005 | Bennett, Jr. et al. |
| 2005/0053649 A1 | 3/2005 | Chalmers |
| 2005/0059717 A1 | 3/2005 | Van Eupen et al. |
| 2005/0070715 A1 | 3/2005 | Bhat et al. |
| 2005/0074865 A1 | 4/2005 | Afeyan et al. |
| 2005/0089575 A1 | 4/2005 | Friedl et al. |
| 2005/0148026 A1 | 7/2005 | Bowser et al. |
| 2005/0208156 A1 | 9/2005 | Ploch et al. |
| 2005/0220877 A1 | 10/2005 | Patel et al. |
| 2005/0226926 A1 | 10/2005 | Amidon et al. |
| 2005/0265379 A1 | 12/2005 | Rao |
| 2006/0009659 A1 | 1/2006 | Keil et al. |
| 2006/0046967 A1 | 3/2006 | Satyam |
| 2006/0051419 A1 | 3/2006 | Friedl et al. |
| 2006/0069263 A1 | 3/2006 | Gribun et al. |
| 2006/0099257 A1 | 5/2006 | Langridge et al. |
| 2006/0106224 A1 | 5/2006 | Gupta et al. |
| 2006/0110450 A1 | 5/2006 | Eisenreich |
| 2006/0121619 A1 | 6/2006 | Bowser |
| 2006/0128643 A1 | 6/2006 | Kaddurah-Daouk et al. |
| 2006/0141037 A1 | 6/2006 | Mehta et al. |
| 2006/0148866 A1 | 7/2006 | Xia et al. |
| 2006/0281797 A1 | 12/2006 | Bennett, Jr. |
| 2006/0286167 A1 | 12/2006 | Staunton et al. |
| 2007/0087410 A1 | 4/2007 | Lanahan et al. |
| 2007/0105918 A1 | 5/2007 | Bennett, Jr. |
| 2007/0203209 A1 | 8/2007 | Bartolini et al. |
| 2007/0259930 A1 * | 11/2007 | Bozik ............... A61K 9/0048 514/367 |
| 2008/0014259 A1 | 1/2008 | Bozik et al. |
| 2008/0020028 A1 | 1/2008 | Shevchuk et al. |
| 2008/0026043 A1 | 1/2008 | Mueller et al. |
| 2008/0081041 A1 | 4/2008 | Nemeth |
| 2008/0096939 A1 | 4/2008 | Keil et al. |
| 2008/0194832 A1 | 8/2008 | Silva Guisasola et al. |
| 2008/0227985 A1 | 9/2008 | Raje et al. |
| 2008/0234338 A1 | 9/2008 | Bennett, Jr. |
| 2009/0042956 A1 | 2/2009 | Bozik et al. |
| 2009/0054504 A1 | 2/2009 | Bozik et al. |
| 2009/0105483 A1 | 4/2009 | Balicki et al. |
| 2009/0149518 A1 | 6/2009 | Nishii et al. |
| 2010/0291073 A1 | 11/2010 | Koiki et al. |
| 2010/0292149 A1 | 11/2010 | Bowser |
| 2011/0009460 A1 | 1/2011 | Gribkoff et al. |
| 2011/0020339 A1 | 1/2011 | Hargreave et al. |
| 2011/0190356 A1 | 8/2011 | Bozik et al. |
| 2011/0218222 A1 | 9/2011 | Bennett, Jr. |
| 2011/0224268 A1 | 9/2011 | Bozik et al. |
| 2011/0293718 A1 | 12/2011 | Bozik et al. |
| 2011/0301210 A1 | 12/2011 | Bennett, Jr. |
| 2012/0134929 A1 | 5/2012 | McGrath et al. |
| 2012/0142715 A1 | 6/2012 | Kim |
| 2012/0148575 A1 | 6/2012 | Koike et al. |
| 2012/0225915 A1 | 9/2012 | Bozik et al. |
| 2012/0253047 A1 | 10/2012 | Allegrini et al. |
| 2012/0258994 A1 | 10/2012 | McKinney et al. |
| 2013/0059801 A1 | 3/2013 | Milne et al. |
| 2013/0079526 A1 | 3/2013 | Greenfield et al. |
| 2013/0116292 A1 | 5/2013 | Bennett, Jr. |
| 2013/0123312 A1 | 5/2013 | Bozik et al. |
| 2013/0172394 A1 | 7/2013 | Bennett, Jr. |
| 2013/0230569 A1 | 9/2013 | Bozik et al. |
| 2013/0245081 A1 | 9/2013 | Gribkoff et al. |
| 2013/0273557 A1 | 10/2013 | Gribkoff et al. |
| 2013/0310430 A1 | 11/2013 | Bozik et al. |
| 2014/0018343 A1 | 1/2014 | Romero et al. |
| 2014/0031401 A1 | 1/2014 | Bozik et al. |
| 2014/0100372 A1 | 4/2014 | Raje et al. |
| 2014/0329869 A1 | 11/2014 | Bozik et al. |
| 2015/0018397 A1 | 1/2015 | Bozik et al. |
| 2015/0126745 A1 | 5/2015 | Chen et al. |
| 2016/0022647 A1 | 1/2016 | Bozik et al. |
| 2016/0030397 A1 | 2/2016 | Bozik et al. |
| 2016/0158205 A1 | 6/2016 | Bozik et al. |
| 2016/0193186 A1 | 7/2016 | Bozik et al. |
| 2016/0193187 A1 | 7/2016 | Bozik et al. |

FOREIGN PATENT DOCUMENTS

| | | |
|---|---|---|
| AU | 2007333050 B2 | 12/2013 |
| CA | 2619217 A1 | 2/2007 |
| CA | 2605078 A1 | 1/2013 |
| CN | 1308533 A | 8/2001 |
| CN | 1617720 A | 5/2005 |

(56) References Cited

FOREIGN PATENT DOCUMENTS

| | | |
|---|---|---|
| CN | 1735604 A | 2/2006 |
| CN | 101677564 A | 3/2010 |
| CN | 102160865 A | 8/2011 |
| CN | 102772404 A | 11/2012 |
| EP | 0186087 A1 | 7/1986 |
| EP | 0558861 A1 | 9/1993 |
| EP | 2156833 A1 | 2/2010 |
| EP | 1453505 B1 | 9/2010 |
| EP | 2305252 A1 | 4/2011 |
| EP | 2442655 | 4/2012 |
| EP | 2465500 A | 6/2012 |
| EP | 2497472 A1 | 9/2012 |
| EP | 2497473 A1 | 9/2012 |
| EP | 2497474 A1 | 9/2012 |
| EP | 2542541 A | 1/2013 |
| EP | 2246053 B1 | 9/2013 |
| JP | 61-155377 | 7/1986 |
| JP | H07504655 A | 5/1995 |
| JP | 10-510809 A | 10/1998 |
| JP | 2006-143708 | 6/2006 |
| JP | 2009-504748 A | 2/2009 |
| JP | 2010-031059 A | 2/2010 |
| JP | 2010-513316 A | 4/2010 |
| JP | 4500543 | 4/2010 |
| JP | 11-515012 A | 5/2011 |
| RU | 2009 126742 A | 1/2011 |
| WO | WO 1993/17683 A1 | 9/1993 |
| WO | WO 1993/24834 A1 | 12/1993 |
| WO | WO 1996/18395 A | 6/1996 |
| WO | WO 1997/15304 A1 | 5/1997 |
| WO | WO 1998/59360 A1 | 12/1998 |
| WO | WO 2001/13902 A2 | 3/2001 |
| WO | WO 2001/22820 A1 | 4/2001 |
| WO | WO 2001/62249 A1 | 8/2001 |
| WO | WO 2003/049705 A2 | 6/2003 |
| WO | WO 03/070188 A2 | 8/2003 |
| WO | WO 2004/002520 A1 | 1/2004 |
| WO | WO 2004/010999 A1 | 2/2004 |
| WO | WO 2004/026246 A2 | 4/2004 |
| WO | WO 2004/041797 A1 | 5/2004 |
| WO | WO 2004/050034 A2 | 6/2004 |
| WO | WO 2004/058163 A2 | 7/2004 |
| WO | WO 2005/011687 A1 | 2/2005 |
| WO | WO 2005/092871 A2 | 10/2005 |
| WO | WO 2005/123193 A2 | 12/2005 |
| WO | WO 2006/003471 A2 | 1/2006 |
| WO | WO 2006/012277 A | 2/2006 |
| WO | WO 2006/015943 A2 | 2/2006 |
| WO | WO 2006/015944 A2 | 2/2006 |
| WO | WO 2006/43532 A1 | 4/2006 |
| WO | WO 2006/076681 A2 | 7/2006 |
| WO | WO 2006/116369 A2 | 11/2006 |
| WO | WO 2007/022182 A1 | 2/2007 |
| WO | WO 2007/045620 A | 4/2007 |
| WO | WO 2007/075095 A1 | 7/2007 |
| WO | WO 2007/076062 A2 | 7/2007 |
| WO | WO 2007/090882 A2 | 8/2007 |
| WO | WO 2007/121188 A | 10/2007 |
| WO | WO 2007/137071 A2 | 11/2007 |
| WO | WO 2008/023027 A2 | 2/2008 |
| WO | WO 2008/041240 A1 | 4/2008 |
| WO | WO 2008/52953 A1 | 5/2008 |
| WO | WO 2008/074033 A1 | 6/2008 |
| WO | WO 2008/104847 A2 | 9/2008 |
| WO | WO 2008/113003 A1 | 9/2008 |
| WO | WO 2008/113056 A2 | 9/2008 |
| WO | WO 2010/022140 A1 | 2/2010 |
| WO | WO 2010/148409 A1 | 12/2010 |
| WO | WO 2011/109596 A1 | 9/2011 |
| WO | WO 2011/150221 A2 | 12/2011 |
| WO | WO 2012/019015 A2 | 2/2012 |
| WO | 2013034550 A1 | 3/2013 |
| WO | WO 2013/096816 A1 | 6/2013 |
| WO | WO 2013/096870 A1 | 6/2013 |
| WO | WO 2014/134569 A1 | 9/2014 |
| WO | WO 2015/006708 A1 | 1/2015 |
| WO | WO 2015/0018397 A1 | 1/2015 |
| WO | WO 2015/023786 A1 | 2/2015 |
| WO | WO 2015/023790 A1 | 2/2015 |

OTHER PUBLICATIONS

Hasegawa et al. "A New Process for Synthesis of the Astrcyte Activation Suppressor ONO-2506" 2005 Organic Proc. Res. & Dev. 9:774-781.

Khan et al. "Alzheimer's disease cybrids replicate beta-amyloid abnormalities through cell death pathways" Aug. 2000 Ann Neurol. 48(2):148-55. PubMed PMID: 10939564.

Kieburtz "Safety and Efficacy of Pramipexole in Early Parkinson Disease" 1997 JAMA 278(2):125-130.

Lucchinetti et al. "Inflammatory Cortical Demyelination in Early Multiple Sclerosis" The New England Journal of Medicine (2011) (365) pp. 2188-2197.

Roca-Santiago et al. "Alzheimer's Disease and Age-related Macular Degeneration" Feb. 2006 Arch. Soc. Esp. Oftalmol. 81(2):73-78.

Rothstein et al. "β-Lactam antibiotics offer neuroprotection by increasing glutamate transporter expression" Jan. 6, 2005 Nature 433(7021):73-77.

Liou et al. ("Case Report Churg-Strauss syndrome presented as multiple intracerebral hemorrhage." Lupus (1997);6:279-282).

Abrahamson et al. "Structure and expression of the human cystatin C gene" 1990, Biochem J. 268(2):287-294.

Abramova et al. "Inhibition by R(+) or S(−) Pramipexole of Caspase Activation and Cell Death Induced by Methylpyridinium Ion or Beta Amyloid Peptide in SH-SY5Y Neuroblastoma" 2002, J. Neuroscience Res. 67(4):494-500.

Agardh et al. "Expression of antioxidant enzymes in rat retinal ischemia followed by reperfusion" Jul. 2006, Metabolism 55(7):892-898 (Abstract).

Aguila et al. "Prognosis in Amyotrophic Lateral Sclerosis: A population based study" 2003, Neurology 60:813-819.

Akintola-Ogunremi et al., "Chronic lymphocytic leukemia presenting with symptomatic centeral nervous system involvement," Ann. Hematol. (2002), (81) pp. 402-404.

Anonymous "Variant of Parkinson's Drug Tested in ALS" Jul. 19, 2006 (printed from www.als-mda.org/research/news/060719als_pramipexole.html on Feb. 21, 2008) (Abstract).

Anosova et al. "Antigenecity and Immunogenicity of Allogeneic Retinal Transplants" Oct. 2001, J. Clin. Invest. 108(8):1175-1183.

Ansel et al. "Pharmaceutical Dosage Forms and Drug Delivery Systems, 6$^{th}$ ed." 1995, Williams and Wilkins Media, Malvern, PA (TOC).

Anthony et al. (Nat Rev Immunol Dec. 2007; 7(12):975-987.

Arico et al., Restless Legs Syndrome as the Presenting Symptom of Multiple Myeloma, Journal of Clinical Sleep Medicine (2013), 9(4) pp. 383-385.

Asgeirsson et al. "Hereditary cystatin C amyloid angiopathy: monitoring the presence of the Leu-68→Gln cystatin C variant in cerebrospinal fluids and monocyte cultures by MS" 1998, Biochem. J, 329 (Pt 3):497-503 (1998).

Ashcroft et al. "An Efficient and Scalable Synthesis of the Endothelin Antagonists UK-350,926 and UK-349,862 Using a Dynamic Resolution Process" 2005, Organic Proc. Res. & Dev. 9:663-669.

Balicki et al. "A New, Efficient and Economic Method for Preparation of Pramipexole" May 16, 2006, Book of Abstracts: The Fifth Multidisciplinary conference on Drug Research, Pielaszek Research (Warszawa, Poland) Poster No. 1-19, p. 30 (English Abstract).

Balicki et al. "New method for preparing pramipexole dihydrochloride monohydrate" 2006, Przemysl Chemiczny 85(5):344-346.

Banker et al. "Modern Pharmaceutics" 1979, Marcel Dekker, Inc. (TOC).

Beal "Oxidative Metabolism" 2000, Ann. N.Y. Acad. Sci. 924:164-169.

Beatty et al. "The Role of Oxidative Stress in the Pathogenesis of Age-Related Macular Degeneration" 2000, Surv. Opthalmol 45(2):115-134.

(56) References Cited

OTHER PUBLICATIONS

Benson et al. "Identification of carriers of a variant plasma prealbumin (transthyretin) associated with familial amyloidotic polyneuropathy type J" 1985, J. Clin. Invest. 74:71-75.
Berge et al. "Pharmaceutical Salts" 1977, J. Pharm. Sciences 66(1):1-19.
Bergen et al. "Identification of transthyretin variants by sequential proteomic and genomic analysis" 2004, Clin. Chem. 50(9):1544-1552.
Bernstein et al. "Transythyretin: Its response to malnutrition and stress injury. Clinical usefulness and economic implications" Dec. 2002, Clin. Chem. Lab. Med. 40(12):1344-1348.
Biglan et al. "A Review of Pramipexole and its Clinical Utility in Parkinson's Disease" 2002, Expert Opinion Pharmacotherapy 3(2):197-210.
Borchelt et al. "Superoxide dismutase 1 with mutations linked to familial amyotrophic lateral sclerosis possesses significant activity" 1994, PNAS USA 91(17):8292-8296.
Bozik et al. "Safety, Tolerability, and Pharmacokinetics of KNS-760704 (Dexpramipexole) in Healthy Adult Subjects" 2011, J. Clin. Pharmacol. 51:1177-1185.
Carvey, et al. "Attenuation of levodopa-induced toxicity in mesencephalic cultures by pramipexole" 1997, J. Neural. Transm. 209-228.
Cassarino et al. "An evaluation of the role of mitochondria in neurodegenerative diseases: mitochondrial mutations and oxidative pathology, protective nuclear responses, and cell death in neurodegeneration" 1999, Brain Res. Rev. 29:1-25.
Cassarino et al. "Cyclosporin A increases resting mitochondrial membrane potential in SY5Y cells and reverses the depressed mitochondrial membrane potential of Alzheimer's disease cybrids" May 13, 1998, Biochem. and Biophysical Research Comm. 248:168-173.
Cassarino et al. "Interaction among mitochondria, mitogen-activated protein kinases, and nuclear factor-kappaB in cellular models of Parkinson's disease" Apr. 2000, J Neurochem. 74(4):1384-92. PubMed PMID: 10737593.
Cassarino et al. "Pramipexole reduces reactive oxygen species production in vivo and in vitro and inhibits the mitochondrial permeability transition produced by the parkinsonian neurotoxin methylpyridinium ion" 1998, J. Neurochem. 71(1):295-301.
Cleveland et al. "From Charcot to Lou Gehrig: deciphering selective motor neuron death in ALS" Nov. 2001, Nature 2:806-819.
Corcoran et al. "Absence of retinoids can induce motoneuron disease in the adult rat and a retinoid defect is present in motoneuron disease patients" 2002, J. Cell. Sci. 115:4735-4741.
Corrigan et al. "Comparison of Pramipexole, Fluoxetine, and Placebo in Patients with Major Depression" 2000, Depression and Anxiety 11:58-65.
Cudkowicz et al. "Measures and Markers in Amyotrophic Lateral Sclerosis" Apr. 2004, NeuroRx: The Journal of the American Society for Experimental NeuroTherapeutics 1(2):273-283.
Cudkowicz et al. "Dexpramipexole versus placebo for patients with amyotrophic lateral sclerosis (EMPOWER): a ramdomised double-blind, phase 3 trial" Lancet Neurol. (2013), (12) pp. 1059-1067.
Danzeisen et al. "Targeted Antioxidative and Neuroprotective Properties of the Dopamine Agonist Pramipexole and Its Nondopaminergic Enantiomer SND919CL2x [(+)2-Amino-4, 5, 6, 7-tetrahydro-6-L-propylamino-benzathiazole Dihydrochloride]" 2006, J. Pharmacol. Exp. Ther. 316:189-199.
Davis et al. (Cancer Immunol Res. 2014;2:1-8—p. 5, Fig. 2).
Declaration of James P. Bennett Under 37 C.F.R. 1.132 dated Dec. 15, 2009.
Deigner et al. "Apoptosis Modulators in the Therapy of Neurodegenerative Diseases" Apr. 2000, Ex. Opin. Investigational Drugs 9(4):747-764 XP001012423.
Deng et al. "Elevation of cystatin C in susceptible neurons in Alzheimer's disease" Sep. 2001, Am. J. Pathol. 159(3):1061-1068.

Dooley et al. "Pramipexole. A Review of its Use in the Managemetn of Early and Advanced Parkinson's Disease" Jun. 1998, Drugs Aging 12(6):495-514.
Drobny et al. "Possible Extrapyramidal System Degradation in Parkinson's Disease" 2000, Brain Research Bulletin 53(4):425-430.
Email correspondence from James P. Bennett to Michael Bozik dated May 11, 2006 with a copy of a presentation entitled "ALS: An Investigator's View of the Disease and its Treatment".
Email correspondence from James P. Bennett to Michael Bozik dated Oct. 9, 2006 with a draft grant application.
Email correspondence from James P. Bennett to Michael Bozik dated Apr. 6, 2007 with a draft manuscript entitled "R(+) Pramipexole as a Neuroprotectant I: Effects of R(+) Pramipexole Treatment of ALS on ALSFRSr, Forced Vital Capacity and Neurophysiological Index".
Email correspondence from James P. Bennett to Michael Bozik dated Apr. 6, 2007 with a draft manuscript entitled "R(+) Pramipexole as a Neuroprotectant II: Tolerability and Pharmacokinetics in ALS of Esclating Doses to 300mg/day".
European Seach Report and Opinion dated Aug. 1, 2012 for EP 12163888.
European Search Report and Opinion dated Aug. 2, 2012 for EP 12164060.
European Search Report and Opinion dated May 10, 2012 for EP 11186875.
European Search Report dated Feb. 18, 2011 for EP10009931.
European Supplemental Search Report dated Apr. 8, 2010 for EP 08743922.
European Supplemental Search Report dated Apr. 9, 2010 for EP 08732306.9.
European Supplemental Search Report dated Nov. 23, 2006 for EP 02795869.
European Supplemental Search Report dated Oct. 4, 2010 for EP 10008579.4.
Extended European Search Report and Written Opinion dated Sep. 11, 2012 for EP 12164067.
Extended European Supplemental Search Report and Written Opinion dated Feb. 18, 2011 for EP10075571.
Feher et al. "Mitochondrial alternations of retinal pigment epithelium in age-related macular degenteration" Jun. 2006 (Printed from http://www.neurobiologyofaging.org/article/PIIS01974580005001545 on Dec. 11, 2009) Neurobiology of Aging 27(7) (Abstract, 2 pages).
Ferger et al. "The dopamine agonist pramipexole scavenges hydroxyl free radicals induced by striatal application of 6-hydroxydopamine in rats: an in vivo microdialysis study" Aug. 29, 2000, Brain Research 883:216-223.
Gennaro "Remington: The Science and Practice of Pharmacy, 20$^{th}$ Ed." Lippincott Williams & Wlkins, Baltimore, MD, 2000, Ch. 38:704-720.
Golebiewski et al. "Application of GC/MS for Identyfication of the Sideproducts in a Process of Preparation of Pramipexole" May 16, 2006, Book of Abstracts: The Fifth Multidisciplinary conference on Drug Research, Pielaszek Research (Warszawa, Poland) Poster No. 1-57, p. 49.
Goodall et al. "Association of the H63D polymorphism in the hemochromatosis gene with sporadic ALS" 2005, Neurology 65(6):934-937.
Goodman et al. "The Pharmaceutical Basis of Therapeutics, 6$^{th}$ Ed." 1980, MacMillan Publishing Co., New York (TOC).
Gu et al. "Pramipexole protects against apoptotic cell death by non-dopaminergic mechanisms" 2004, J. Neurochem. 91:1075-1081.
Gurney et al. "Benefit of Vitamin E, Riluzole, and Gabapentin in a Transgenic Model of Familial Amyotrophic Lateral Sclerosis" Feb. 1996, Ann. Neurol. 39(2):147-157.
Gurney et al. "Motor Neuron Degeneration in Mice That Express a Human Cu, Zn Superoxide Dismutase Mutation" Jun. 17, 1994, Science 264:1772-1775.
Haghikia et al. "Therapies for multiple sclerosis: translation achievements and outstanding needs" May 2013 Trends in Moleecular Medicine 19(5):309-319.

(56) References Cited

OTHER PUBLICATIONS

Halestrap "The Role of Mitochondria in Cell Death" Mar. 24, 2003, Endocrine Abstracts 5:513 (Abstract).
Hall et al. "Brain hydroxyl radical generation in acute experimental head injury" Feb. 1993, J. Neurochem. 60(2):588-594.
Hall et al. "Neuroprotective effects of the dopamine $D_2 / D_3$ agonist pramipexole against postischemic or methamphetamine-induced degeneration of nigrostriatal neurons" Aug. 6, 1996, Brain Research 742:80-88 (abstract).
Hansen et al. "First Generation Process for the Preparation of the DPP-IV Inhibitor Sitagliptin" 2005, Organic Proc. Res. & Dev. 9:634-639.
Hubble Pre-clinical Studies of Pramipexole: Clinical Relevance May 2000 Eur. J. Neurol. 7(Supp 1):15-20.
Initial Scientific Discussion for the Approval of Mirapex from the European Agency for the Evaluation of Medicinal Products (EMEA), 2005, www.emea.europa.eu/humandocs/PDFS/EPAR/Mirapexin/059097en6.pdf.
International Search Report and Written Opinion for PCT/US2008/057158 dated Jun. 29, 2009.
International Search Report and Written Opinion for PCT/US2010/39379 dated Aug. 25, 2010.
International Search Report and Written Opinion for PCT/US2013/054804 dated Mar. 21, 2014.
International Search Report and Written Opinion for PCT/US2014/019668 dated Jun. 9, 2014.
International Search Report and Written Opinion for PCT/US2014/050951, (2014).
International Search Report and Written Opinion for PCT/US2014/050943, (2014).
International Search Report for PCT/US2002/39970 dated Jul. 17, 2003.
International Search Report for PCT/US2006/031831 dated Dec. 12, 2006.
International Search Report for PCT/US2007/087639 dated Apr. 4, 2008.
International Search Report for PCT/US2008/057059 dated Jul. 11, 2008.
International Search Report for PCT/US2009/54292 dated Oct. 22, 2009.
International Search Report for PCT/US2011/38159 dated Dec. 12, 2011.
International Search Report for PCT/US2014/046380 dated Dec. 10, 2014.
Jacques et al. "Enantiomers, Racemates and Resolutions" 1981, John Wley and Sons, Inc., New York (TOC).
Johnson et al. (Relationships between drug activity and NCI preclinical in vitro and in vivo models and early clinical trials; British Journal of Cancer; (2001) 84 (10), 1424-1431).
Kamel et al. "Lead exposure and amyotrophic lateral sclerosis" May 2002, Epidemiology 13(3):311-319.
Kato et al. "A neurosphere-derived factor, cystatin C, supports differentiation of ES cells into neural stem cells" Apr. 11, 2006, PNAS USA 103(15):6019-6024.
Kitamura et al. "Protective Effects of the Antiparkinsonian Drugs Talipexole and Pramipexole against 1-Methyl-4-phenylpyridinium-Induced Apoptotic Death in Human Neuroblastoma SH-SY5Y Cells" 1998, Molecular Pharmacology 54:1046-1054.
Lahortiga et al. "Activity of imatinib in systemic mastocytosis with chronic basophilic leukemia and a PRKG2-PDGFRB fusion" 2008, Haematological/The Hematology Journal 93(1): 51-52, 55.
Le et al. "Antioxidant property of pramipexole independent of dopamine receptor activation in neuroprotection" 2000, J. Neural. Transm. 107(10):1165-73.
Lee et al. "Carcinogenicity Predictions for a Group of 30 Chemicals Undergoing Rodent Cancer Bioassays Based on Rules Derived from Subchronic Organ Toxicities" Oct. 1996, Environmental Health Perspectives 104(5):1059-1063.

Levy et al. "Stroke in Icelandic Patients With Hereditary Amyloid Angiopathy is Related to a Mutation in the Cystatin C Gene, An Inhibitor of Cysteine Proteases" May 1989, J. Exp. Med. 169(5):1771-1778.
Liang et al. "Oxidative stress-induced mitochondrial DNA damage in human retinal pigment epithelial cells: a possible mechanism for RPE aging and age-related macular degeneration" Apr. 1, 2003, Exp. Eye Res. 76(4):397-403.
Lieberman et al. "Clinical evaluation of pramipexole in advanced Parkinson's disease: Results of a double-blind, placebo-controlled, parallel-group study" 1997, Neurology 49:162-168.
Lieberman et al. "Pharmaceutical Dosage Forms: Disperse Systems" 1996, Marcel Dekker, Inc., New York vol. 2 (TOC).
Lieberman et al. "Pharmaceutical Dosage Forms: Tablets" 1989, Marcel Dekker, Inc., New York vol. 1 (TOC).
Lin et al. "Large-scale protein identification using mass spectrometry" 2003, Biochimica et Biophysica Acta 16460(2):1-10.
Lofberg, et al. "Immunohistochemical characterization of the amyloid deposits and quantitation of pertinent cerebrospinal fluid proteins in hereditary cerebral hemorrhage with amyloidosis" Mar.-Apr. 1987, Stroke 18(2):431-440.
Lomen-Hoerth "Amyotrophic lateral sclerosis from bench to bedside" 2008, Semin. Neurol. 28(2):205-211.
Love "Oxidative Stress in Brain Ischemia" Apr. 5, 1999, Brain Pathology 9(1)119-131 (Abstract).
Malaspina et al. "Differential expression of 14 genes in amyotrophic lateral sclerosis spinal cord detected using gridded eDNA arrays" 2001, J. Neurochemistry 77(1):132-145.
Martens "Cloning and Sequence Analysis of Human Pituitary eDNA Encoding the Novel Polypeptide 7B2" Jul. 1988, FEBS Letters 234(1):160-164.
Martens et al. "The novel pituitary polypeptide 7B2 is a highly-conserved protein coexpressed with proopiomelanocortin" Apr. 1989, Eur. J. Biochem. 181(1):75-79.
Matthews et al. "Assessment of the Health Effects of Chemicals in Humans: I. QSAR Estimation of the Maximum Recommended Therapeutic Dose (MRTD) and No Effect Level (NOEL) of Organic Chemicals Based on Clinical Trial Data" 2004, Current Drug Discovery Technologies 1:61-76.
Mbikay et al. "Neuroendocrine secretory protein 7B2: structure, expression and functions" Jul. 15, 2001, Biochem. J. 357(2):329-342.
Menzies et al. "Mitochondrial dysfunction in a cell culture model of familial amyotrophic lateral sclerosis" Jul. 2002, Brain 125(7):1522-1533.
Merck Manuals Online Medical Library, Age-Related Macular Degeneration (ARMD), 2005, printed Aug. 13, 2008 from http://www.merck.com/mmpe/print/sec09/ch106/ch106b.html, 2 pages.
Mey et al. "Retinoic acid signaling in the nervous system of adult vertebrates" 2004, Neuroscientist 10(5):409-421.
Mhatre et al. "Oxidative Stress and Neuroinflammation in Alzheimer's Disease and Amyotrophic Lateral Sclerosis; Common Links and Potential Therapeutic Targets" Apr. 2004, J. Alzheimers Dis. 6(2):147-157 (abstract only).
Mierau et al. "Pramipexole binding and activation of cloned and expressed dopamine $D_2$, $D_3$ and $D_4$ receptors" 1995, Eur. J. Pharmacol. 290:29-36.
Miklya et al. "A pharmacological analysis elucidating why, in contrast to (−)-deprenyl (selegiline), α-tocopherol was ineffective in the DATATOP study" 2003, Life Sciences 72:2641-2648.
Mirapex® Prescribing Information from Boehringer Ingelheim, 2006, http.//www.biopsychiatry.com/pramipexole-mirapex.pdf (retrieved May 10, 2012).
Moore et al. "An Efficient and Operationally Convenient General Synthesis of Tertiary Amines by Direct Alkylation of Secondary Amines with Alkyl Halides in the Presence of Huenig's Base" 2005, ARKIVOC 6:287-292.
Nagai et al. "Rats expressing human cytosolic copper-zinc superoxide dismutase transgenes with amyotrophic lateral sclerosis: associated mutations develop motor neuron disease" Dec. 1, 2001, J. Neurosci. 21(23):9246-9254.

(56) References Cited

OTHER PUBLICATIONS

Nilsen et al. "Mitochondria as Therapeutic Targets of Estrogen Action in the Central Nervous System" Aug. 2004, Curr. Drug Targets—CNS Neurol. Disord. 3(4):297-313.
Ong et al. "An Evaluation of the Use of Two-Dimensional Gel Electrophoresis in Proteomics" 2001, Biomolecular Engineering 18(5):195-205.
Palliative (n.d.) The American Heritage® Stedman's Medical Dictionary, Retrieved Jun. 12, 2009, from Dictionary.com website: http://dictionary.reference.com/browse/palliative.
Paquet et al. "The neuroendocrine precursor 7B2 is a sulfated protein proteolytically processed by a ubiquitous furin-like convertase" Jul. 29, 1994, J. Biol. Chem. 269(30):19279-19285.
Pattee et al. "Reduction of oxidative stress in amyotrophic lateral sclerosis following pramipexole treatment" Jan. 2003, Amyotrophic Lateral Sclerosis and Other Motor Neuron Disorders 4(2):90-95 (abstract).
Paulson "Protein Fate in Neurodegenerative Proteinopathies: Polyglutamine Diseases Join the (Mis) Fold" 1999, Am. J. Hum. Genet. 64(2):339-345.
Petersen et al. "Impaired Mitochondrial Activity in the Insulin-Resistant Offspring of Patients with Type 2 Diabetes" 2004, New England Journal of Medicine 350:664-671.
Piercey et al. "Excitation of type II anterior caudate neurons by stimulation of dopamine $D_3$ receptors" 1997, Brain Research 762:19-28.
Piercey et al. "Inhibition of dopamine neuron firing by pramipexole, a dopamine $D_3$ receptor-prefering agonist: comparison to other dopamine receptor agonists" 1996, European J. of Pharmac. 312:35-44.
Public Statement on Mirapex, Sudden Onset of Sleep from the European Agency for the Evaluation of Medicinal Products (EMEA), Jul. 19, 1999, www.emea.europa.eu/pdfs/human/press/pus/2064299.pdf.
Ranganathan et al, "Proteomic profiling of cerebrospinal fluid identifies biomarkers for amyotrophic lateral sclerosis" Dec. 2005, J. Neurochem. 95(5):1461-1471.
Robberecht "Oxidative Stress in Amyotrophic Lateral Sclerosis" 2000, J. Neurol. 247(1):11-16 (abstract).
Rowland et al. "Amyotrophic Lateral Sclerosis" May 2001, N Eng Journal of Medicine, 344:1688-1700.
Ryberg et al. "Discovery and Verification of Amyotrophic Lateral Sclerosis Biomarkers by Proteomics" Jul. 2010, Muscle & Nerve 42(1):104-111.
Sanchez et al. "Cystatin C as a potential cerebrospinal fluid marker for the diagnosis of Creutzfeldt-Jakob disease" 2004, Proteomics 4(8):2229-2233.
Sayeed et al. "Patch Clamp Reveals Powerful Blockade of the Mitochondrial Permeability Transition Pore by the D2-Receptor Agonist Pramipexole" 2006, FASB Journal 20:556-558.
Schilling et al. "Neuroendocrine and side effect profile of pramipexole, a new dopamine receptor agonist, in humans" 1992, Clin. Pharmacol. Ther. 51:541-548.
Schmidt et al. "Neurodegenerative diseases of the retina and potential for protection and recovery" Jun. 2008 (printed from http://www.nncbi.nim,nih/gov/pubmed/19305795?dopt_Abstract) Curr. Neuropharmacol. 6(2) (Abstract, 1 page).
Schneider et al. "Dopamine Autoreceptor Agonists: Resolution and Pharmacological Activity of 2,6-Diaminotetrahydrobenzothiazole and an Aminothiazole Analogue of Apomorphine" 1987, *J. Med. Chem.* 30:494-498.
Schuelke et al. "Myostatin Mutation Associated With Gross Muscle Hypertrophy in a Child" 2004, N. Engl. J. Med. 350:2682-2688 (Para.1).
Shannon et al. "Efficacy of Pramipexole, a Novel Dopamine Agonist, as Monotherapy in Mild to Moderate Parkinson's Disease" 1997, Neurology 49(3)a;724-728.
Sousa et al. "Deposition of transthyretin in early stages of familial amyloidotic polyneuropathy: evidence for toxicity of nonfibrillar aggregates" Dec. 2001, Am. J. Pathol. 159(6):1993-2000.

Sousa et al. "Evidence for early cytotoxic aggregates in transgenic mice for human transthyretin Leu55Pro" Nov. 2002, Am. J. of Pathol. 161(5):1935-1948.
Stein et al. "Neutralization of transthyretin reverses the neuroprotective effects of secreted amyloid precursor protein (APP) in APPsw mice resulting in tau phosphorylation and loss of hippocampal neurons: Support for the amyloid hypothesis" Sep. 1, 2004, J. Neurosci. 24(35):7707-7717.
The Foundation Fighting Blindness "Animal Models for Studying Inherited Degenerative Retinal Disease" 2000 (printed from www.retina-international.org/sci-news/animmod.doc on Jan. 11, 2009) The Foundation Fighting Blindness (23 pages).
Tombran-Tink et al. "Neuroprotection in Macular Degeneration" 2005, Age-Related Macular Degeneration: A Comprehensive Textbook (Lippincott Williams & Wilkins), 29:335-336.
Tsuzuki et al. "Structure of the Human Prealbumin Gene" Oct. 5, 1984, J. Biol. Chem. 260(22):12224-12227.
Uemichi et al. "A New Mutant Transthyretin (Arg 10) Associated with Familial Amyloid Polyneuropathy" 1992, J. Med. Genet. 29:888-891.
U.S. Dept. of HHS FDA CDER (Guidance for Industry), Jul. 2005, 30 pp.
Voskoglou-Nomikos et al. (Clinical Predictive Value of the in Vitro Cell Line, Human Xenograft, and Mouse Allograft Preclinical Cancer Models; Clinical Cancer Research; vol. 9: 4227-4239; Sep. 15, 2003).
Wang et al. "R+ pramipexole as a mitochondrially focused neuroprotectant: initial early phase studies in ALS" Feb. 2008, Amyotroph Lateral Scler. 9(1):50-58. PubMed PMID: 18270879.
Wedi et al. "Chronic urticarial serum induces histamine release, leukotriene production, and basophil CD63 surface expression-inhibitory effects of anti-inflammatory drugs" Journal of allegery and clinical immunology, Mar. 2000, 105(3):552-560.
Winkler et al. "Oxidative damage and age-related macular degeneration" Nov. 3, 1999, Mol. Vis. 5:32 (Abstract).
Wong "A 384-well cell-based phosphor-ERK assay for dopamine D2 and D3 receptors" 2004, Analytical Biochem. 333:265-272.
Wong et al. "Activation of Extracellular Signal-Regulated Kinase by Dopamine D2 and D3 Receptors" 2003, Society for Neuroscience Abstracts (retrieved on line at sfn.scholarone.com/itin2003/main.html?new_page_id=126&abstract_id=3866&p_num=363.4 &is_tech=0 on Jun. 23, 2008).
Worker "Novel Therapeutic Strategies" 1999, IDRUGS, Current Drugs Ltd, GB 2(9):848-852 XP000972503.
Wright et al. "Influence of Probenecid (PR) and Cimetidine (C) on Pramipexole (PX) Pharmacokinetics" Feb. 1995, Clin. Pharmacol. & Ther. 59(2):PII-99 (abstract).
Written Opinion of International Search Authority dated Aug. 15, 2005 for PCT/US2006/031831.
Zheng et al. "Purification and identification of an estrogen binding protein from rat brain: oligomycin sensitivity-conferring protein (OSCP), a subunit of mitochondrial F0F1-ATP synthase/ATPase" Jan. 1999, J. Ster. Biochem. Mol. Biol. 68(1-2):65-75.
B.R. Brooks, "El Escorial World Federation of Neurology Criteria for the Diagnosis of Amyotrophic Lateral Sclerosis", 1994, Journal of the Neurological Sciences, vol. 124, Suppl., pp. 96-107.
Brooks, et al., "El Escorial revisited: Revised criteria for the diagnosis of amyotrophic lateral sclerosis", 2000, ALS and other motor neuron disorders, vol. 1, pp. 293-299.
Cudkowicz et al., "The effects of dexpramipexole (KNS-760704) in individuals with amyotrophic lateral sclerosis", Dec. 2011, Nature Medicine, vol. 17, No. 12, pp. 1652-1656; Supplemental Materials included with total of 27 pages.
Rudnicki et al., "Dexpramipexole effects on functional decline and survival in subjects with amyotrophic lateral sclerosis in a Phase II study: Subgroup analysis of demographic and clinical characteristics", Feb. 1, 2013, Amyotrophic Lateral Sclerosis and Frontotemporal Degeneration, vol. 14, pp. 44-51.
National Institutes of Health/ U.S. National Library of Medicine, "Creatine phosphokinase test", Updated Jan. 9, 2015, URL of this page: //www.nlm.nih.gov/medlineplus/ency/article/003503.htm, pp. 1-4.

(56) References Cited

OTHER PUBLICATIONS

International Search Report and Written Opinion for PCT/US2016/22067 dated Jun. 3, 2016.
Weller et al. "The idiopathic hypereosinophilic syndrome." Blood 83.10 (1994): 2759-2779.
PDF regarding ALS from Florida Hospital, retrieved on Jul. 12, 2018.

* cited by examiner

SYNTHESIS OF CHIRALLY PURIFIED SUBSTITUTED BENZOTHIAZOLE DIAMINES

CROSS-REFERENCE TO RELATED APPLICATIONS

The present application is a continuation of U.S. patent application Ser. No. 13/973,987, filed Aug. 22, 2013, which is a continuation of U.S. patent application Ser. No. 12/049,235, filed Mar. 14, 2008 now U.S. Pat. No. 8,519,148, which claims priority to U.S. Provisional application Ser. No. 60/894,829, filed Mar. 14, 2007 and U.S. Provisional application Ser. No. 60/894,814, filed Mar. 14, 2007, the disclosures of which are incorporated herein by reference in their entireties.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

1. Field of Invention
Not applicable
2. Description of Related Art

The compound 2-amino-4,5,6,7-tetrahydro-6-(propylamino)benzothiazole is a synthetic aminobenzothiazole derivative whose (6S) enantiomer, commonly known as pramipexole and commercially available under the Mirapex® name, is a potent dopamine agonist, and thus, mimics the effects of the neurotransmitter dopamine. Pramipexole has also been shown to have both neuroprotective and dopaminergic activities, presumably through inhibition of lipid peroxidation, normalization of mitochondrial metabolism and/or detoxification of oxygen radicals. Therefore, pramipexole may have utility as an inhibitor of the cell death cascades and loss of cell viability observed in neurodegenerative diseases and is indicated for treating Parkinson's disease, cluster headaches, restless legs syndrome and bipolar disorder with only small daily doses required and tolerated by patients activates dopamine receptors. Additionally, oxidative stress may be caused by an increase in oxygen and other free radicals, and has been associated with the fatal neurodegenerative disorder amyotrophic lateral sclerosis (ALS). ALS is a progressive neurodegenerative disorder involving the motor neurons of the cortex, brain stem, and spinal cord. About 10% of all ALS patients are familial cases, of which 20% have mutations in the superoxide dismutase 1 (SOD-1) gene. The SOD-1 enzyme may play a pivotal role in the pathogenesis and progression of familial amyotrophic lateral sclerosis (FALS). Recent studies also link the premature neuronal death associated with ALS to mutated mitochondrial genes which lead to abnormalities in functioning of the energy production pathways in mitochondria.

The neuroprotectant activity of both enantiomers of pramipexole have typical therapeutic doses expected to be in the range of about 10 mg/day to about 1,500 mg/day. However, the pramipexole's agonistic effect on of the $D_2$ family of dopamine receptors only requires therapeutic doses that range between 0.5 and 5.0 mg/day, and even these relatively low doses adverse side effects have been reported. For example, the Boehringer Ingelheim product insert for Mirapex® sets the maximally tolerated dose for humans at 4.5 mg/day, and a dose of pramipexole as low as 1.5 mg has been shown to cause somnolence in humans. Single dose toxicity of pramipexole after oral administration has been studied in rodents, dogs, monkeys and humans. In rodents, death occurred at doses of 70-105 mg/kg and above which is equivalent to a human dose of 7-12 mg/kg/ or approximately 500-850 mg for a 70 kg (~150 lb) individual. In dogs, vomiting occurred at 0.0007 mg/kg and above, while monkeys displayed major excitation at 3.5 mg/kg. In human subjects, an initial single dose of pramipexole of greater than 0.20 mg was not tolerated. All species showed signs of toxicity related to exaggerated pharmacodynamic responses to the pramipexole related to dopaminergic agonism.

Thus, a clinical use of pramipexole as a mitochondria-targeted antioxidant is unlikely, as the high doses needed for the neuroprotective or anti-oxidative/mitochondrial normalization action are not accessible due to high dopamine receptor affinity associated with the (6S) enantiomer. In contrast, (6R)-4,5,6,7-tetrahydro-N6-propyl-2,6-benzothiazole-diamine is an effective mitochondria-targeted neuroprotectant that exhibits excellent anti-oxidative properties when administered without adverse side effects. Thus, higher doses of (6R)-4,5,6,7-tetrahydro-N6-propyl-2,6-benzothiazole-diamine can be tolerated by patients and will allow greater brain, spinal cord and mitochondrial concentrations increasing the degree to which oxidative stress and/or mitochondrial dysfunction may be reduced. The neuroprotective effect of the compositions of this disclosure may also be derived at least in part from the ability of the (6R) enantiomer of pramipexole to prevent neural cell death by at least one of three mechanisms. First, the (6R) enantiomer of pramipexole may be capable of reducing the formation of reactive oxygen species in cells with impaired mitochondrial energy production. Second, the (6R)-4,5,6,7-tetrahydro-N6-propyl-2,6-benzothiazole-diamine may partially restore the reduced mitochondrial membrane potential that is correlated with Alzheimer's, Parkinson's, Huntington's and amyotrophic lateral sclerosis diseases. Third, the (6R) enantiomer of pramipexole may block the apoptotic cell death pathways which are produced by pharmacological models of Alzheimer's disease, Parkinson's disease, Huntington's disease, amyotrophic lateral sclerosis diseases and mitochondrial impairment. High doses of (6R)-4,5,6,7-tetrahydro-N6-propyl-2,6-benzothiazole-diamine required to elicit these neuroprotective effects generally require highly pure preparations of (6R)-4,5,6,7-tetrahydro-N6-propyl-2,6-benzothiazole-diamine which take into account the upper limit of (6S)-4,5,6,7-tetrahydro-N6-propyl-2,6-benzothiazole-diamine contamination (0.5 mg to 5.0 mg).

Processes for the preparation of 2-amino-4,5,6,7-tetrahydro-6-(propylamino)benzothiazole using a simple alkylation reaction were first described in U.S. Pat. Nos. 4,843,086 and 4,886,812. Other preparations of 2-amino-4,5,6,7-tetrahydro-6-(propylamino)benzothiazole have been described that involve reductive amination rather than simple alkylation and, thus, produce a mixture of the R and S optical isomers with no direct means for further purification of the optical isomers. These known processes for the production of 2-amino-4,5,6,7-tetrahydro-6-(propylamino) benzothiazole are expensive, labor intensive, and utilize hydride reducing agents that pose safety risks. Furthermore, there are currently no known processes for the direct synthesis of the pure (6R)-4,5,6,7-tetrahydro-N6-propyl-2,6-benzothiazole-diamine from a diamine. Therefore, the R isomer must be synthesized as a mixture of the optical isomers that is purified by expensive and time consuming methods that may utilize other problematic substances. Moreover, known processes involving deamination result in a loss of enantiomeric purity, and methods useful for resolution of the optical isomers from mixtures fall short of producing chirally and chemically pure preparations of the R enantiomer or the S enantiomer.

BRIEF SUMMARY OF THE INVENTION

Embodiments of the invention presented herein are directed to a process for preparing a chirally purified substituted 4,5,6,7,-tetrahydro-benzothaizole diamine including the steps of: heating a solution comprising entantiomerically enriched 4,5,6,7-tetrahydro-benzothiazole diamine of general formula (1):

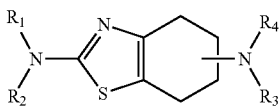
(1)

wherein:
R$_1$ represents a hydrogen atom, an alkyl group having 1 to 6 carbon atoms, an alkenyl or alkynyl group each having 3 to 6 carbon atoms, an alkanoyl group having 1 to 6 carbon atoms, a phenyl alkyl or phenyl alkanoyl group having 1 to 3 carbon atoms in the alkyl part, whilst the above-mentioned phenyl nuclei may be substituted by 1 or 2 halogen atoms;
R$_2$ represents a hydrogen atom or an alkyl group with 1 to 4 carbon atoms;
R$_3$ represents a hydrogen atom, an alkyl group with 1 to 7 carbon atoms, a cycloalkyl group having 3 to 7 carbon atoms, an alkenyl or alkynyl group having 3 to 6 carbon atoms, an alkanoyl group having 1 to 7 carbon atoms, a phenyl alkyl or phenyl alkanoyl group having 1 to 3 carbon atoms in the alkyl part, whilst the phenyl nucleus may be substituted by fluorine, chlorine or bromine atoms,
R$_4$ represents a hydrogen atom, an alkyl group with 1 to 4 carbon atoms, an alkenyl or alkynyl group having 3 to 6 carbon atoms; and
at least one or R$_1$, R$_2$, R$_3$ or R$_4$ is a hydrogen in an organic solvent; and an alkyl sulfonate or an alkyl halide in a solvent to form a reaction mixture reacting the reaction mixture; and recovering a chirally purified substituted 4,5,6,7-tetrahydro-benzothiazole diamine.

In various embodiments, the alkyl sulfonate may be of general formula (11):

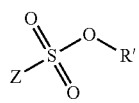
(11)

wherein:
R' is an alkyl group having 1 to 6 carbons, or a cycloalkyl, alkenyl, alkynyl, allyl, having 1 to 10 carbon atoms, or a benzyl, chlorobenzyl, phenyl or phenyl alkyl; and
Z is an alkyl group having 1 to 6 carbons, or a cycloalkyl, alkenyl, alkynyl, allyl, having 1 to 10 carbon atoms, or a benzyl, chlorobenzyl, phenyl or phenyl alkyl. In particular embodiments, X may be a propyl and, in some embodiments, the alkyl sulfonate may be a propyl sulfonate selected from n-propyl tosylate, n-propyl methoxysulfonate and combinations thereof. In other embodiments, the alkyl halide may be of general formula (12):

R'—X (12)

wherein:
R' is an alkyl group having 1 to 6 carbons, or a cycloalkyl, alkenyl, alkynyl, allyl, having 1 to 10 carbon atoms, or a benzyl, chlorobenzyl, phenyl or phenyl alkyl; and
X is any halide including, for example, fluorine, chlorine, bromine or iodide.

In particular embodiments, X may be a propyl, and in some embodiments, the alkyl halide may be a propyl halide selected from n-propyl bromide, n-propyl chloride, n-propyl fluoride, n-propyl iodide and combinations thereof.

The chirally purified substituted 4,5,6,7-tetrahydro-benzothiazole diamine of various embodiments may be at least greater than about 97% chirally pure. In some embodiments, the chirally purified substituted 4,5,6,7-tetrahydro-benzothiazole diamine may be at least greater than about 99% chirally pure, and in other embodiments, chirally purified substituted 4,5,6,7-tetrahydro-benzothiazole diamine is at least about 99.9% chirally pure.

The chemical purity of the substituted 4,5,6,7-tetrahydro-benzothiazole diamine of various embodiments may be greater than about 99%. In some embodiments, the chemical purity of the substituted 4,5,6,7-tetrahydro-benzothiazole diamine may be greater than about 99.9%, and in other embodiments, the chemical purity of the substituted 4,5,6,7-tetrahydro-benzothiazole diamine is greater than about 99.99%.

In some embodiments, the entantiomerically enriched 4,5,6,7-tetrahydro-benzothiazole diamine may be entantiomerically enriched for an (6R) entantiomer and the chirally purified substituted 4,5,6,7-tetrahydro-benzothiazole diamine is chirally purified for an (6R) entantiomer, and in particular embodiments, the entantiomerically enriched 4,5,6,7-tetrahydro-benzothiazole diamine may be entantiomerically enriched for (6R)-2,6 diamino-4,5,6,7-tetrahydro-benzothiazole and the chirally purified substituted 4,5,6,7-tetrahydro-benzothiazole may be (6R)-4,5,6,7-tetrahydro-N6-propyl-2,6-benzothiazole-diamine. In other embodiments, the entantiomerically enriched 4,5,6,7-tetrahydro-benzothiazole diamine may be entantiomerically enriched for an (6S)-entantiomer and the chirally purified substituted 4,5,6,7-tetrahydro-benzothiazole diamine is chirally purified for an (6S) entantiomer, and in certain embodiments, the entantiomerically enriched 4,5,6,7-tetrahydro-benzothiazole diamine may be entantiomerically enriched for (6S)-2,6 diamino-4,5,6,7-tetrahydro-benzothiazole and the chirally purified substituted 4,5,6,7-tetrahydro-benzothiazole is (6S)-4,5,6,7-tetrahydro-N6-propyl-2,6-benzothiazole-diamine. In still other embodiments, the entantiomerically enriched 4,5,6,7-tetrahydrobenzothiazole diamine may be a ratio of greater than about 1:4 (6R)-entantiomer to (6S)-entantiomer to about 4:1 (6R)-entantiomer to (6S)-entantiomer.

The solvent of various embodiments may be selected from an organic solvent and an organic solvent mixed with water, and in some embodiments, the solvent may selected from, but not limited to, ethanol, 1-propanol, n-butanol, dihydrofuran, dimethylformamide, dimethyl, dimethylacetamide, hexamethylphosphoric triamide or mixtures or hydrates thereof.

In some embodiments, the steps of heating, reacting and recovering each independently include stirring. In other embodiments, the steps of heating and reacting may each independently be carried out at a temperature of from about 50° C. to about 125° C. In yet other embodiments, the step of heating may further include adding the alkyl sulfonate or alkyl halide to the heated 4,5,6,7-tetrahydro-benzothiazole diamine. In still other embodiments, the step of adding may be carried out for about 0.5 hours to about 2 hours, and in certain embodiments, about 1.0 to about 2.0 molar equivalents of the alkyl sulfonate or alkyl halide may be added. In particular embodiments, the step of reacting may be carried out for up to about 12 hours. In yet other embodiments, the step of recovering may include one or more steps selected from, but not limited to, filtering the reaction mixture to isolate a precipitate, washing a precipitate, and drying a precipitate, and the process of certain embodiments may include the step of cooling the reaction mixture to a temperature of about 25° C. after the step of reacting.

Other embodiments of the invention include a process for preparing a chirally purified substituted 4,5,6,7-tetrahydro-benzothiazole diamine including the steps of heating a solution comprising an entantiomerically enriched 4,5,6,7-tetrahydro-benzothiazole diamine of general formula (1):

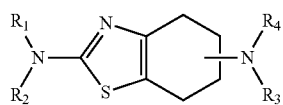

(1)

wherein:

$R_1$ represents a hydrogen atom, an alkyl group having 1 to 6 carbon atoms, an alkenyl or alkynyl group each having 3 to 6 carbon atoms, an alkanoyl group having 1 to 6 carbon atoms, a phenyl alkyl or phenyl alkanoyl group having 1 to 3 carbon atoms in the alkyl part, whilst the above-mentioned phenyl nuclei may be substituted by 1 or 2 halogen atoms;

$R_2$ represents a hydrogen atom or an alkyl group with 1 to 4 carbon atoms;

$R_3$ represents a hydrogen atom, an alkyl group with 1 to 7 carbon atoms, a cycloalkyl group having 3 to 7 carbon atoms, an alkenyl or alkynyl group having 3 to 6 carbon atoms, an alkanoyl group having 1 to 7 carbon atoms, a phenyl alkyl or phenyl alkanoyl group having 1 to 3 carbon atoms in the alkyl part, whilst the phenyl nucleus may be substituted by fluorine, chlorine or bromine atoms, $R_4$ represents a hydrogen atom, an alkyl group with 1 to 4 carbon atoms, an alkenyl or alkynyl group having 3 to 6 carbon atoms; and at least one or $R_1$, $R_2$, $R_3$ or $R_4$ is a hydrogen in an organic solvent;

adding to the heated solution propyl sulfonate or a propyl halide to form a reaction mixture; and reacting the reaction mixture.

In some embodiments, the propyl sulfonate may be selected from n-propyl tosylate, n-propyl methoxysulfonate and combinations thereof, and in other embodiments, the propyl halide is selected from n-propyl bromide, n-propyl chloride, n-propyl fluoride, n-propyl iodide and combinations thereof.

The chirally purified substituted 4,5,6,7-tetrahydro-benzothiazole diamine of various embodiments may be at least greater than about 97% chirally pure. In some embodiments, the chirally purified substituted 4,5,6,7-tetrahydro-benzothiazole diamine is at least greater than about 99% chirally pure, and in other embodiments, the chirally purified substituted 4,5,6,7-tetrahydro-benzothiazole diamine is at least about 99.9% chirally pure.

The chemical purity of the substituted 4,5,6,7-tetrahydro-benzothiazole diamine of various embodiments may be greater than about 99%. In some embodiments, the chemical purity of the substituted 4,5,6,7-tetrahydro-benzothiazole diamine is greater than about 99.9%, and in other embodiments, the chemical purity of the substituted 4,5,6,7-tetrahydro-benzothiazole diamine is greater than about 99.99%.

In certain embodiments, the entantiomerically enriched 4,5,6,7-tetrahydro-benzothiazole may be enriched for (6R) 4,5,6,7-tetrahydro-benzothiazole diamine and the chirally purified substituted 4,5,6,7-tetrahydro-benzothiazole diamine may be (6R)-4,5,6,7-tetrahydro-N6-propyl-2,6-benzothiazole-diamine. In certain other embodiments, the entantiomerically enriched 4,5,6,7-tetrahydro-benzothiazole diamine may be enriched for (6S) 4,5,6,7-tetrahydro-benzothiazole diamine and the chirally purified substituted 4,5,6,7-tetrahydro-benzothiazole diamine may be (6S)-4,5,6,7-tetrahydro-N6-propyl-2,6-benzothiazole-diamine. In some embodiments, the entantiomerically enriched 4,5,6,7-tetrahydro-benzothiazole diamine may include a mixture of (6R) 4,5,6,7-tetrahydro-benzothiazole diamine. and (6S) 4,5,6,7-tetrahydro-benzothiazole diamine and the chirally purified substituted 4,5,6,7-tetrahydro-benzothiazole diamine may include a mixture of (6R)-4,5,6,7-tetrahydro-N6-propyl-2,6-benzothiazole-diamine and (6S)-4,5,6,7-tetrahydro-N6-propyl-2,6-benzothiazole-diamine. In particular embodiments, the mixture may be a racemic mixture. In other embodiments, the enantiomerically enriched mixture may be a ratio of greater than about 1:4 (6R) 4,5,6,7-tetrahydro-benzothiazole diamine and (6S) 4,5,6,7-tetrahydro-benzothiazole diamine to about 4:1 (6R) 4,5,6,7-tetrahydro-benzothiazole diamine and (6S) 4,5,6,7-tetrahydro-benzothiazole diamine.

In some embodiments, the solvent may be selected from a polar or organic solvent and a polar or organic solvent mixed with water, and in certain embodiments, the solvent may be selected from ethanol, 1-propanol, n-butanol, dihydrofuran, dimethylformamide, dimethyl, dimethylacetamide, hexamethylphosphoric triamide or mixtures or hydrates thereof. In other embodiments, the steps of heating and reacting each independently may include stirring. In still other embodiments, the steps of heating, adding and reacting may each independently be carried out at a temperature of from about 50° C. to about 125° C. In yet other embodiments, the process may further include the step of cooling the reaction mixture to a temperature of about 25° C. after the step of reacting. In particular embodiments, the step of adding may be carried out for up to about 2 hours. Various embodiments may further include the step of recovering the chirally purified substituted 4,5,6,7-tetrahydro-benzothiazole diamine, and in some embodiments, recovering may include one or more steps selected from filtering the mixture to isolate a precipitate, washing a precipitate, and drying a precipitate. In particular embodiments, about 1.0 to about 2.0 molar equivalents of the propyl sulfonate or propyl halide may be added.

Various embodiments of the invention also include chirally purified 2-amino-4,5,6,7-tetrahydro-6-(propylamino) benzothiazole prepared by a process including the steps of: heating a solution comprising entantiomerically enriched 2,6 diamino-4,5,6,7-tetrahydro-benzothiazole and a propyl halide or a propyl sulfonate to form a reaction mixture; reacting the reaction mixture; and recovering the chirally purified 2-amino-4,5,6,7-tetrahydro-6-(propylamino)benzothiazole. In some embodiments, the propyl sulfonate may be selected, from, but not limited to, n-propyl tosylate, n-propyl methoxysulfonate and combinations thereof, and in other embodiments, the propyl halide may be selected from n-propyl bromide, n-propyl chloride, n-propyl fluoride, n-propyl iodide and combinations thereof.

In various embodiments, the chirally purified 2-amino-4,5,6,7-tetrahydro-6-(propylamino)benzothiazole may be at least greater than about 97% chirally pure. In some embodiments, the chirally purified 2-amino-4,5,6,7-tetrahydro-6-(propylamino)benzothiazole may be at least greater than about 99% chirally pure, and in other embodiments, the chirally purified 2-amino-4,5,6,7-tetrahydro-6-(propylamino)benzothiazole is at least about 99.9% chirally pure.

The chemical purity of the 2-amino-4,5,6,7-tetrahydro-6-(propylamino)benzothiazole of various embodiments may be greater than about 99%. In some embodiments, the chemical purity of the 2-amino-4,5,6,7-tetrahydro-6-(propylamino)benzothiazole is greater than about 99.9%, and in other embodiments, the chemical purity of the 2-amino-4,5,6,7-tetrahydro-6-(propylamino)benzothiazole is greater than about 99.99%.

In particular embodiments, the entantiomerically enriched 2,6 diamino-4,5,6,7-tetrahydro-benzothiazole may be a ratio of greater than about 2:1 (6R)-2,6 diamino-4,5,6,7-tetrahydro-benzothiazole to (6S) 2,6 diamino-4,5,6,7-tetrahydro-benzothiazole.

In some embodiments, the solvent may be selected from an organic solvent and an organic solvent mixed with water, and in certain embodiments, the solvent may be selected from ethanol, 1-propanol, n-butanol, dihydrofuran, dimethylformamide, dimethyl, dimethylacetamide, hexamethylphosphoric triamide or mixtures or hydrates thereof.

In various embodiments, the steps of heating and reacting may each independently include stirring, and in some embodiments, the steps of heating and reacting may each be independently carried out at a temperature of from about 50° C. to about 125° C. In other embodiments, the process may further include cooling the reaction mixture to a temperature of about 25° C. after the step of reacting. In yet other embodiments, the process may further include the step of adding the propyl halide or propyl sulfonate to heated entantiomerically enriched 2,6 diamino-4,5,6,7-tetrahydro-benzothiazole, and in certain embodiments, the step of adding may be carried out for up to about 2 hours. In particular embodiments, about 1.0 to about 2.0 molar equivalents of the propyl sulfonate or propyl halide may be added. In still other embodiments, the step of reacting may be carried out for up to about 12 hours. In further embodiments, the step of recovering may include one or more steps selected from filtering the mixture to isolate a precipitate, washing a precipitate, and drying a precipitate.

Various other embodiments of the invention include a process for preparing a chirally purified 2-amino-4,5,6,7-tetrahydro-6-(propylamino)benzothiazole including the steps of heating a solution comprising 2,6 diamino-4,5,6,7-tetrahydro-benzothiazole in an organic solvent; adding to the heated solution propyl sulfonate or a propyl halide to form a reaction mixture; and reacting the reaction mixture for up to about 12 hours. In some embodiments, the propyl sulfonate may be selected from n-propyl tosylate, n-propyl methoxysulfonate and combinations thereof, and in other embodiments, the propyl halide is selected from n-propyl bromide, n-propyl chloride, n-propyl fluoride, n-propyl iodide and combinations thereof.

The process of embodiments may result in chirally purified 2-amino-4,5,6,7-tetrahydro-6-(propylamino)benzothiazole that is at least greater than about 97% chirally pure. In some embodiments, the chirally purified 2-amino-4,5,6,7-tetrahydro-6-(propylamino)benzothiazole may be at least greater than about 99% chirally pure, and in other embodiments, the chirally purified 2-amino-4,5,6,7-tetrahydro-6-(propylamino)benzothiazole may be at least about 99.9% chirally pure.

The chemical purity of the 2-amino-4,5,6,7-tetrahydro-6-(propylamino)benzothiazole of some embodiments may be greater than about. 99%. In certain embodiments, the chemical purity of the 2-amino-4,5,6,7-tetrahydro-6-(propylamino)benzothiazole may be greater than about 99.9%, and in certain other embodiments, the chemical purity of the 2-amino-4,5,6,7-tetrahydro-6-(propylamino)benzothiazole may be greater than about 99.99%.

In some embodiments, the 2,6 diamino-4,5,6,7-tetrahydro-benzothiazole may be (6R) 2,6 diamino-4,5,6,7-tetrahydro-benzothiazole and the chirally purified 2-amino-4,5,6,7-tetrahydro-6-(propylamino)benzothiazole may be (6R)-4,5,6,7-tetrahydro-N6-propyl-2,6-benzothiazole-diamine. In other embodiments, the 2,6 diamino-4,5,6,7-tetrahydro-benzothiazole may be (6S)-2,6 diamino-4,5,6,7-tetrahydro-benzothiazole and the chirally purified 2-amino-4,5,6,7-tetrahydro-6-(propylamino)benzothiazole may be (6S)-4,5,6,7-tetrahydro-N6-propyl-2,6-benzothiazole-diamine. In still other embodiments, the 2,6 diamino-4,5,6,7-tetrahydro-benzothiazole may be a mixture of (6R)-2,6 diamino-4,5,6,7-tetrahydro-benzothiazole and (6S)-2,6 diamino-4,5,6,7-tetrahydro-benzothiazole and the chirally purified 2-amino-4,5,6,7-tetrahydro-6-(propylamino)benzothiazole may be a mixture of (6R)-4,5,6,7-tetrahydro-N6-propyl-2,6-benzothiazole-diamine and (6S)-4,5,6,7-tetrahydro-N6-propyl-2,6-benzothiazole-diamine. In certain embodiments, the mixture is a racemic mixture. In other embodiments, the mixture may be a ratio of greater than about 1:4 (6R)-2,6 diamino-4,5,6,7-tetrahydro-benzothiazole and (6S)-2,6 diamino-4,5,6,7-tetrahydro-benzothiazole to about 4:1 (6R)-2,6 diamino-4,5,6,7-tetrahydro-benzothiazole and (6S)-2,6 diamino-4,5,6,7-tetrahydro-benzothiazole.

The organic solvent of embodiments may be selected from an organic solvent and an organic solvent is mixed with water, and in some embodiments, the organic solvent may be selected from ethanol, 1-propanol, n-butanol, dihydrofuran, dimethylformamide, dimethyl, dimethylacetamide, hexamethylphosphoric triamide or mixtures or hydrates thereof.

In various embodiments, the steps of heating, adding and reacting each independently may include stirring, and in some embodiments, the steps of heating, adding and reacting may each independently be carried out at a temperature of from about 50° C. to about 125° C. In certain embodiment, the process may further include the step of cooling the reaction mixture to a temperature of about 25° C. after the step of reacting. In some embodiments, about 1.0 to about 2.0 molar equivalents of the propyl sulfonate or propyl halide may be added, and the step of adding in particular embodiments may be carried out for up to about 2 hours. In still other embodiments, the process may include the step of recovering the chirally purified 2-amino-4,5,6,7-tetrahydro-6-(propylamino)benzothiazole, and in some embodiments, recovering may include one or more steps selected from filtering the mixture to isolate a precipitate, washing a precipitate, and drying a precipitate.

Embodiments of the invention further include a process for preparing chirally purified 2-amino-4,5,6,7-tetrahydro-6-(propylamino)benzothiazole including the steps of heating a solution comprising 2,6 diamino-4,5,6,7-tetrahydro-benzothiazole; adding a propyl halide or a propyl sulfonate to the heated solution slowly over from about 0.5 hours to about 2 hours to form a reaction mixture; reacting the reaction mixture; and recovering the chirally purified 2-amino-4,5,6,7-tetrahydro-6-(propylamino)benzothiazole.

In some embodiments, the chirally purified 2-amino-4,5,6,7-tetrahydro-6-(propylamino)benzothiazole may be at least greater than about 97% chirally pure. In other embodiments, the chirally purified 2-amino-4,5,6,7-tetrahydro-6-(propylamino)benzothiazole may be at least greater than about 99% chirally pure, and in certain embodiments, the chirally purified 2-amino-4,5,6,7-tetrahydro-6-(propylamino)benzothiazole is at least about 99.9% chirally pure.

The chemical purity of the 2-amino-4,5,6,7-tetrahydro-6-(propylamino)benzothiazole of various embodiments may be greater than about. 99%. In some embodiments, the chemical purity of the 2-amino-4,5,6,7-tetrahydro-6-(propylamino)benzothiazole may be greater than about 99.9%, and in particular embodiments, the chemical purity of the 2-amino-4,5,6,7-tetrahydro-6-(propylamino)benzothiazole is greater than about 99.99%.

In some embodiments, the 2,6 diamino-4,5,6,7-tetrahydro-benzothiazole may be (6R)-2,6 diamino-4,5,6,7-tetrahydro-benzothiazole and the chirally purified 2-amino-4,5,6,7-tetrahydro-6-(propylamino)benzothiazole may be (6R)-4,5,6,7-tetrahydro-N6-propyl-2,6-benzothiazole-diamine. In other embodiments, the 2,6 diamino-4,5,6,7-tetrahydro-benzothiazole is (6S)-2,6 diamino-4,5,6,7-tetrahydro-benzothiazole and the chirally purified 2-amino-4,5,6,7-tetrahydro-6-(propylamino)benzothiazole is (6S)-4,5,6,7-tetrahydro-N6-propyl-2,6-benzothiazole-diamine. In certain embodiments, the 2,6 diamino-4,5,6,7-tetrahydrobenzothiazole may be a mixture of (6R)-2,6 diamino-4,5,6,7-tetrahydro-benzothiazole and (6S)-2,6 diamino-4,5,6,7-tetrahydro-benzothiazole and the chirally purified 2-amino-4,5,6,7-tetrahydro-6-(propylamino)benzothiazole may be a mixture of (6R)-4,5,6,7-tetrahydro-N6-propyl-2,6-benzothiazole-diamine and (6S)-4,5,6,7-tetrahydro-N6-propyl-2,6-benzothiazole-diamine. In some such embodiments, the mixture may be a racemic mixture. In other such embodiments, the mixture may be a ratio of greater than about 1:4 (6R)-2,6 diamino-4,5,6,7-tetrahydro-benzothiazole and (6S)-2,6 diamino-4,5,6,7-tetrahydro-benzothiazole to about 4:1 (6R)-2,6 diamino-4,5,6,7-tetrahydro-benzothiazole and (6S)-2,6 diamino-4,5,6,7-tetrahydro-benzothiazole.

In particular embodiments, the steps of heating, reacting and cooling each independently may include stirring. In other embodiments, the step of recovering may include cooling the mixture to a temperature of about 25° C., and in still other embodiments, the step of recovering may include stirring the reaction mixture for at least about 2 hours. In yet other embodiments, the step of recovering may further include one or more steps selected from filtering the mixture to isolate a precipitate, washing a precipitate, and drying a precipitate. In various embodiments, the steps of heating, adding and reacting may each independently be carried out at a temperature of from about 50° C. to about 125° C., and in certain embodiments, the step of reacting may include stirring the reaction mixture for up to about 12 hours at from about 50° C. to about 125° C.

Some embodiments of the invention include a chirally purified 2-amino-4,5,6,7-tetrahydro-6-(propylamino)benzothiazole prepared by a process including the steps of heating a solution comprising 2,6 diamino-4,5,6,7-tetrahydro-benzothiazole; adding a propyl halide or a propyl sulfonate to the heated solution slowly over from about 0.5 hours to about 2 hours to form a reaction mixture; reacting the reaction mixture; and recovering the chirally purified 2-amino-4,5,6,7-tetrahydro-6-(propylamino)benzothiazole.

In some embodiments, the propyl sulfonate is selected from n-propyl tosylate, n-propyl methoxysulfonate and combinations thereof, and in other embodiments, the propyl halide is selected from n-propyl bromide, n-propyl chloride, n-propyl fluoride, n-propyl iodide and combinations thereof.

In various embodiments, the chirally purified 2-amino-4,5,6,7-tetrahydro-6-(propylamino)benzothiazole may at least greater than about 97% chirally pure. In some embodiments, the chirally purified 2-amino-4,5,6,7-tetrahydro-6-(propylamino)benzothiazole may be at least greater than about 99% chirally pure, and in other embodiments, the chirally purified 2-amino-4,5,6,7-tetrahydro-6-(propylamino)benzothiazole is at least about 99.9% chirally pure.

In various other embodiments, the chemical purity of the 2-amino-4,5,6,7-tetrahydro-6-(propylamino)benzothiazole may be greater than about 99%. In some embodiments, the chemical purity of the 2-amino-4,5,6,7-tetrahydro-6-(propylamino)benzothiazole may be greater than about 99.9%, and in other embodiments, the chemical purity of the 2-amino-4,5,6,7-tetrahydro-6-(propylamino)benzothiazole is greater than about 99.99%.

In some embodiments, the 2,6 diamino-4,5,6,7-tetrahydro-benzothiazole may be a mixture of (6R)-2,6 diamino-4,5,6,7-tetrahydro-benzothiazole and (6S)-2,6 diamino-4,5,6,7-tetrahydro-benzothiazole and the chirally purified 2-amino-4,5,6,7-tetrahydro-6-(propylamino)benzothiazole may be a mixture of (6R)-4,5,6,7-tetrahydro-N6-propyl-2,6-benzothiazole-diamine and (6S) 2-amino-4,5,6,7-tetrahydro-6-(propylamino)benzothiazole. In certain embodiments, the mixture may be a racemic mixture. In other embodiments, the mixture may be a ratio of greater than about 4:1 (6R)-2,6 diamino-4,5,6,7-tetrahydro-benzothiazole and (6S)-2,6 diamino-4,5,6,7-tetrahydro-benzothiazole.

The organic solvent of various embodiments may be selected from a. organic solvent and an organic solvent is mixed with water, and the organic solvent of some embodiments may be selected from ethanol, 1-propanol, n-butanol, dihydrofuran, dimethylformamide, dimethyl, dimethylacetamide, hexamethyiphosphoric triamide or mixtures or hydrates thereof.

In particular embodiments, the steps of heating, reacting and cooling each independently may include stirring, and in some embodiments, the steps of heating, adding and reacting are each independently carried out at a temperature of from about 50° C. to about 125° C. In other embodiments, the process may further include cooling the reaction mixture to a temperature of about 25° C. after the step of reacting, and in still other embodiments, the step of adding is carried out for up to about 2 hours. In certain embodiments, the step of recovering may include one or more steps selected from filtering the mixture to isolate a precipitate, washing a precipitate, and drying a precipitate. In various embodiments, about 1.0 to about 2.0 molar equivalents of the propyl sulfonate or propyl halide may be added.

Yet other embodiments of the invention include a process for preparing chirally purified 2-amino-4,5,6,7-tetrahydro-6-(propylamino)benzothiazole including the steps of dissolving entantiomerically enriched 2-amino-4,5,6,7-tetrahydro-6-(propylamino)benzothiazole in an organic solvent to form a solution; heating the solution to from about 50° C. to about 125° C.; adding an acid to the solution to form a reaction mixture; and recovering the chirally purified 2-amino-4,5,6,7-tetrahydro-6-(propylamino)benzothiazole.

In some embodiments, about 1 molar equivalent to about 4 molar equivalents of the acid may be added. In other embodiments, recovering may include one or more steps including cooling the reaction mixture to a temperature of about 25° C.; stirring the reaction mixture for at least about 2 hours; filtering the mixture to isolate a precipitate; washing a precipitate; and drying a precipitate.

Further embodiments of the invention include a chirally pure 2-amino-4,5,6,7-tetrahydro-6-(propylamino)benzothiazole prepared by such a process.

Still other embodiments of the invention include a process for preparing chirally purified 2-amino-4,5,6,7-tetrahydro-6-(propylamino)benzothiazole including the steps of dissolving entantiomerically enriched 2-amino-4,5,6,7-tetrahydro-6-(propylamino)benzothiazole in an organic solvent to form a solution; heating the solution to from about 50° C. to about 125° C.; adding an achiral salt to the solution to form a reaction mixture; and recovering the chirally purified 2-amino-4,5,6,7-tetrahydro-6-(propylamino)benzothiazole.

In some embodiments, about 1 molar equivalent to about 4 molar equivalents of the achiral salt is added. In other embodiments, the step of recovering may include one or more steps selected from cooling the reaction mixture to a temperature of about 25° C.; stirring the reaction mixture for at least about 2 hours; filtering the mixture to isolate a precipitate; washing a precipitate; and drying a precipitate.

Further embodiments of the invention include a chirally pure 2-amino-4,5,6,7-tetrahydro-6-(propylamino)benzothiazole prepared by a such a process.

Still further embodiments of the invention include a process for preparing a 2-amino-4,5,6,7-tetrahydro-6-(propyla.mino)benzothiazole dihydrochloride comprising dissolving a 2-amino-4,5,6,7-tetrahydro-6-(propylamino)benzothiazole salt in an organic solvent to form a solution; cooling the solution to a temperature of from about 0° C. to about 5° C.; adding concentrated HCl and an organic solvent to the cooled solution; and stirring the solution at a temperature of about 0° C. to about 5° C.

DESCRIPTION OF DRAWINGS

For a fuller understanding of the nature and advantages of the present invention, reference should be made to the following detailed description taken in connection with the accompanying drawings, in which.

DETAILED DESCRIPTION

Figure 1A:
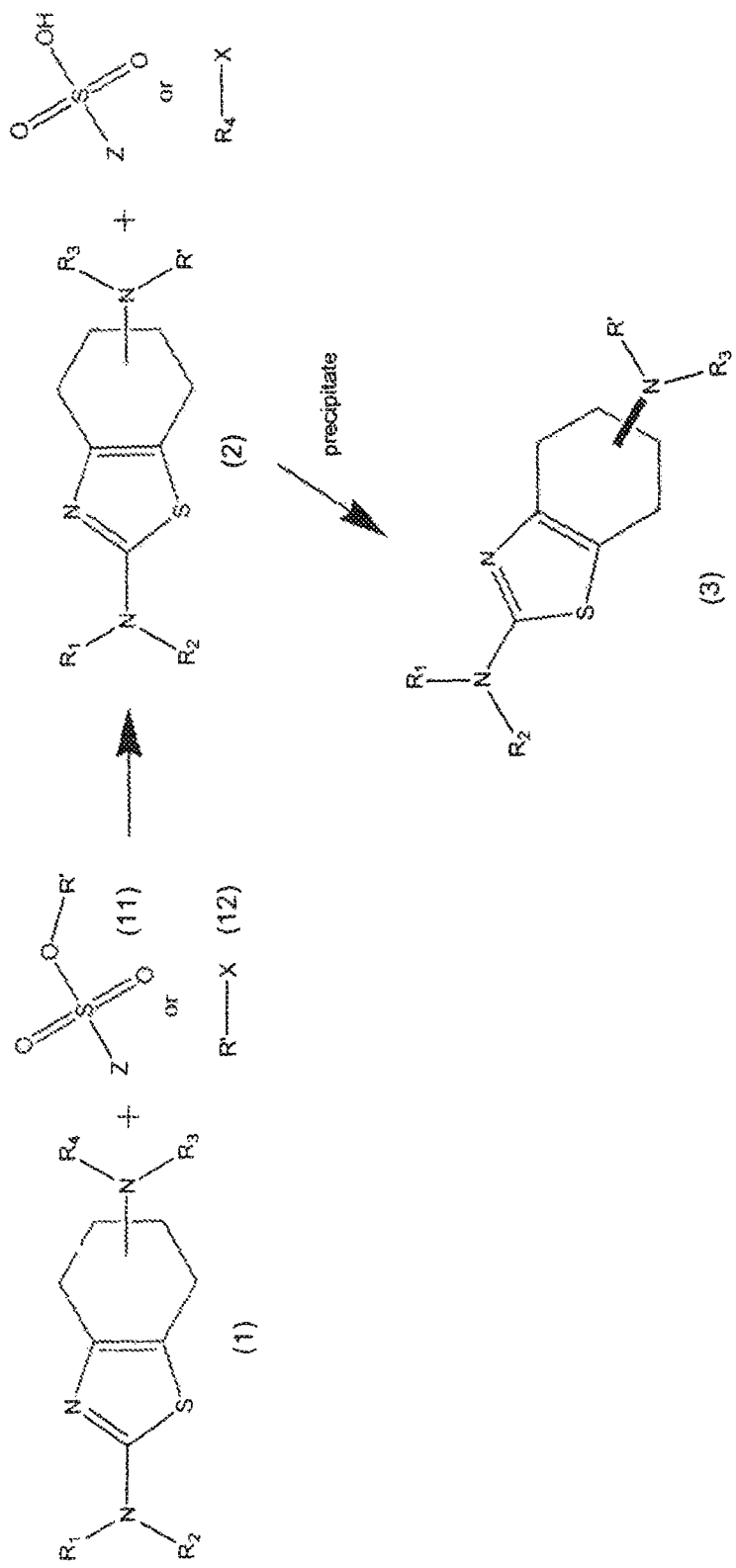
FIG. 1A shows a reaction scheme illustrating the alkylation of 4,5,6,7-tetrahydro-benzothiazole diamine.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must be noted that, as used herein, and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes instances where the event occurs and instances where it does not.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by oral administration, injection, infusion, absorption or by any method in combination with other known techniques. Such combination techniques include heating, radiation and ultrasound.

The term "target", as used herein, refers to the material for which either deactivation, rupture, disruption or destruction or preservation, maintenance, restoration or improvement of function or state is desired. For example, diseased cells, pathogens, or infectious material may be considered undesirable material in a diseased subject and may be a target for therapy.

Generally speaking, the term "tissue" refers to any aggregation of similarly specialized cells which are united in the performance of a particular function.

The term "improves" is used to convey that the present invention changes either the appearance, form, characteristics and/or physical attributes of the tissue to which it is being provided, applied or administered. "Improves" may also refer to the overall physical state of an individual to whom an active agent has been administered. For example, the overall physical state of an individual may "improve" if one or more symptoms of a neurodegenerative disorder are alleviated by administration of an active agent.

As used herein, the term "therapeutic" means an agent utilized to treat, combat, ameliorate or prevent an unwanted condition or disease of a patient.

The terms "therapeutically effective amount" or "therapeutic dose" as used herein are interchangeable and may refer to the amount of an active agent or pharmaceutical compound or composition that elicits a biological or medicinal response in a tissue, system, animal, individual or human that is being sought by a researcher, veterinarian, medical doctor or other clinician. A biological or medicinal response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experienced or exhibited by the individual.

As used herein, the term "neuroprotectant" refers to any agent that may prevent, ameliorate or slow the progression of neuronal degeneration and/or neuronal cell death.

The term "treating" may be taken to mean prophylaxis of a specific disorder, disease or condition, alleviation of the symptoms associated with a specific disorder, disease or condition and/or prevention of the symptoms associated with a specific disorder, disease or condition.

The term "patient" generally refers to any living organism to which to compounds described herein are administered and may include, but is not limited to, any non-human mammal, primate or human. Such "patients" may or my not be exhibiting the signs, symptoms or pathology of the particular diseased state.

As used herein, the terms "enantiomers", "stereoisomers" and "optical isomers" may be used interchangeably and refer to molecules which contain an asymmetric or chiral center and are mirror images of one another. Further, the terms "enantiomers", "stereoisomers" or "optical isomers" describe a molecule which, in a given configuration, cannot be superimposed on, its mirror image.

As used herein, the terms "optically pure" or "entantiomerically pure" may be taken to indicate that a composition contains at least 99.95% of a single optical isomer of a compound. The term "entantiomerically enriched" may be taken to indicate that at least 51% of a composition is a single optical isomer or enantiomer. The term "entantiomeric enrichment" as used herein refers to an increase in the amount of one entantiomer as compared to the other. A "racemic" mixture is a mixture of equal amounts of (6R) and (6S) enantiomers of a chiral molecule.

Throughout this disclosure, the word "pramipexole" will refer to (6S) enantiomer of 2-amino-4,5,6,7-tetrahydro-6-(propylamino)benzothiazole unless otherwise specified.

The term "trituration" may be taken to indicate a method of solidifying a chemical compound. Trituration involves agitating the compound by stirring, beating or a method of the like until the chemical compound forms a crystalline solid or precipitate. This solid may act to seed the remaining chemical compound in solution, causing it to precipitate or crystallize from solution.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain (6S)-4,5,6,7-tetrahydro-N6-propyl-2,6-benzothiazole-diamine or a pharmaceutically acceptable salt of (6S)-4,5,6,7-tetrahydro-N6-propyl-2,6-benzothiazole-diamine as the active ingredient. Alternatively, a pharmaceutical composition may contain (6R)-4,5,6,7-tetrahydro-N6-propyl-2,6-benzothiazole-diamine or a pharmaceutically acceptable salt of (6R)-4,5,6,7-tetrahydro-N6-propyl-2,6-benzothiazole-diamine as the active ingredient.

For the purposes of this disclosure, a "salt" is any acid addition salt, preferably a pharmaceutically acceptable acid addition salt, including but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, describes pharmaceutically acceptable salts in detail.

Embodiments of the invention described herein are generally directed to processes for the production of an entantiomerically and/or chemically pure compound. More, specifically, embodiments of the invention are directed to production of an entantiomerically and/or chemically pure compound using a trituration step where one enantiomer of an entantiomeric mixture of R and S stereoisomers of a compound is precipitated out of solution and can be isolated by, for example, simple filtering or other means for separating a solid or crystalline compound from a solution.

For example, embodiments of the invention include a method for preparation of an entantiomerically and chemically pure compound using a one-pot bi-molecular nucleophilic substitution ($S_N2$) reaction synthesis method as illustrated in the reaction scheme provided in FIG. 1A. In FIG.

1A, a 4,5,6,7-tetrahydro-benzothiazole diamine (1) is reacted with an alkyl sulfonate (11) or an alkyl halide (12), exemplified by n-propyl sulfonate or propyl halide, to generate an aminoalkyl containing compound of a 4,5,6,7-tetrahydro-benzothiazole diainine (2), and a sulfonate or halide salt. In a trituration step, one enantiomer of the 4,5,6,7-tetrahydro-benzothiazole diamine, for example, (R) (+)-4,5,6,7-tetrahydro-benzothiazole diamine (3), is precipitated based on insolubility of the enantiomers in the achiral halide or sulfonate salts produced as a result of the reaction and can be isolated. The other enantiomer remains in solution.

Figure 1B:
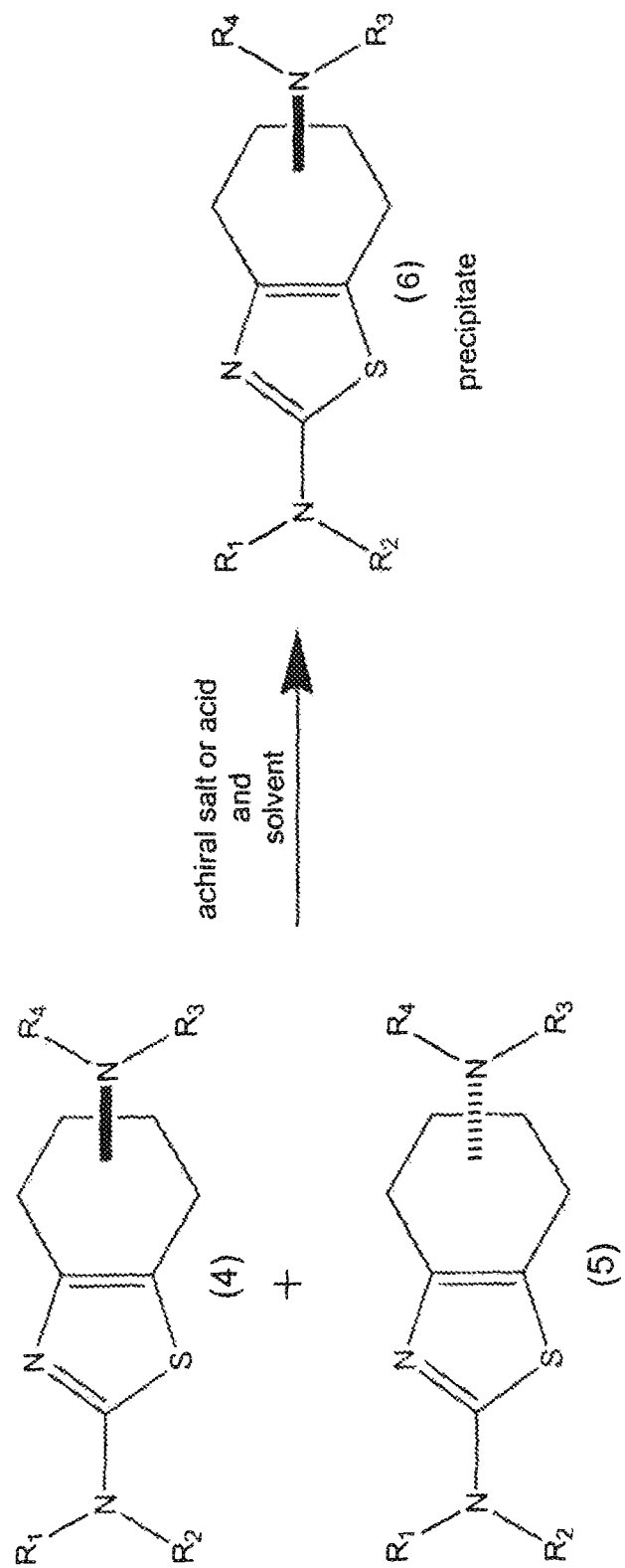
FIG. 1B shows a reaction scheme illustrating the entantiomeric purification of one 4,5,6,7-tetrahydro-benzothiazole diamine from an entantiomeric mixture of 4,5,6,7-tetrahydro-benzothiazole diamines.

In another exemplary embodiment illustrated in FIG. 1B, chirally pure compounds, such as, (6R) 4,5,6,7-tetrahydro-benzothiazole diamine (3), may be prepared from a mixture of R and S enantiomers of a compound, such as, for example, (6R) 4,5,6,7-tetrahydro-benzothiazole diamine (4) and (6S) 4,5,6,7-tetrahydro-benzothiazole diamine (5). In this process, trituration may result from the addition of an organic solvent and an achiral salt or acid to the mixture which may cause the formation of an acid addition salt of one enantiomer. The salt, (6R) 4,5,6,7-tetrahydro-benzothiazole diarnine (3), precipitates out of the solution based on insolubility of the enantiomers in the resulting solution while the other enantiomer remains in solution. The precipitated crystalline enantiomer may then be isolated.

The reaction illustrated in FIG. 1A is not limited to a particular 4,5,6,7-tetrahydro-benzothiazole diamine. For example, the 4,5,6,7-tetrahydro-benzothiazole diamine may be any 4,5,6,7-tetrahydro-benzothiazole diamine of formula (1):

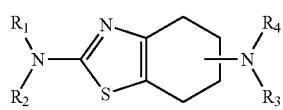

(1)

wherein:
$R_1$ represents a hydrogen atom, an alkyl group having 1 to 6 carbon atoms, an alkenyl or alkynyl group each having 3 to 6 carbon atoms, an alkanoyl group having 1 to 6 carbon atoms, a phenyl alkyl or phenyl alkanoyl group having 1 to 3 carbon atoms in the alkyl part, whilst the above-mentioned phenyl nuclei may be substituted by 1 or 2 halogen atoms;
$R_2$ represents a hydrogen atom or an alkyl group with 1 to 4 carbon atoms;
$R_3$ represents a hydrogen atom, an alkyl group with 1 to 7 carbon atoms, a cycloalkyl group having 3 to 7 carbon atoms, an alkenyl or alkynyl group having 3 to 6 carbon atoms, an alkanoyl group having 1 to 7 carbon atoms, a phenyl alkyl or phenyl alkanoyl group having 1 to 3 carbon atoms in the alkyl part, whilst the phenyl nucleus may be substituted by fluorine, chlorine or bromine atoms,
$R_4$ represents a hydrogen atom, an alkyl group with 1 to 4 carbon atoms, an alkenyl or alkynyl group having 3. to 6 carbon atoms;
and at least one or $R_1$, $R_2$, $R_3$ or $R_4$ is a hydrogen.
The 4,5,6,7-tetrahydro-benzothiazole diamine of formula 1 encompasses all enantiomers at any chiral center on the molecule.

The reaction illustrated in FIG. 1A is not limited by the type of alkyl halide or alkyl sulfonate utilized in the reaction. For example, the alkyl sulfonates may be any alkyl sulfonate of formula (11):

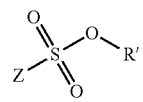

(11)

wherein:
R' is an alkyl group having 1 to 6 carbons, or a cycloalkyl, alkenyl, alkynyl, allyl, having 1 to 10 carbon atoms, or a benzyl, chlorobenzyl, phenyl, phenyl alkyl and the like; and
Z is an alkyl group having 1 to 6 carbons, or a cycloalkyl, alkenyl, alkynyl, allyl, having 1 to 10 carbon atoms, or a benzyl, chlorobenzyl, phenyl, phenyl alkyl and the like; and the alkyl halide may be any alkyl halide of formula (12):

R'—X (12)

wherein
R' is an alkyl group having 1 to 6 carbons, or a cycloalkyl, alkenyl, alkynyl, allyl, having 1 to 10 carbon atoms, or a benzyl, chlorobenzyl, phenyl, phenyl alkyl and the like; and
X is any halide including, for example, chlorine, bromine or iodide.
In various embodiments, R' is an alkyl and, in particular embodiments, an n-propyl. In certain embodiments where alkyl sulfonate, the Z moiety may be toluenesulfonate (tosylate) or methoxysulfonate. For example, in various embodiments, the alkyl sulfonate may be n-propyl tosylate. In embodiments in which an alkyl halide is used, the alkyl halide may be n-propyl bromide or n-propyl chloride. In general, the alkyl sulfonate or alkyl halide may be added in a. quantity corresponding to about 1.0 to about 4.0 molar equivalents of the diamine.

Advantages of embodiments such as those described above may include, for example, (1) the use of simple reagents for the synthesis and purification of one enantiomer enantiomeric compounds, (2) the surprising improvement of the optical and chemical purity achieved by simple trituration, and (3) such processes may be performed as a one-pot synthesis and purification reactions. When taken as a whole, the processes described above may be simpler, safer, and more efficient for the production of chirally and chemically pure compounds. Additionally, the compounds may be sufficiently chirally and chemically pure to make such compounds safe an effective for use in pharmaceutical compounds and in the treatment of disease.

While the methods provided above may be used to purify any enantiomeric compound known in the art, particular embodiments of the invention are directed to the production and optical purification of 2-amino-4,5,6,7-tetrahydro-6-(propylamino)benzothiazole and, in particular, (6R)-4,5,6, 7-tetrahydro-N6-propyl-2,6-benzothiazole-diamine. The extremely high chiral and chemical purity of the compound produced by methods of the present invention allow for pharmaceutical compositions that may have a wide individual and daily dose range. For example, in some embodiments, (6R)-4,5,6,7-tetrahydro-N6-propyl-2,6-benzothiazole-diamine produced using methods embodied herein may be nearly 100% chirally pure. Such compositions include little to no (6S)-4,5,6,7-tetrahydro-N6-propyl-2,6-benzothiazole-diamine contamination and may be administered at high doses without the risk of the dopaminergic side effects associated with administration of high dose (6S)-4,5,6,7-tetrahydro-N6-propyl-2,6-benzothiazole-diamine. The compositions of (6R)-4,5,6,7-tetrahydro-N6-propyl-2,6-benzothiazole-diamine may therefore be used to treat neurodegenerative diseases, or those associated with mitochondrial dysfunction or increased oxidative stress such as, for example, neurodegenerative dementias, neurodegenerative movement disorders and ataxias, seizure disorders, motor neuron disorders or diseases, inflammatory demyelinating disorders and the like in adults and children. The compositions of this disclosure may also be useful in the treatment of other disorders not listed herein, and any listing provided in this disclosure is for exemplary purposes only and is non-limiting.

Compositions and pharmaceutical compositions comprising entantiomerically pure (6R)-4,5,6,7-tetrahydro-N6-propyl-2,6-benzothiazole-diamine, such as those discussed above, are further disclosed in U.S. application Ser. No. 11/773,642 entitled "Tetrahydrobenzothiazoles and Uses Thereof" filed Apr. 10, 2007, U.S. application Ser. No. 11/957,157 entitled "Compositions and Methods of Using R(+) Pramipexole", filed Dec. 14, 2007 and U.S. application Ser. No. 11/749,497 entitled "Pramipexole Formulations for the Treatment of Parkinson's Disease", filed on May 16, 2007, each of which are hereby incorporated by reference in their entireties. Although any methods and materials similar or equivalent to those described herein can be used in the practice or testing of embodiments of the present invention, the preferred methods, devices, and materials are described in detail herein.

Figure 2:
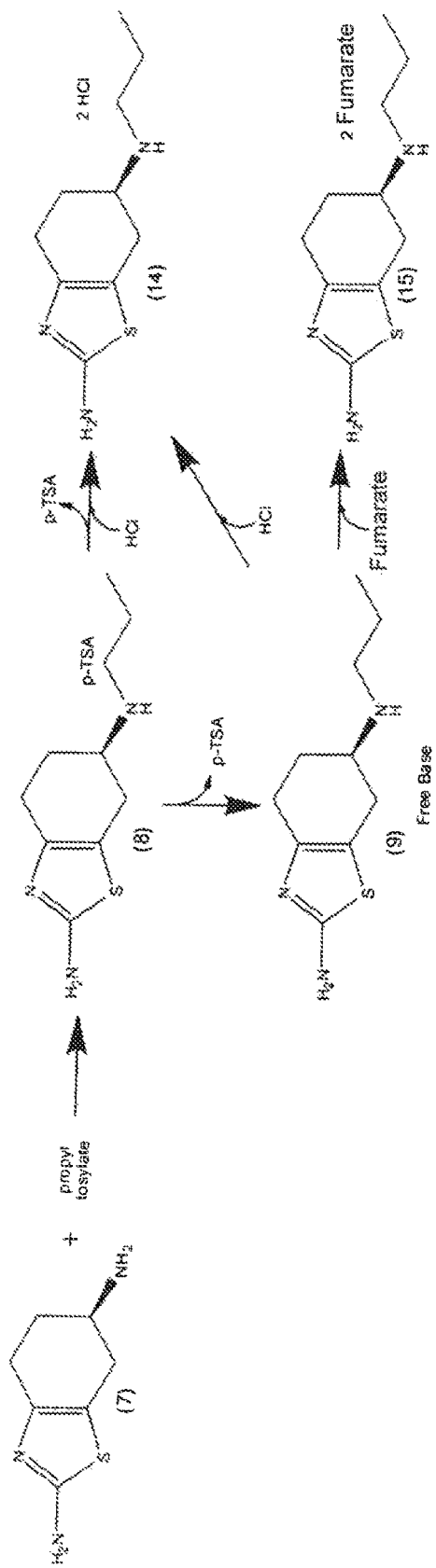
FIG. 2 shows a reaction scheme illustrating the preparation of (6R)-4,5,6,7-tetrahydro-N6-propyl-2,6-benzothiazole-diamine-dihydrochloride and (6R)-4,5,6,7-tetrahydroN6-propyl -2, 6-b enzothiazole-diamine difumarate.

Production of either enantiomer, (6R) or (6S)-4,5,6,7-tetrahydro-N6-propyl-2,6-benzothiazole-diamine may be carried using the bi-molecular nucleophilic substitution ($S_N2$) reaction described above and optical purification based on insolubility of the compound product in achiral reagents. More specifically, FIG. 2 schematically illustrates an embodiment of the process for the production of entantiomerically and chemically pure 2-amino-4,5,6,7-tetrahydro-6-(propylamino)benzothiazole using a bi-molecular nucleophilic substitution ($S_N2$) reaction. In a. first step, 2,6 diamino-4,5,6,7-tetrahydro-benzothiazole (7) is mixed propyl p-toluenesulfonate (propyl tosylate), and reacted to produce 2-amino-4,5,6,7-tetrahydro-6-(propylamino)benzothiazole (8) and 4-methylbenzenesulfonic acid (p-toluenesulfonic acid, p-TSA). Without wishing to be bound by theory, the diamine, 2,6 diamino-4,5,6,7-tetrahydro-benzothiazole (7), in the reaction scheme of FIG. 2 may act as the nucleophile in a nucleophilic attack on the substrate, a propyl tosylate, and the tosylate group may provide a good leaving group as depicted below:

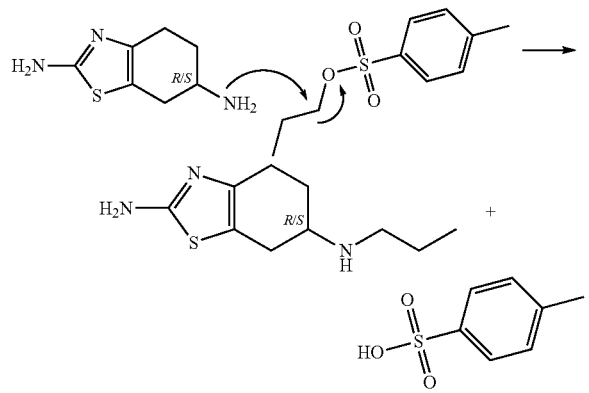

Thus, an embodiment of the invention is a process for preparing a 2-amino-4,5,6,7-tetrahydro-6-(propylamino) benzothiazole salt (8) by a bimolecular nucleophilic substitution reaction. In a second step, the 2-amino-4,5,6,7-tetrahydro-6-(propylamino)benzothiazole (8) may be entantiomerically purified by allowing the 2-amino-4,5,6,7-tetrahydro-6-(propylamino)benzothiazole (8) to precipitate out of the reaction solution without the addition of any secondary agents, such as, for example, additional salt. Thus, entantiomerically pure 2-amino-4,5,6,7-tetrahydro-6-(propylamino)benzothiawle may be isolated in a third step by simply filtering out the 2-amino-4,5,6,7-tetrahydro-6-(propylamino)benzothiazole crystals.

Some embodiments of methods of the invention may include additional steps. For example, in some embodiments, p-TSA may be removed to form the entantiomerically purified 2-amino-4,5,6,7-tetrahydro-6-(propylamino) benzothiazole (8) to form a 2-amino-4,5,6,7-tetrahydro-6-(propylamino)benzothiazole free base (9) and hydrochloric acid or fumaric acid may be added to the free base to form 2-amino-4,5,6,7-tetrahydro-6-(propylamino)benzothiazole-dihydrochloride (14) or 2-amino-4,5,6,7-tetrahydro-6-(propylamino)benzothiazole difumarate (15). In other embodiments, 2-amino-4,5,6,7-tetrahydro-6-(propylamino) benzothiazole-dihydrochloride (14) may be produced by adding hydrochloric acid to the entantiomerically purified 2-amino-4,5,6,7-tetrahydro-6-(propylamino)benzothiazole (8).

While the reaction scheme illustrated in FIG. 2, shows the production of (6R)-4,5,6,7-tetrahydro-N6-propyl-2,6-benzothiazole-diamine from (6R)-2,6 diamino-4,5,6,7-tetrahydro-benzothiazole, in some embodiments, the same reaction may be carried out using (6S)-2,6 diamino-4,5,6,7-tetrahydro-benzothiazole to produce (6S)-4,5,6,7-tetrahydro-N6-propyl-2,6-benzothiazole-diamine. In other embodiments, a mixture of (6R) and (6S)-4,5,6,7-tetrahydro-N6-propyl-2,6-benzothiazole-diamine may be used as starting material which may result in a mixture of (6R) and (6S)-4,5,6,7-tetrahydro-N6-propyl-2,6-benzothiazole-diamine. In particular embodiments, a mixture of (6R) and (6S)-2,6 diamino-4,5,6,7-tetrahydro -benzothiazole that is entantiomerically enriched for one entantiomer may be used as starting material. Additionally, the reaction illustrated in FIG. 2 may be carried out with an n-propyl halide or a mixture of n-propyl halide and n-propyl sulfonate.

In some embodiments, step one of the process may include the additional steps of heating a diamine to form a solution or melt in a heating step and adding the n-propyl halide or n-propyl sulfonate slowly over a period of time from, for example, about 0.5 hours to about 5 hours, in an additional step. In other embodiments, after the n-propyl halide or n-propyl sulfonate has been completely added to the 2,6 diamino-4,5,6,7-tetrahydro-benzothiazole, the reaction may continue under heating for an additional period of time ranging from, for example, about 1 hour to about 12 hours, in a reaction step. In certain embodiments, the reaction mixture may be mixed by, for example, stirring for one or more of the steps above or the reaction mixture may be continually stirred from the heating step to the reaction step. Following the reaction step, the reaction mixture may be cooled and the 2-amino-4,5,6,7-tetrahydro-6-(propylamino) benzothiazole may be isolated and purified.

In embodiments such as those exemplified above, the diamine, 2,6 diamino-4,5,6,7-tetrahydro-benzothiazole, may be a racemic mixture or entantiomerically enriched for either the S or R enantiomer, and the 2-amino-4,5,6,7-tetrahydro-6-(propylamino)benzothiawle produced may be generally optically enriched for the dominant enantiomer. For example, (6R) 2,6 diamino-4,5,6,7-tetrahydro-benzothiazole may be the dominant enantiomer in mixtures used as a starting material in reaction that produces (6R)-4,5,6,7-tetrahydro-N6-propyl-2,6-benzothiazole-diamine. In various embodiments, any R to S ratio of diamine may be used. For example, in some embodiments, the diamine may be in a racemic mixture (i.e., R:S is about 50:50), and in such embodiments, the yield of the reaction would be expected to be a racemic mixture of (6R)-4,5,6,7-tetrahydro-N6-propyl-2,6-benzothiazole-diamine and (6S)-4,5,6,7-tetrahydro-N6-propyl-2,6-benzothiazole-diamine (i.e., about 50:50). In other embodiments, the diamine may be provided in a mixture in which one stereoisomer is in excess over the other; for example, R:S may be about 60:40. In such embodiments, the reaction would be expected to yield a mixture of (6R)-4,5,6,7-tetrahydro-N6-propyl-2,6-benzothiazole-diamine and (6S)-4,5,6,7-tetrahydro-N6-propyl-2,6-benzothiazole-diamine that is about 60:40 R to S.

The reaction may be carried out in a melt or in a solvent or mixture of solvents, and the methods embodied herein are not limited by the type or number of solvents present during the reaction. Any solvent or mixture of solvents known in the art in which the diamine and alkyl halide or alkyl sulfonate can dissolved may be used. For example, in various embodiments, the solvents may be, for example, tetrahydrofuran, dimethylformamide, dimethly sulfoxide, dimethylacetamide, hexamethylohosphoric triamide, glacial acetic acid, pyridine, dioxan, ethanol, 1-propanol, i-propanol, n-butanol, i-butanol, or combinations thereof, for example, dioxan/water, ethanol/water, tetrahydrofuran/water and the like. In embodiments in which a combination of an organic solvent and water are used, the organic solvent may have a water content of from about 0 to about 10 volume percent. Preferably, the solvents used in the practice of this invention are standard ACS grade solvents. The selection of a solvent may enhance the reaction rate of the $S_N2$ reaction. In some embodiments, one or more base such as, for example, sodium hydroxide, sodium hydride, potassium carbonate, sodium acetate, potassium-tertbutyloxide, triethylamine, di-isoprolyethylamine and the like, may be additionally added to the reaction mixture which may further enhance the efficiency of the reaction. When added, a base may be present in a concentration of about 0.5 to about 3.0 equivalents based on the solvent. In still other embodiments, an alkylating agent may be provided in the melt or solvent. Alkylating agents are well known in the art and may be useful in embodiments of the invention. For example, alkylating agents may include, but not limited to, methyliodide, dimethylsulfate, ethylbromide, diethylsulfate, allyliodide, benzylbromide, 2-phenylethylbromide and methyl-p-toluenesulfonate.

In general, the reaction may be carried out under ambient conditions. However, the reaction temperature may vary among embodiments from between about −10° C. to about 50° C. and, in particular embodiments, from 0° C. to 30° C.

In further embodiments, dissolved diamine may be heated and mixed or stirred during the reaction. For example, various embodiments include the step of heating a dissolved diamine, adding a n-propyl sulfonate or n-propyl halide which may, in some embodiments, be dissolved in a solvent to form a mixture, and stirring the mixture. In other embodiments, a base such as di-isoproplyethylamine may be added to a solution including a diamine. N-propyl sulfonate or n-propyl halide may be' dissolved in a solvent, and then added to the diamine/di-isoproplyethylamine solution and this reaction mixture may be stirred. The temperature of reactions of such embodiments may; generally, be below the boiling temperature of the reaction mixture, more specifically, below the boiling temperature of the solvent(s) of the reaction mixture. For example, in some embodiments, an elevated temperature may be lower than about 125° C. In others, an elevated temperature may be lower than about 100° C., and in yet another embodiment lower than about 95° C., and in still others less than about 75° C. Therefore, the reaction temperature may range from about 50° C. to about 125° C. in some embodiments, about 55° C. to about 100° C. in other embodiments, about 60° C. to about 95° C. in still other embodiments, about 60° C. to about 75° C. in yet other embodiments and in certain embodiments, from about 55° C. to about 65° C.

The reaction time may vary within embodiments, and may depend upon, for example, the identities of the reactants, the solvent system and the chosen temperature. For example, in some embodiments, the reaction time may be from about 0.5 hours to. about 12 hours. In other embodiments, the reaction time may be from about 1 hour to about 8 hours, and in certain embodiments, the reaction time may be about 4 hours. In general, the reaction time is chosen to provide sufficient time for substantially all of the diamine to undergo alkylation. In particular embodiments, the reaction time further provides sufficient time for the 2-amino-4,5,6,7-tetrahydro-6-(propylamino)benzothiazole formed to precipitate out of the reaction solution and from visible crystals.

Embodiments of the invention may further include the step of cooling the reaction to a temperature about room temperature (25° C.) following the reaction. In such embodiments, the reaction may be cooled for any amount of time with or without continued stirring. For example, in some embodiments, the reaction may be cooled with stirring for about 0.5 to about 4 hours or more, and in other embodiments, the reaction may be cooled with stirring for about 2 hours.

More specific embodiments may include the steps of: dissolving a diamine in dimethylformamide; heating the dissolved diamine to an elevated temperature; adding the n-propyl sulfonate or n-propyl halide dissolved in dimethylformamide to form a reaction mixture; and stirring the reaction mixture for about 4 hours. In another embodiment, the steps may include dissolving a diamine in dimethylformamide, heating the dissolved diamine to an elevated temperature, slowly adding to the heated dissolved diamine 1.25 molar equivalents of n-propyl sulfonate or n-propyl halide dissolved in 10 volumes of dimethylformamide and 1.25 molar equivalents of di-isoproplyethylamine with stirring the reaction over a period of about 4 hours. In yet another embodiment, 1.25 molar equivalents of di-isoproplyethylamine may be added to a diamine dissolved in dimethylformamide and the n-propyl sulfonate or n-propyl halide dissolved in dimethylformamide may be added to this mixture with stirring for about 4 hours.

Following synthesis, entantiomerically pure isomers of 2-amino-4,5,6,7-tetrahydro-6-(propylamino)benzothiazole may be recovered using a trituration step in which the major isomer is isolated as a precipitated crystals, while the minor stereoisomer remains in solution. Without wishing to be bound by theory, insolubility of the 2-amino-4,5,6,7-tetrahydro-6-(propylamino)benzothiazole product in achiral reagents, such as p-TSA, may be independent of the R or S enantiomer, such that purity of the recovered isomer may depend only on the volume of the reaction solution and starting percentage of the major isomer. Thus, in an embodiment such as is described above, an entantiomerically pure (6R)-4,5,6,7-tetrahydro-N6-propyl-2,6-benzothiazole-diamine (R:S equals 100:0) yield may be produced from a reaction in which diamine is provided in an R to S ratio of 60:40.

An unexpected advantage of the process for preparing 2-amino-4,5,6,7-tetrahydro-6-(propylamino)benzothiazole described above is the limited solubility of the sulfonate or halide salt of 2-amino-4,5,6,7-tetrahydro-6-(propylamino) benzothiazole in polar organic solvents which causes the 2-amino-4,5,6,7-tetrahydro-6-(propylamino)benzothiazole product to precipitate once formed thereby purifying the final synthesis product, 2-amino-4,5,6,7-tetrahydro-6-(propylamino)benzothiazole, from the reaction mixture. In further embodiments, the substitution reaction such as that illustrated in FIG. 2 may result in a sufficient achiral salt, p-TSA, concentration to cause the 2-amino-4,5,6,7-tetrahydro-6-(propylamino)benzothiazole to become insoluble and crystallize in the reaction solution without adding additional agents, such as, for example, additional achiral salts.

The reaction embodied above and described in FIG. 2 may provide highly purified 2-amino-4,5,6,7-tetrahydro-6-(propylamino)benzothiazole in a one-pot synthesis method. For example, in embodiments of the process, the chemical purity of the final 2-amino-4,5,6,7-tetrahydro-6-(propylamino)benzothiazole prepared may be at least 97%, 98%, and up to 100% without additional purification steps, and in particular embodiments, the chemical purity may be from 99.90% to 100% without any additional purification steps. In still other embodiments, the final 2-amino-4,5,6,7-tetrahydro-6-(propylamino)benzothiazole may be substantially free of achiral salts such as, for example, p-TSA. For example, in some embodiments, the achiral salt concentration of the final synthesis product may be less than 3%, and in others the achiral salt concentration of the final synthesis product may be less than 1%, 0.5%, 0.1%, 0.01%, 0.001% and so on. In certain embodiments, the achiral salt concentration may be less than 1.5 ppm to less than 25 ppb or less than 0.00015% to less than 0.0000025%. Without wishing to be bound by theory, the ability to produce highly chemically pure 2-amino-4,5,6,7-tetrahydro-6-(propylamino)benzothiazole in a one-pot method may demonstrate a significant advancement in the production of 2-amino-4,5,6,7-tetrahydro-6-(propylamino)benzothiazole. Moreover, such purity may provide pharmaceutical grade 2-amino-4,5,6,7-tetrahydro-6-(propylamino)benzothiazole more efficiently than previous methods.

In various embodiments, the chiral purity for the R enantiomer prepared and purified may be greater than 99.6% about when a starting material that is entantiomerically enriched for R diamine is used. Similarly, in various other embodiments, the chiral purity for the S enantiomer produced and purified may be greater than 99.6% when a starting material that is entantiomerically enriched for S diamine is used. In some embodiments, the chiral purity for the R enantiomer prepared and purified may be greater than 99.8% about when a starting material that is entantiomerically enriched for .R diamine is used. Similarly, in some other embodiments, the chiral purity for the S enantiomer produced and purified may be greater than 99.8% when a starting material that is entantiomerically enriched for S diamine is used. In particular embodiments, the chiral purity for the R enantiomer prepared and purified may be greater than 99.9% about when a starting material that is entantiomerically enriched for R diamine is used. Similarly, in particular other embodiments, the chiral purity for the S enantiomer produced and purified may be greater than 99.9% when a starting material that is entantiomerically enriched for S diamine is used.

Not wishing to be bound by theory, the solubility of (6R)-4,5,6,7-tetrahydro-N6-propyl-2,6-benzothiazole-diamine and (6S)-4,5,6,7-tetrahydro-N6-propyl-2,6-benzothiazole-diamine may be the same in the trituration step of the synthesis and purification processes. For example, if a synthesis process is carried out with 90 grams of the (6R) diamine and 10 grams of the (6S)diamine, and the solubility of the final 2-amino-4,5,6,7-tetrahydro-6-(propylamino) benzothiazole product is 10 grams for either enantiomer, then 80 grams of the (6R)-4,5,6,7-tetrahydro-N6-propyl-2, 6-benzothiazole-diamine product and 0 gams of the (6S)-4, 5,6,7-tetrahydro-N6-propyl-2,6-benzothiazole-diamine product would precipitate (assuming a 100% chemical conversion from the diamine and no change in molecular weight in going to the 2-amino-4,5,6,7-tetrahydro-6-(propylamino) benzothiazole product). That is, 10 grams of each enantiomer of 2-amino-4,5,6,7-tetrahydro-6-(propylamino) benzothiazole may be expected to go into solution. This would lead to a 2-amino-4,5,6,7-tetrahydro-6-(propylamino) benzothiazole product with a 100% chiral purity for the (6R) enantiomer. The opposite ratio of starting materials for the synthesis process (90 grams of the (6S) diamine and 10 grams of the (6R) diamine) may generate a reaction product of 90 grams of the (6S)-4,5,6,7-tetrahydro-N6-propyl-2,6-benzothiazole-diamine and 10 grams of the (6R)-4,5,6,7-tetrahydro-N6-propyl-2,6-benzothiazole-diamine. From this reaction product mixture, 80 grams of the (6S) enantiomer and 0 grams of the (6R) enantiomer of 2-amino-4,5,6,7-tetrahydro-6-(propylamino)benzothiazole would be expected to precipitate, leading to a 2-amino-4,5,6,7-tetrahydro-6-(propylamino)benzothiazole product with a 100% chiral purity for the (6S) enantiomer. Thus, the volumes which are used for a reaction may have a large potential effect on the final yield and chiral purity. That is, too large a volume will reduce the yield as more of the 2-amino-4,5, 6,7-tetrahydro-6-(propylamino)benzothiazole enantiomer products will go into solution (but increase the chiral purity) and too small a volume will increase the yield as less of the 2-amino-4,5,6,7-tetrahydro-6-(propylamino)benzothiazole products will go into solution (but reduce the chiral purity).

Other embodiments of the invention are directed to a process for the purification of entantiomerically pure 2-amino-4,5,6,7-tetrahydro-6-(propylamino)benzothiazole from a mixture of (6R)-4,5,6,7-tetrahydro-N6-propyl-2,6-benzothiazole-diamine and (6S)-4,5,6,7-tetrahydro-N6-propyl-2,6-benzothiazole-diamine including a trituration step. In some embodiments, the mixture of (6R)-4,5,6,7-tetrahydro-N6-propyl-2,6-benzothiazole-diamine and (6S)-4,5,6, 7-tetrahydro-N6-propyl-2,6-benzothiazole-diamine used in the purification methods may be prepared as described herein above. In other embodiments, the mixture of (6R)-4,5,6,7-tetrahydro-N6-propyl-2,6-benzothiazole-diamine and (6S)-4,5,6,7-tetrahydro-N6-propyl-2,6-benzothiazole-diamine may be obtained using another method or form a commercially available mixture of (6R)-4,5,6,7-tetrahydro-N6-propyl-2,6-benzothiazole-diamine and (6S)-4,5,6,7-tetrahydro-N6-propyl-2,6-benzothiazole-diamine.

In some embodiments, the trituration step may include the addition of an achiral salt to a solution containing a mixture of (6R)-4,5,6,7-tetrahydro-N6-propyl-2,6-benzothiazole-diamine and (6S)-4,5,6,7-tetrahydro-N6-propyl-2,6-benzothiazole-diamine. As described above, the addition of an achiral salt to a solution containing a mixture of (6R)-4,5,6,7-tetrahydro-N6-propyl-2,6-benzothiazole-diamine and (6S)-4,5,6,7-tetrahydro-N6-propyl-2,6-benzothiazole-diamine may cause the enantiomer having a greater concentration to become insoluble and form crystals in the solution. In some embodiments, the solution containing a mixture of (6R)-4,5,6,7-tetrahydro-N6-propyl-2,6-benzothiazole-diamine and (6S)-4,5,6,7-tetrahydro-N6-propyl-2,6-benzothiazole-diamine may be heated to an elevated temperature such as, for example, about 50° C. to about 125° C., about 55° C. to about 100° C., about 60° C. to about 95° C. or about 60° C. to about 75° C. and an achiral salt may be added to the solution. This solution may than be cooled from the elevated temperature to about room temperature slowly. For example in one embodiment, the reaction may be cooled at a rate of about less than 25° C./hour. In another embodiment, the reaction may be slowly cooled and the reaction solution may be stirred for at least about an additional 2 hours. The rates of cooling and the time required for the additional stirring may vary with the choice of achiral salt and may be easily appreciated by one skilled in the art.

The crystalline (6R)-4,5,6,7-tetrahydro-N6-propyl-2,6-benzothiazole-diamine or (6S)-4,5,6,7-tetrahydro-N6-propyl-2,6-benzothiawle-diamine may then be isolated, washed and dried, and in various embodiments, may result in entantiomerically pure (6R)-4,5,6,7-tetrahydro-N6-propyl-2,6-benzothiazole-diamine or (6S)-4,5,6,7-tetrahydro-N6-propyl-2,6-benzothiazole-diamine having a chemical purity of at least 97% and, in some embodiments, 98% to 100%. In such embodiments, the achiral salt may be any achiral salt listed hereinabove or any other achiral salt known in the art. Similarly, the solvent of the (6R)-4,5,6,7-tetrahydro-N6-propyl-2,6-benzothiazole-diamine and (6S)-4,5,6,7-tetrahydro-N6-propyl-2,6-benzothiazole-diamine solution may be any solvent described above in relation to the method for preparing 2-amino-4,5,6,7-tetrahydro-6-(propylamino)benzothiazole. Either (6R)-4,5,6,7-tetrahydro-N6-propyl-2,6-benzothiazole-diamine or (6S)-4,5,6,7-tetrahydro-N6-propyl-2,6-benzothiazole-diamine may be purified using the process of such embodiments. However, in certain embodiments, (6R)-4,5,6,7-tetrahydro-N6-propyl-2,6-benzothiazole-diamine may be purified.

In other embodiments, entantiomerically enriched 2-amino-4,5,6,7-tetrahydro-6-(propylamino)benzothiazole may be triturated from an acid addition solution based on the insolubility of the enantiomers in the achiral reagents. Various embodiments of this method may include the steps of dissolving an entantiomerically enriched 2-amino-4,5,6,7-tetrahydro-6-(propylamino)benzothiazole in a solvent at an elevated temperature such as, for example, about 50° C. to about 125° C., about 55° C. to about 100° C., about 60° C. to about 95° C. or about 60° C. to about 75° C., adding an acid to the dissolved 2-amino-4,5,6,7-tetrahydro-6-(propylamino)benzothiazole, cooling the reaction to about room temperature (25° C.) with stirring, stirring the cooled reaction mixture for an extended time at room temperature to allow formation of entantiomerically pure crystals and recovering entantiomerically pure (6R) or (6S)-4,5,6,7-tetrahydro-N6-propyl-2,6-benzothiazole-diamine from the reaction mixture. In other embodiments, entantiomerically enriched 2-amino-4,5,6,7-tetrahydro-6-(propylamino)benzothiazole may be dissolved in a solvent at an elevated temperature, about 0.5 equivalents to about 2.05 equivalents of an acid may be added to the solution and the solution may be cooled to room temperature. The cooled solution may then be stirred for an extended period of time and entantiomerically pure 2-amino-4,5,6,7-tetrahydro-6-(propylamino)benzothiazole may be recovered. In particular embodiments, the selected acid may be p-toluenesulfonic acid (p-TSA) and the solvent may be ethanol. In other embodiments, the temperature of the solution when the acid is added may be lower than about 125° C., lower than about 100° C. or lower than about 75° C., and in certain embodiments, the temperature may be from about 65° C. to about 85° C. The cooling may generally occur slowly at, for example, a rate of about 25° C. per hour and the solution may be stirred for at least about 2 hours after 25° C. temperature has been reached. The times necessary for the reaction may vary with the identities of the reactants, the solvent system and with the chosen temperature, and may be easily appreciated by one of skill in the art. Reaction volumes may additionally dictate the degree of optical purification and the overall yield of the optically pure 2-amino-4,5,6,7-tetrahydro-6-(propylamino)benzothiazole. These volumes would be understood and appreciated by one of skill in the art. Examples of specific times, temperatures and volumes which enable the practice of this invention are given in the Examples.

The solvent utilized may vary in embodiments and may generally be an organic solvent such as, for example, acetonitrile, acetone, ethanol, ethyl acetate, methyl tert-butyl ether, methyl ethyl ketone, isopropyl acetate, isopropyl alcohol and combinations thereof. In a particular embodiment, the organic solvent may be ethanol.

The acid of various embodiments may include: halogenic acids such as, for example, hydrobromic, hydrochloric, hydrofluoric and hydroiodic acid; inorganic acids such as, for example, nitric, perchloric, sulfuric and phosphoric acid; organic acids such as, for example, sulfonic acids (methanesulfonic, trifluoromethane sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid; and amino acids such as aspartic or glutamic acid. The acid may be a mono- or di-acid, such as, for example, a di-hydrohalogenic, di-sulfuric, di-phosphoric or di-organic acid. The acid of embodiments may be used as an achiral reagent which is, generally, not selected on the basis of any expected or known preference for interaction with, or precipitation of, a specific optical isomer of the 2-amino-4,5,6,7-tetrahydro-6-(propylamino)benzothiazole to be isolated. For example, in one embodiment, the selected acid may be p-toluenesulfonic acid. The amount of acid added may vary and is generally provided at about 1 molar equivalent to about 4 molar equivalents of the 2-amino-4,5,6,7-tetrahydro-6-(propylamino)benzothiazole.

Insoluble 2-amino-4,5,6,7-tetrahydro-6-(propylamino)benzothiazole may be separated from the reaction solution by any method known in the art. For example, in some embodiments, the 2-amino-4,5,6,7-tetrahydro-6-(propylamino)benzothiazole may be collected by simple filtering. There are numerous methods for filtering a solid from a solution, and any such method may by useful in embodiments of the invention. In other embodiments, insoluble 2-amino-4,5,6,7-tetrahydro-6-(propylamino)benwthiazole may be isolated by centrifugation. Again, such methods are well known in the art and any such method may be used in various embodiments of the invention. The insoluble crystalline 2-amino-4,5,6,7-tetrahydro-6-(propylamino)benzothiazole may then be washed to remove any contaminating solvent, sulfonate or halide salt, or soluble enantiomer of 2-amino-4,5,6,7-tetrahydro-6-(propylamino)benzothiazole from the crystals using any method available. For example, in one embodiment, the precipitated material may be washed in a volatile solvent such as an alcohol or heptane followed by vacuum drying.

The 2-amino-4,5,6,7-tetrahydro-6-(propylamino)benzothiazole enantiomers prepared using methods above may be purified from a starting (6R)-4,5,6,7-tetrahydro-N6-propyl- 2,6-benzothiazole-diamine and (6S)-4,5,6,7-tetrahydro-N6-propyl-2,6-benzothiazole-diamine mixture that is enriched for one or the other enantiomers. For example, in some embodiments, the starting mixture may contain at least 55% or greater of either the R or S enantiomer, and in others the starting mixture may contain about 70% or greater of either the R or the S enantiomer. In still other embodiments, the starting material may contain greater than about 90% of either the R or S enantiomer. In particular embodiments, the starting mixture is enriched for (6R)-4,5,6,7-tetrahydro-N6-propyl-2,6-benzothiazole-diamine.

Without wishing to be bound by theory, the relative solubility of the optical isomers of the 2-amino-4,5,6,7-tetrahydro-6-(propylamino)benzothiazole in the achiral salt or acid solutions allows for chiral and chemical purification that is unexpected by using a relatively easy recovery method via a simple trituration step. The enhanced enrichment resulting from the purification methods described above result in that may reach optical purity. For example, in various embodiments, the final 2-amino-4,5,6,7-tetrahydro-6-(propylamino)benzothiazole product may be enriched to 99% optical purity or greater, 99.5% optical purity or greater, 99.8% optical purity or greater, and in certain embodiments, 99.9% optical purity or greater. In still other embodiments, the optical purity of the final 2-amino-4,5,6,7-tetrahydro-6-(propylamino)benzothiazole may be 99.95% or greater, or even 99.9.9% or greater. In particular embodiments, the optical purity may be 100%.

The processes disclosed herein have several advantages. First, the processes avoid the use of borane reagents such as sodium borohydride, common in the reductive amination schemes used in the prior art, which decomposes rapidly to borane and hydrogen upon acidification. Second, reductive amination schemes involve the use of a two-step procedure in which the amide is formed first, followed by a reduction step. The methods of this disclosure are one-pot synthesis and purification procedures, and therefore provide a safer, easier and more economical synthesis. Third, there is no loss of chirality during the alkylation processes of the $S_N 2$ reaction mechanism of this disclosure, as opposed to previous synthesis schemes where chiral purity is often reduced or lost altogether during synthesis. Finally, the 2-amino-4,5,6,7-tetrahydro-6-(propylamino)benzothiazole product of the nucleophilic substitution reaction precipitates from the reaction mixture. This may be especially true for the p-TSA salt form of 2-amino-4,5,6,7-tetrahydro-6-(propylamino)benzothiazole. This is an unexpected advantage of the methods of the instant disclosure and provides unique methods for chiral and chemical enrichment or purification of the final 2-amino-4,5,6,7-tetrahydro-6-(propylamino)benzothiazole product.

Additional embodiments of the invention include the conversion of either sulfonate or halide salts of 2-amino-4,5,6,7-tetrahydro-6-(propylamino)benzothiazole or free base 2-amino-4,5,6,7-tetrahydro-6-(propylamino)benzothiazole into an hydrochloric acid (HCl) salt as illustrated in FIG. 2. For example, in some embodiments, solid 2-amino-4,5,6,7-tetrahydro-6-(propylamino)benzothiazole sulfonate or halide salt (8) may be re-dissolved in an alcohol, such as ethanol, and the mixture may be cooled to between about 0 and about 5° C. with continuous stirring. Concentrated HCl may then be added, followed by a solvent such as methyl tert-butyl ether (MTBE), and the mixture may be stirred for about 0.5 to about 3 hours at between about 0 and about 5° C. until or until insoluble 2-amino-4,5,6,7-tetrahydro-6-(propylamino)benzothiazole dihydrochloride crystals (10) have formed. The reaction mixture may then be filtered, washed in an inert solvent such as MTBE/alcohol solution and dried under vacuum. A detailed example of this synthesis may be found in Example 12.

In another embodiment, of 2-amino-4,5,6,7-tetrahydro-6-(propylamino)benzothiazole sulfonate or halide salts (8) may be converted to an HCl salt using a concentrated solution of HCl and isopropyl acetate (IPAC). In such embodiments, 2-amino-4,5,6,7-tetrahydro-6-(propylamino)benzothiazole sulfonate or halide salt (8) may be dissolved in IPAC and cooled to about 15° C. HCl (gas) may then be bubbled into the slurry for from about 0.5 hours to 3 hours to produce 2-amino-4,5,6,7-tetrahydro-6-(propylamino)benzothiazole dihydrochloride (10), after which the mixture may be filtered, washed with an inert solvent, such as, for example, IPAC and dried under vacuum at room temperature. A detailed example of this synthesis may be found in Example 13.

The sulfonate or halide salts of 2-amino-4,5,6,7-tetrahydro-6-(propylamino)benzothiazole may alternatively be converted to the free base form of 2-amino-4,5,6,7-tetrahydro-6-(propylamino)benzothiazole as illustrated in FIG. 2. For example, in one embodiment, a p-TSA 2-amino-4,5,6,7-tetrahydro-6-(propylamino)benzothiazole salt (8) may be dissolved in dichloromethane (DCM) and water. The solution may then by brought to a pH of about 11-12 using NaOH and resulting in the formation of two phases. The aqueous phase contains 2-amino-4,5,6,7-tetrahydro-6-(propylamino)benzothiazole that may be extracted with DCM, dried over magnesium sulfate. ($MgSO_4$), filtered over Celite® and concentrated. The concentrated residue may be re-dissolved in MTBE and stirred as a slurry for several hours. The solids may then be filtered, washed. with MTBE, and dried under vacuum at a temperature of about 35° C. The final product is 2-amino-4,5,6,7-tetrahydro-6-(propylamino)benzothiazole free base (9). A detailed example of this synthesis may be found in Example 14.

In another embodiment, the sulfonate or halide salts of 2-amino-4,5,6,7-tetrahydro-6-(propylamino)benzothiazole (8) may be converted to the free base form of 2-amino-4,5,6,7-tetrahydro-6-(propylamino)benzothiazole (9) by dissolving p-TSA salt of 2-amino-4,5,6,7-tetrahydro-6-(propylamino)benzothiazole in water and cooling the solution to a temperature of about 10° C. NaOH may be added to the solution to increase the pH, the solution may be diluted and extracted several times in DCM. The combined organic phases are then washed, dried over $MgSO_4$, filtered and concentrated to dryness. A detailed example of this synthesis may be found in Example 15.

In some embodiments, the free base form of 2-amino-4,5,6,7-tetrahydro-6-(propylamino)benzothiazole may be converted to 2-amino-4,5,6,7-tetrahydro-6-(propylamino)benzothiazole dihydrochloride (9) by bubbling HCl gas into a cooled solution of the 2-amino-4,5,6,7-tetrahydro-6-(propylamino)benzothiazole free base in IPAC. Alternatively, in other embodiments, the free base form of 2-amino-4,5,6,7-tetrahydro-6-(propylamino)benzothiazole (9) may be converted to 2-amino-4,5,6,7-tetrahydro-6-(propylamino)benzothiazole dihydrochloride (10) by mixing with concentrated HCl at room temperature overnight. Detailed examples of such schemes may be found in Examples 16 and 17, respectively. In still other embodiments, the free base form of 2-amino-4,5,6,7-tetrahydro-6-(propylamino)benzothiazole (9) may be converted to 2-amino-4,5,6,7-tetrahydro-6-(propylamino)benzothiazole fumarate (11) by the addition of about 1 to about 4 molar equivalents of fumaric acid.

The methods of the present disclosure require little time, utilize readily available starting materials and do not involve the use of hazardous or difficult to handle reagents. Each of the several steps of the methods disclosed as part of the present invention are high yielding and afford products with very high chemical and chiral purity. Further, the processes disclosed herein may be scaled for industrial scale manufacturing. As such, entantiomerically pure 2-amino-4,5,6,7-tetrahydro-6-(propylamino)benwthiazole may be manufactured in batches of greater than 1 kg or more, 10 kg or more, or even 25 kg or more as may be required to meet the needs of a large scale pharmaceutical use.

Embodiments of the invention also relate to a pure enantiomer of 2-amino-4,5,6,7-tetrahydro-6-(propylamino) benzothiazole, either (6R) or (6S), produced by processes disclosed herein. Thus, an embodiment of the invention is a chirally pure 2-amino-4,5,6,7-tetrahydro-6-(propylamino) benzothiazole salt prepared by a process which comprises dissolving 2,6 diamino-4,5,6,7-tetrahydro-benzothiazole in an organic solvent, reacting the 2,6 diamino-4,5,6,7-tetrahydro-benzothiazole with a n-propyl sulfonate or a n-propyl halide under conditions sufficient to generate the 2-amino-4,5,6,7-tetrahydro-6-(propylamino)benzothiazole salt and recovering the chirally pure 2-amino-4,5,6,7-tetrahydro-6-(propylamino)benzothiazole salt.

The present invention should not be considered limited to the particular embodiments described above, but rather should be understood to cover all aspects of the invention as fairly set out in the attached claims. Various modifications, equivalent processes, as well as numerous structures to which the present invention may be applicable, will be readily apparent to those skilled in the art to which the present invention is directed upon review of the present specification. The claims are intended to cover such modifications and devices. The invention and embodiments thereof illustrating the method and materials used may be further understood by reference to the following non-limiting examples.

EXAMPLES 2-amino-4,5,6,7-tetrahydro-6-(propylamino)benzothiazole was prepared using the $S_N2$ substitution reaction described above. Reactions were carried out under exemplary reactions conditions A, B and C described below. Results of example syntheses using each of the several conditions which are embodiments of the present disclosure are listed in Table 1. Several example syntheses .of 2-amino-4,5,6,7-tetrahydro-6-(propylamino)benzothiazole using conditions A, B and C of the present disclosure are detailed in Examples 1-5, the results are presented in Table 1.

A: diamine dissolved in an organic solvent was heated to a reaction temperature of less than about 125° C. with continuous stirring. A solution of n-propyl sulfonate or n-propyl halide dissolved in di-isoproplyethylamine and an organic solvent was added to the dissolved, heated diamine slowly over a period of up to several hours to form a mixture, and this reaction mixture was stirred at the reaction temperature for an additional period of time of up to about 4 hours.

B: diamine dissolved in an organic solvent was heated to a reaction temperature of less than about 125° C. with continuous stirring. A solution of n-propyl sulfonate or n-propyl halide dissolved in dimethylforrnamide was added slowly over a period of up to several hours to form a reaction mixture, and this reaction mixture was stirred at the reaction temperature for an additional amount of time up to about 4 hours.

C: diamine was dissolved in dimethylformamide and heated to less than about 125° C. with continuous stirring. A solution of n-propyl sulfonate or n-propyl halide dissolved in dimethylformamide and di-isopropylethylamine was added to the heated diamine slowly over a period of up to several hours to form a reaction mixture. This reaction mixture was then stirred at the reaction temperature for up to about 4 hours.

Alternatively, di-isoproplyethylamine may be added to the heated diamine dissolved in an organic solvent prior to the addition of a solution including n-propyl sulfonate or n-propyl halide dissolved in dimethylformamide. As above, the n-propyl sulfonate or propyl halide/dimethlyformamide solution may be added slowly for a time period up to several hours with continuous stirring and the reaction mixture formed may be stirred at the reaction temperature for up to about 4 hours.

These products were analyzed by high pressure liquid chromatography (HPLC) for chemical and chiral purity. $^1$H NMR and $^{13}$C NMR was also used to confirm the structure of the product is 2-amino-4,5,6,7-tetrahydro-6-(propylamino)benzothiazole Example 1

Preparation of (6R)-4,5,6,7-tetrahydro-N6-propyl-2, 6-benzothiazole-diaminep-TSA Salt: Condition A A 2.0 liter, three necked flask was equipped with an overhead stirrer, a temperature probe, a heating mantle, a claisen joint, a reflux condenser, and a 500 ml addition funnel. The flask was charged with 45 grams of (6R)-4,5,6,7-tetrahydro-N6-propyl-2,6-benzothiazole-diamine, followed by 750 ml of n-propanol. Under continuous stirring, the mixture was heated to 95° C. over 15 minutes generating a clear solution. The addition funnel was charged with a solution of 74 grams propyl tosylate and 60 ml diisopropylethyleamine in 250 ml n-propanol. This solution was added dropwise to the 2.0 liter flask with continuous stirring over a period of 4 hours. The reaction was continued with stirring for an additional 8 hours at 95° C., after which the solution was brought to room temperature, and stirring was continued for an additional 4 hours.

The precipitated material was collected by filtration and washed three times using 100 ml reagent grade alcohol each time. The alcohol washed precipitated cake was then washed with 100 ml heptane and dried under high vacuum for 2 hours.

The final weight of the dried product was 53.2 grams, representing a 52.2% yield. HPLC was used to determine the chemical purity of the (6R)-2,6-diamino-4,5,6,7-tetrahydro-benzothiazole as 98.2% and the chiral purity as greater than 99.5%. $^1$H NMR and $^{13}$C NMR were used to confirm the structure.

Example 2

Preparation of (6S)-4,5,6,7-tetrahydro-N6-propyl-2, 6-benzothiazole-diaminep-TSA Salt: Condition A A 250 ml, three necked flask was equipped with a magnetic stirrer, a temperature probe, a heating mantle, a claisen joint, a reflux condenser, and a 50 ml addition funnel. The flask was charged with 5 grams of (6S)-2,6 diamino-4, 5,6,7-tetrahydro-benzothiazole, followed by 45 ml of n-propanol. Under continuous stirring, the mixture was heated to a temperature of 95° C. over 15 minutes generating a clear solution. The addition funnel was charged with a solution of 8.2 grams propyl tosylate and 6.7 ml diisopropylethyleamine in 16 ml n-propanol. This solution was added dropwise to the 250 ml flask with continuous stirring over a period of 2 hours. The reaction was continued with stirring for an additional 6 hours at 95° C., after which the solution was brought to room temperature, and stirring was continued for an additional 4 hours.

The precipitated material was collected by filtration and washed three times using 10 ml reagent grade alcohol each time. The alcohol washed precipitated cake was then washed with 10 ml heptane and dried under high vacuum for 2 hours.

The final weight of the dried product was 4.99 grams, representing a 44.2% yield. HPLC was used to determine the chemical purity of the (6S)-2,6-diamino-4,5,6,7-tetrahydro-benzothiazole as 98.0% and the chiral purity as greater than 99.6%. $^1$H NMR was used to confirm the structure.

Example 3

Preparation of racemic 2-amino-4,5,6,7-tetrahydro-6-(propylamino)benzothiazole p-TSA Salt: Condition A A 250 ml, three necked flask was equipped with a magnetic stirrer, a temperature probe, a heating mantle, a claisen joint, a reflux condenser, and a 100 ml addition funnel. The flask was charged with 5 grams of racemic 2,6 diamino-4,5,6,7-tetrahydro-benzothiazole, followed by 80 ml of n-propanol. Under continuous stirring, the mixture was heated to a temperature of 95° C. over 15 minutes generating a clear solution. The addition funnel was charged with a solution of 10.1 grams propyl tosylate and 8.2 ml diisopropylethyleamine in 28 ml n-propanol. This solution was added dropwise to the 250 ml flask with continuous stirring over a period of 2 hours. The reaction was continued with stirring for an additional 6 hours at 95° C., after which the solution was brought to room temperature, and stirring was continued for an additional 6 hours.

The precipitated material was collected by filtration and washed two times using 25 ml reagent grade alcohol each time. The alcohol washed precipitated cake was then washed with 25 ml heptane and dried under high vacuum for 1 hour.

The final weight of the dried product was 5.12 grams, representing a 45% yield. HPLC was used to determine the chemical purity of the racemic 2,6-diamino-4,5,6,7-tetrahydro-benzothiazole as 97.1%, and the chiral purity showed a 1:1 mixture of the (6R) and (6S)-4,5,6,7-tetrahydro-N6-propyl-2,6-benzothiazole-diamine. $^1$H NMR was used to confirm the structure.

Example 4

Preparation of (6R)-4,5,6,7-tetrahydro-N6-propyl-2,6-benzothiazole-diamine p-TSA Salt: Condition B A 250 ml, three necked flask was equipped with a magnetic stirrer, a temperature probe, a heating mantle, a claisen joint, a reflux condenser, and a 50 ml addition funnel. The flask was charged with 5 grams of (6R)-2,6 diamino-4,5,6,7-tetrahydro-benzothiazole, followed by 50 ml of DMF. Under continuous stirring, the mixture was heated to a temperature of 75° C. 6.3 grams propyl tosylate was added dropwise to the 250 ml flask with continuous stirring over a period of 6 hours. Progress of the reaction was monitored by analysis on HPLC.

The reaction was continued with stirring for an additional 12 hours at room temperature. The solution was diluted with 20 ml. MTBE and stirred for an additional hour. The precipitated material was collected by filtration and washed with 20 ml MTBE, followed by 2 washes of 20 ml each ethanol. The washed precipitated cake was dried under high vacuum.

The final weight of the dried product was 4.6 grams, representing a 40% yield. HPLC was used to determine the chemical purity of the (6R)-4,5,6,7-tetrahydro-N6-propyl-2,6-benzothiazole-diamine as 94.9% and the chiral purity as greater than 99.6%. $^1$H NMR was used to confirm the structure.

Example 5

Preparation of (6S)-4,5,6,7-tetrahydro-N6-propyl-2,6-benzothiazole-diamine p-TSA Salt: Condition B A 250 ml, three necked flask was equipped with a magnetic stirrer, a temperature probe, a heating mantle, a claisen joint, a reflux condenser, and a 50 ml addition funnel. The flask was charged with 10 grams of (6S)-2,6 diamino-4,5,6,7-tetrahydro-benzothiazole, followed by 100 ml of DMF. Under continuous stirring, the mixture was heated to a temperature of 75° C. The addition funnel was charged with a solution of 16.4 grams propyl tosylate in 20 ml DMF. This solution was added dropwise to the 250 ml flask with continuous stirring over a period of 1.5 hours. Progress of the reaction was monitored by analysis on HPLC.

The reaction was continued with stirring for an additional 12 hours at 75° C., after which the solution was brought to room temperature, and stirring was continued for an additional 7 hours. The solution was diluted with 100 ml MTBE and stirred for an additional hour. The precipitated material was collected by filtration and washed with 100 ml MTBE, followed by 2 washes of 50 ml each ethanol, and a wash with 50 ml heptane. The washed precipitated cake was dried under high vacuum.

The final weight of the dried product was 9.81 grams, representing a 43.3% yield. HPLC was used to determine the chemical purity of the (6S)-4,5,6,7-tetrahydro-N6-propyl-2,6-benzothiazole-diamine as 99.4% and the chiral purity as greater than 99.8%. $^1$H NMR was used to confirm the structure.

Example 6

Preparation of racemic 2-amino-4,5,6,7-tetrahydro-6-(propylamino)benzothiazolep-TSA Salt: Condition B A 250 ml, three necked flask was equipped with a magnetic stirrer, a temperature probe, a heating mantle, a claisen joint, a reflux condenser, and a 50 ml addition funnel. The flask was charged with 5 grams of racemic-2,6 diamino-4,5,6,7-tetrahydro-benzothiazole, followed by 50 ml of DMF. Under continuous stirring, the mixture was heated to a temperature of 75° C. 9.5 grams was added to the 250 ml flask with continuous stirring. Progress of the reaction was monitored by analysis on HPLC.

The reaction was continued with stirring for an additional 4 hours at 75° C., after which the solution was brought to room temperature, and stirring was continued for an additional 12 hours. The solution was diluted with 20 ml MTBE and stirred for an additional hour. The precipitated material was collected by filtration and washed with 50 ml MTBE, followed by 3 washes of 25 ml each ethanol, and the precipitated cake was dried under high vacuum.

The final weight of the dried product was 2.9 grams, representing a 25.6% yield. HPLC was used to determine the chemical purity of the racemic 2,6-diamino-4,5,6,7-tetrahydro-benzothiazole as 98.3%, and the chiral purity showed a 1:1 mixture of the (6R) and (6S)-4,5,6,7-tetrahydro-N6-propyl-2,6-benzothiazole-diamine. $^1$H NMR was used to confirm the structure.

Example 7

Preparation of (6R)-4,5,6,7-tetrahydro-N6-propyl-2, 6-benzothiazole-diamine p-TSA Salt: Condition C A 12 L, three necked flask was equipped with an overhead stirrer, a temperature probe, a heating mantle, a claisen joint, a condenser, and a 500 ml addition funnel. The flask was charged with 250 grams of (6R)-2,6 diamino-4,5,6,7-tetrahydro-benzothiazole, followed by 2 L of dimethyl formamide (DMF). Under continuous stirring, the mixture was heated to a temperature of 65° C. The addition funnel was charged with a solution of 386.6 grams propyl tosylate and 322 ml diisopropylethyleamine in 500 ml DMF. This solution was added to the 12 L flask dropwise over a period of 2.0 hours. The reaction was monitored by analysis on HPLC.

The reaction was continued at 65° C. for an additional 5 hours, after which the solution was gradually cooled to room temperature and stirred overnight. The solution was diluted with 2 L MTBE and stirred for an additional 0.5 hours. The precipitated material was collected by filtration and washed with 500 ml MTBE, followed by 3 washes of 500 ml each reagent alcohol. The washed precipitated cake was dried under high vacuum.

The final weight of the, dried product was 317.6 grams, representing a 56% yield. HPLC was used to determine the chemical purity of the (6R)-2,6-diamino-4,5,6,7-tetrahydro-benzothiazole as 98.4% and the chiral purity as greater than 99.8%. NMR and $^{13}$C NMR was used to confirm the structure: $^1$H NMR (300 MHz, DMSO-d6) δ 8.5 (br.s, 2H), 7.5 (d, 2H), 71.2 (d, 1H), 6.8 (s, 2H), 3.4 (m, 1H), 2.95 (m, 3H), 2.6 (m, 2H, merged with DMSO peak), 2.3 (s, 3H), 2.15 (m, 1H), 1.8 (m, 1H), 1.55 (m, 2H), 0.9 (t, 3H); $^{13}$C NMR (300 MHz, DMSO-d6) δ 167.0, 145.5, 144.6, 138.4, 128.6, 125.8, 110.7, 53.9, 46.5, 25.8, 25.6, 24.5, 21.2, 19.6, 11.3.

Example 8

Preparation of (6S)-4,5,6,7-tetrahydro-N6-propyl-2, 6-benzothiazole-diamine p-TSA Salt: Condition C A 500 ml, three necked flask was equipped with an overhead stirrer, a temperature probe, a heating mantle, a claisen joint, a condenser, and a 100 ml addition funnel. The flask was charged with 20 grams of (6S)-2,6 diamino-4,5, 6,7-tetrahydro-benzothiazole, followed by 180 ml of dimethyl formamide (DMF). Under continuous stirring, the mixture was heated to a temperature of 65° C. The addition funnel was charged with a solution of 35.5 grams propyl tosylate and 32.8 ml diisopropylethylamine in 40 ml DMF. This solution was added to the 500 ml flask dropwise over a period of 2.0 hours. The reaction was monitored by analysis on HPLC.

The reaction was continued at 65° C. for an additional 10 hours, after which the solution was gradually cooled to room temperature and stirred for 6 hours. The solution was diluted with 220 ml MTBE and stirred for an additional 0.5 hours. The precipitated material was collected by filtration and washed with 50 ml MTBE, followed by 3 washes of 50 ml each reagent alcohol and a wash with 75 ml of heptane. The washed precipitated cake was dried under high vacuum.

The final weight of the dried product was 25.4 grams, representing a 56% yield. HPLC was used to determine the chemical purity of the (6S)-2,6-diamino-4,5,6,7-tetrahydro-benzothiazole as 99.4% and the chiral purity as greater than 99.7%. $^1$H NMR and $^{13}$C NMR was used to confirm the structure: $^1$H NMR (300 MHz, DMSO-d6) δ 8.5 (br.s, 2H), 7.5 (d, 2H), 71.2 (d, 1H), 6.8 (s, 2H), 3.4 (m, 1H), 2.95 (m, 3H), 2.6 (m, 2H, merged with DMSO peak), 2.3 (s, 3H), 2.15 (m, 1H), 1.8 (m, 1H), 1.55 (m, 2H), 0.9 (t, 3H).

Example 9

Preparation of racemic 2-amino-4,5,6,7-tetrahydro-6-(propylamino)benzothiazole p-TSA Salt: Condition C A 250 ml, three necked flask was equipped with a magnetic stirrer, a temperature probe, a heating mantle, a claisen joint, a reflux condenser, and a 50 ml addition funnel. The flask was charged with 5 grams of racemic-2,6 diamino-4,5,6,7-tetrahydro-benzothiazole, followed by 45 ml of DMF. Under continuous stirring, the mixture was heated to a temperature of 65° C. The addition funnel was charged with a solution of 8.86 grams propyl tosylate and 8.2 ml of diisopropylethylamine in 10 ml. DMF. This solution was added dropwise to the 250 ml flask with continuous stirring over a period of 2 hours. Progress of the reaction was monitored by analysis on HPLC.

The reaction was continued with stirring for an additional 6 hours at 65° C., after which the solution was brought to room temperature. The solution was diluted with 70 ml MTBE and stirred for an additional hour. The precipitated material was collected by filtration and washed with 15 ml MTBE, followed by 2 washes of 15 ml each ethanol, and a wash with 15 ml heptane. The washed precipitated cake was dried under high vacuum.

The final weight of the dried product was 6.02 grams, representing a 53.1% yield. HPLC was used to determine the chemical purity of the racemic 2,6-diamino-4,5,6,7-tetrahydro-benzothiazole as 99.2%, and the chiral purity showed a 1:1 mixture of the (6R) and (6S)-4,5,6,7-tetrahydro-N6-propyl-2,6-benzothiazole-diamine. $^1$H NMR was used to confirm the structure.

Example 10

Preparation of (6R)-4,5,6,7-tetrahydro-N6-propyl-2, 6-benzothiazole-diamine p-TSA Salt: Condition E A 1000 ml, three necked flask was equipped with an overhead stirrer, a temperature probe, a heating mantle, a claisen joint, a condenser, and a 250 ml addition funnel. The flask was charged with 25 grams of (6R)-2,6 diamino-4,5, 6,7-tetrahydro-benzothiazole, followed by 200 ml of dimethyl formamide (DMF). Under continuous stirring, the mixture was heated to a temperature of 75° C. The addition funnel was charged with a solution of 39.5 grams propyl tosylate and 32.5 ml diisopropylethyleamine in 50 ml DMF,.

This solution was added to the 1000 ml flask dropwise over a period of 1.0 hours. The reaction was monitored by analysis on HPLC.

The reaction was continued at 75° C. for an additional 5 hours, after which the solution was gradually cooled to room temperature and stirred overnight. The precipitated material was collected by filtration and washed with 2 washes with 100 ml MTBE, followed by 3 washes of 75 ml each reagent alcohol and one wash with 125 ml of heptane. The washed precipitated cake was dried under high vacuum.

The reaction resulted in a 47% yield. HPLC was used to determine the chiral purity as 99.8%. $^1$H NMR and $^{13}$C NMR was used to confirm the structure.

Example 11

Preparation of (6S)-4,5,6,7-tetrahydro-N6-propyl-2,6-benzothiazole-diamine p-TSA Salt: Condition E A 1000 ml, three necked flask was equipped with an overhead stirrer, a temperature probe, a heating mantle, a claisen joint, a condenser, and a 250 ml addition funnel. The flask was charged with 25 grams of (6S)-2,6 diamino-4,5,6,7-tetrahydro-benzothiazole, followed by 200 ml of dimethyl formamide (DMF). Under continuous stirring, the mixture was heated to a temperature of 75° C. The addition funnel, was charged with a solution of 39.5 grams propyl tosylate and 32.5 ml diisopropylethyleamine in 50 ml DMF. This solution was added to the 1000 ml flask dropwise over a period of 2.0 hours. The reaction was monitored by analysis on HPLC.

The reaction was continued at 65° C. for an additional 5 hours, after which the solution was gradually cooled to room temperature and stirred overnight. The precipitated material was collected by filtration and washed with twice with 10 ml MTBE, followed by 3 washes of 75 ml each reagent alcohol and one wash with 125 ml of heptane. The washed precipitated cake was dried under high vacuum.

The reaction resulted in a 47% yield. HPLC was used to determine the chiral purity as 99.8%. $^1$H NMR and $^{13}$C NMR was used to confirm the structure.

TABLE 1

Experiments for $S_N2$ preparation of 2-amino-4,5,6,7-tetrahydro-6-(propylamino)benzothiazole pTSA salt

| Condition | Isomer | Batch Size | Results |
|---|---|---|---|
| Ex. 1 | (6R) | 45 grams | Yield = 53.2 grams (52%) Chemical Purity = 98.2% AUC by HPLC Chiral Purity => 99.5% AUC by HPLC |
| Ex. 2 | (6S) | 5 grams | Yield = 4.99 grams (44.2%) Chemical Purity = 98.0% AUC by HPLC Chiral Purity => 99.6% AUC by HPLC |
| Ex. 3 | Racemic | 5 gram | Yield = 5.12 grams (45%) Chemical Purity = 97.1% AUC by HPLC Chiral Purity = 1:1 (6R):(6S) by HPLC |
| Ex. 4 | (6R) | 5 gram | Yield = 4.6 grams (40%) Chemical Purity = 94.9% AUC by HPLC Chiral Purity = 99.6% AUC by HPLC |
| Ex. 5 | (6S) | 10 gram | Yield = 9.81 grams (43.3%) Chemical Purity = 94.9% AUC by HPLC Chiral Purity = 99.7% AUC by HPLC |
| Ex. 6 | Racemic | 5 gram | Yield = 2.9 grams (25.6%) Chemical Purity = 98.3% AUC by HPLC Chiral Purity = 1:1 (6R):(6S) by HPLC |
| Ex. 7 | (6R) | 250 gram | Yield = 317.6 grams (56%) Chemical Purity = 99.4% AUC by HPLC Chiral Purity = 99.8% AUC by HPLC |
| Ex. 8 | (6S) | 20 gram | Yield = 25.41 grams (56%) Chemical Purity = 99.4% AUC by HPLC Chiral Purity = 99.7% AUC by HPLC |
| Ex. 9 | Racemic | 5 gram | Yield = 6.02 grams (53.1%) Chemical Purity = 99.2% AUC by HPLC Chiral Purity = 1:1 (6R):(6S) by HPLC |
| Ex. 10 | (6R) | 25 gram | Yield = 47% Chiral Purity = 99.8% AUC by HPLC |
| Ex. 11 | (6S) | 25 gram | Yield = 47% Chiral Purity = 99.8% AUC by HPLC |

Example 11

Various ratios of entantiomerically enriched mixtures of (6R)2,6 diamino-4,5,6,7-tetrahydro-benzothiazole and (6S) 2,6 diamino-4,5,6,7-tetrahydro-benzothiazole having (6R) to (6S) ratios of: 80:20, 20:80, 85:15, 15:85, 90:10, 10:90, 95:5 and 5:95, were used to prepare (6R) or (6S)-4,5,6,7-tetrahydro-N6-propyl-2,6-benzothiazole-diamine based on the enriched species in the starting material. The following reaction conditions were used:

F: 2,6 diamino-4,5,6,7-tetrahydro-benzothiazole mixtures were dissolved in 10 volumes of DMF and 1.25 equivalents of propyl tosylate. at 65-67° C. The reaction is then cooled to room temperature, insoluble species were collected and washed with 8 volumes of MTBE.

G: 2,6 diamino-4,5,6,7-tetrahydro-benzothiazole mixtures were dissolved in 18 volumes of DMF and 1.25 equivalents of propyl tosylate at 65-67° C. The reaction is then cooled to room temperature, insoluble species were collected and washed with 8 volumes of MTBE.

H: 2,6 diamino-4,5,6,7-tetrahydro-benzothiazole mixtures were dissolved in 10 volumes of DMF and 1.25 equivalents of propyl tosylate at. 65-67° C. The reaction is then cooled to room temperature and insoluble species were collected. No washing step was performed.

Results are compiled in Table 2:

TABLE 2

Experiments for $S_N2$ preparation of pure enantiomers of 2-amino-4,5,6,7-tetrahydro-6-(propylamino)benzothiazole

| Ratio of starting diamines (6R):(6S) | Condition F (yield/chiral purity) | Condition G (yield/chiral purity) | Condition H (yield/chiral purity) |
|---|---|---|---|
| 80:20 | — | 29%/99% | 34%/98.2% |
| 20:80 | — | 30%/99.4% | 35%/95.7% |
| 85:15 | 43%/86.8% | 36%/99.8% | 39%/99.9% |
| 15:85 | 52%/88.9% | 27%/99.6% | 37%/99.9% |
| 90:10 | 47%/95.9% | — | — |
| 10:90 | 58%/93.6% | — | — |
| 95:5 | 50%/99.6% | — | — |
| 5:95 | 47%/99.6% | — | — |

The data in Table 2 demonstrates that both enantiomers of 2-amino-4,5,6,7-tetrahydro-6-(propylamino)benzothiazole have similar, if not the same, solubility. Further, the data shows that the synthesis is equally efficient for either enantiomer of 2-amino-4,5,6,7-tetrahydro-6-(propylamino)benzothiazole . These data also demonstrate that the enantiomers behave independently of one another, in that the solubility of one enantiomer appears to be unaffected by the concentration in solution of the other. For example, the various synthesis reactions carried out using condition F all have chemical yields of about 50%, independent of the percentage of predominant diamine enantiomer of the starting material. When the volume of the organic solvent used in the synthesis reaction is increased, the chemical yield is reduced, but the chiral yield is increased. This is apparent by comparison of the reaction carried out in conditions F and G, where an 85:15 ratio of (6R):(6S) diamine produced a 2-amino-4,5,6,7-tetrahydro-6-(propylamino)benzothiazole product having an 86.8% chiral purity for the (6R) enantiomer when the reaction used 10 volumes of the organic solvent and a 99.8% chiral purity for the (6R) enantiomer when the reaction used 1.8 volumes of the organic solvent. Note also that the chemical yield was reduced in the reaction using a larger volume of organic solvent (43% yield in condition F and 36% yield in condition G).

In Table 3, condition H is the same as condition F, except that the recovery step does not incorporate dilution in MTBE. The MTBE is observed to increase 2-amino-4,5,6,7-tetrahydro-6-(propylamino)benzothiazole recovery (yield) from the synthesis reaction, but may reduce the overall chiral purity. This is born out by a comparison of the results for trials carried out in an 85:15 ratio of (6R):(6S) diamine, which produced a 2-amino-4,5,6,7-tetrahydro-6-(propylamino)benzothiazole product having a 86.8% chiral purity for the (6R) enantiomer when the reaction included the MTBE organic solvent and a 99.9% chiral purity for the (6R) enantiomer when the reaction did not include the MTBE organic solvent. The chemical yield was reduced by exclusion of the MTBE dilution in the recovery step; a 43% yield in condition C as opposed to a 39% yield in condition E.

Example 12

Conversion of (6R)-4,5,6,7-tetrahydro-N6-propyl-2,6-benzothiazole-diamine p-TSA Salt to (6R)-4,5,6,7-tetrahydro-N6-propyl-2,6-benzothiazole-diamine dihydrochloride (6R)-4,5,6,7-tetrahydro-N6-propyl-2,6-benzothiazole-diamine p-TSA salt (50 grams; 0.13 mol) was taken into 150 ml absolute ethanol and cooled to between 0 and 5° C. with continuous stirring. Concentrated HCl (33 ml) was slowly added to the reaction while maintaining the temperature at between 0 and 5° C., and the mixture was stirred for an additional 15 minutes. MTBE (200 ml) was added to the mixture, and stirring was continued for an additional 1.5 hours at temperature. The reaction mixture was then filtered, washed twice with an MTBE/ethanol solution (2:1, 2×50 ml wash volumes), and dried under vacuum at 30° C. overnight. The final product was 34 grams of (6R)-4,5,6,7-tetrahydro-N6-propyl-2,6-benzothiazole-diamine dihydrochloride, indicative of 92% yield, and a 97.3% chemical purity as determined by HPLC.

Example 13

Conversion of (6R)-4,5,6,7-tetrahydro-N6-propyl-2,6-benzothiazole-diamine p-TSA Salt to (6R)-4,5,6,7-tetrahydro-N6-propyl-2,6-benzothiazole-diamine dihydrochloride (6R)-4,5,6,7-tetrahydro-N6-propyl-2,6-benzothiazole-diamine p-TSA salt. (10 grams; 0.026 mol) was dissolved in 200 ml IPAC and cooled to 15° C. with continuous stirring. HCl gas was bubbled into the slurry for 1 hour. The mixture was then filtered, washed with IPAC, and dried overnight under vacuum at room temperature. The final product was 6.8 grams of (6R)-4,5,6,7-tetrahydro-N6-propyl-2,6-benzothiazole-diamine dihydrochloride, indicative of 92% yield, and a 97% chemical purity as determined by HPLC.

Example 14

Conversion of (6R)-4,5,6,7-tetrahydro-N6-propyl-2,6-benzothiazole-diamine p-TSA Salt to (6R)-4,5,6,7-tetrahydro-N6-propyl-2,6-benzothiazole-diamine Free Base (6R)-4,5,6,7-tetrahydro-N6-propyl-2,6-benzothiawle-diamine p-TSA salt (25 grams; 0.065 mol) was dissolved in 200 ml DCM and mixed into a slurry. 10 ml of water was added and the mixture was basified with 12 ml of 6N NaOH to a pH of 11-12. The two phases were split, and the aqueous was extracted with 200 ml of DCM. The combined organic phases were dried over $MgSO_4$, filtered over Celite® and concentrated. The residue was dissolved in 100 ml MTBE and slurried for several hours. The solids were then filtered, washed with MTBE and dried under vacuum at 35° C. The final product was 9.1 grams of (6R)-4,5,6,7-tetrahydro-N6-propyl-2,6-benzothiazole-diamine free base, indicative a of 66% yield, and a 98% chemical purity as determined by HPLC.

Example 15

Conversion of (6R)-4,5,6,7-tetrahydro-N6-propyl-2,6-benzothiazole-diamine p-TSA Salt to (6R)-4,5,6,7-tetrahydro-N6-propyl-2,6-benzothiazole-diamine Free Base Freebase formation was performed on a 200 gram scale. A 5 L, three necked, round-bottomed flask, equipped with an over head stirrer, thermometer, and addition funnel was charged with 200 g (0.522 mol) of (6R)-4,5,6,7-tetrahydro-N6-propyl-2,6-benzothiazole-diamine p-TSA salt and 1 L of water. The mixture was stirred and cooled to 10° C. The slurry was basified to a pH of about 11-12 by the slow addition of 200 ml of 6 N NaOH over a period of 15 min. The reaction mixture was diluted with 500 ml of brine (sodium chloride dissolved in water) and extracted with 3×1 L of dichloromethane. The combined organic phases were washed with 1.0 L of brine, dried over MgSO$_4$, filtered and concentrated to dryness. The residue was triturated with 1 L of 1:1 IPAC:Heptane, the resulting slurry was stirred for 1 hour, filtered and the filter cake was washed with 2×250 ml of 1:1 mixture of IPAC:Heptane. The filter cake was collected and dried at 40° C. under high vacuum for 24 hours to give 94.1 grams (6R)-4,5,6,7-tetrahydro-N6-propyl-2,6-benzothiazole-diamine (85.5%) as a white solid. The chemical purity was 100% AUC as tested by HPLC, and the chiral purity was 100% AUC as tested by HPLC. $^1$H NMR and $^{13}$C NMR was used to confirm the structure:$^1$H NMR (300 MHz, DMSO-δ6) δ 6.6 (s, 2H), 2.8 (m, 2H), 2.5 (m, 2H, merged with DMSO peak), 2.2 (m, 1H), 1.9 (m, 1H), 1.5-1.3 (m, 4H), 0.85 (t, 3H); $^{13}$C NMR (300 MHz, DMSO-d6) δ 166.2, 144.8, 113.6, 54.2, 49.1, 30.0, 29.6, 25.2, 23.5, 12.3.

Example 16

Conversion of (6R)-4,5,6,7-tetrahydro-N6-propyl-2,6-benzothiazole-diamine free Base to (6R)-4,5,6,7-tetrahydro-N6-propyl-2,6-benzothiazole-diamine dihydrochloride The freebase of (6R)-4,5,6,7-tetrahydro-N6-propyl-2,6-benzothiazole-diamine (4.8 grams; 0.022 mol) was dissolved in 200 ml of IPAC and cooled to 15° C. HCl gas was bubbled into the slurry for 1 hour. The mixture was then filtered, washed with IPAC and dried under vacuum at room temperature overnight. The final product was 6.4 grams of (6R)-4,5,6,7-tetrahydro-N6-propyl-2,6-benzothiazole-diamine dihydrochloride, indicative of 100% yield, and a 97% chemical purity as determined by HPLC.

Example 17

Conversion of (6R)-4,5,6,7-tetrahydro-N6-propyl-2,6-benzothiazole-diamine free Base to (6R)-4,5,6,7-tetrahydro-N6-propyl-2,6-benzothiazole-diamine dihydrochloride The freebase of (6R)-4,5,6,7-tetrahydro-N6-propyl-2,6-benzothiazole-diamine (50 grams; 0.13 mol) was dissolved in 500 ml of IPAC. Under continuous stirring, the mixture was slowly charged with 78 ml of concentrated HCl at a temperature of 25° C. The mixture was stirred overnight at ambient conditions (~25° C.), filtered and dried under vacuum at 40° C. The final product was 68 grams of (6R)-4,5,6,7-tetrahydro-N6-propyl-2,6-benzothiazole-diamine dihydrochloride, indicative of 95% yield.

Example 18

Optical Purification of (6R)-4,5,6,7-tetrahydro-N6-propyl-2,6-benzothiazole-diamine using achiral acid addition 2-amino-4,5,6,7-tetrahydro-6-(propylamino)benzothiazole entantioenriched for the (6R) enantiomer (~300 mg) was dissolved in 10 ml of the chosen solvent at 75° C. Complete dissolution was observed in all samples. Acid addition was made at 1.05 molar equivalents for the p-TSA (solvent is ethanol; 2.97 ml of 0.5 M acid) and MSA (solvent is acetonitrile; 1.49 ml of 1.0 M acid), and 2.05 molar equivalents for the fumaric (solvent is acetonitrile; 5.84 ml of 0.5 M acid) and phosphoric (solvent is acetonitrile; 2.90 ml of 1.0 M acid). The reaction mixtures were cooled to room temperature at a rate of 25° C./hour and stirred at room temperature for an additional 19 hours.

Figure 3A:
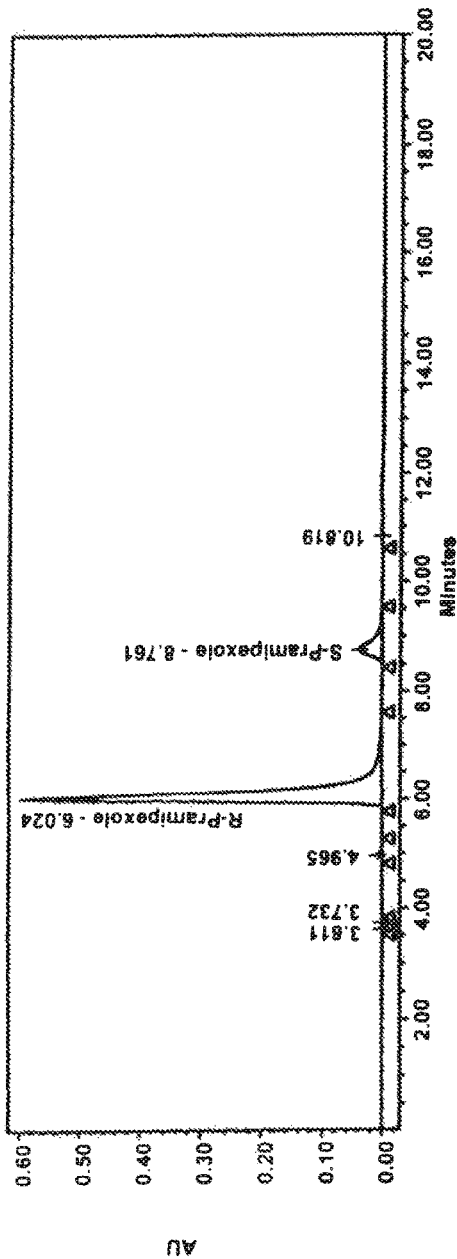
FIG. 3A shows an exemplary HPLC trace of a mixture of (6R) and (6S)-4,5,6,7-tetrahydro-N6-propyl-2,6-benzothiazole-diarnine that is entantiomerically enriched for (6R)-4,5,6,7-tetrahydro-N6-propyl-2,6-benzothiazole-diamine and a corresponding data table.
Figure 3B:
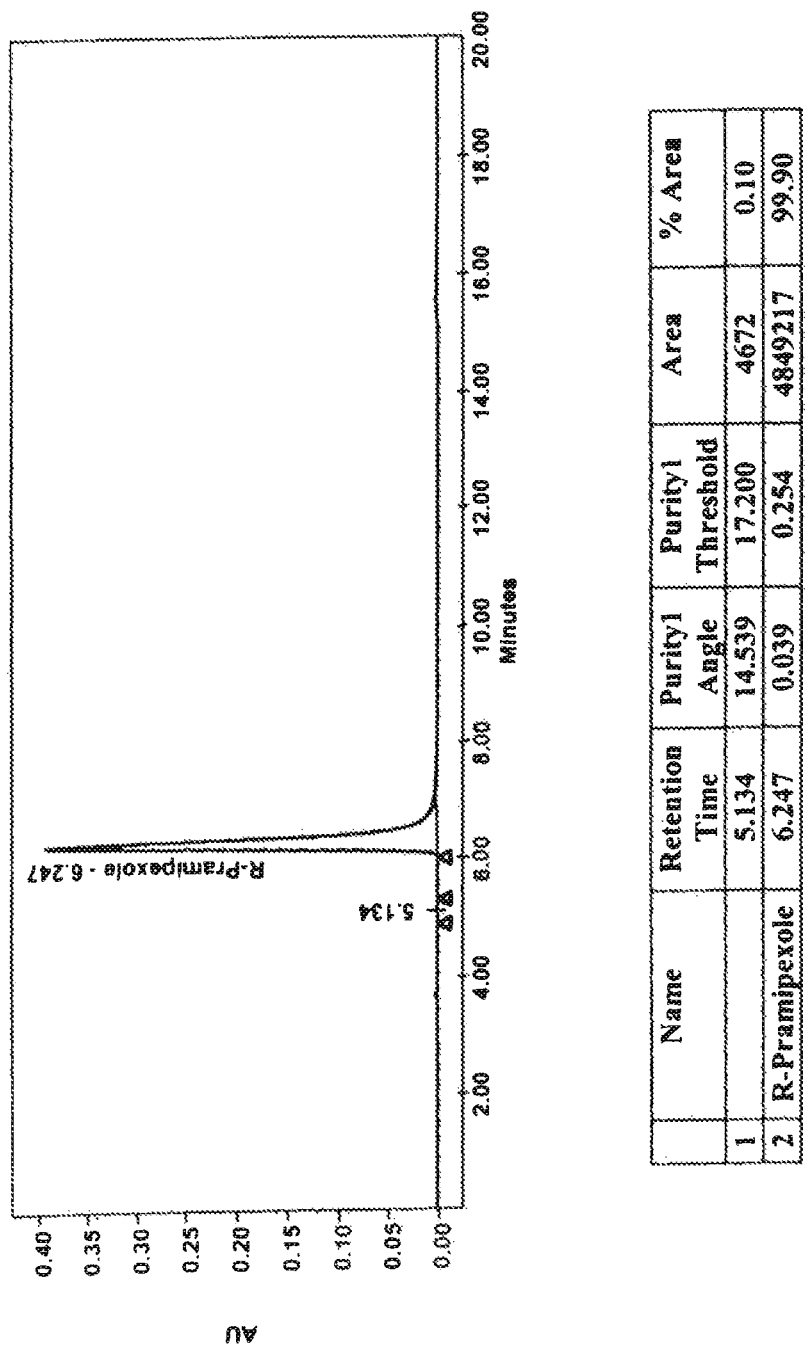
FIG. 3B shows an exemplary HPLC trace of chirally purified (6R)-4,5,6,7-tetrahydro-N6-propyl-2,6-benzothiazole-diamine and a corresponding data table.
Figure 4A:
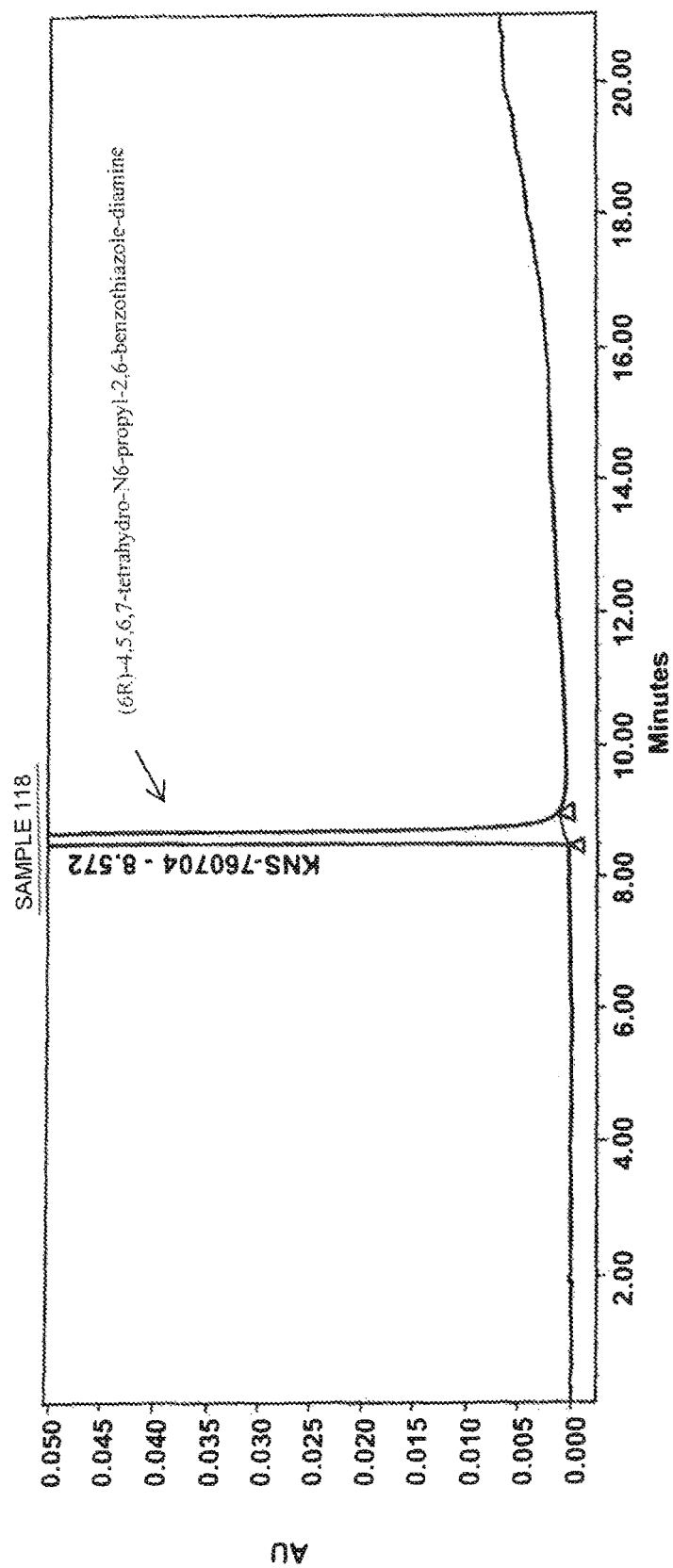
FIG. 4A shows an exemplary HPLC trace of Sample 118.

The products of purification processes were then analyzed by HPLC for chemical and chiral purity. FIG. 3A shows an exemplary HPLC trace starting material. In FIG. 4A, a large (6R)-4,5,6,7-tetrahydro-N6-propyl-2,6-benzothiazole-diamine peak can be observed at about 6 minutes and a much smaller (6S)-4,5,6,7-tetrahydro-N6-propyl-2,6-benzothiazole-diamine peak can be seen at about 9 minutes. The area of these peaks provides an estimated composition for the mixture which is shown in the table below the trace, and shows the mixture as containing about 90.2% (6R) and 8.8% (6S)-4,5,6,7-tetrahydro-N6-propyl-2,6-benzothiazole-diamine. FIG. 3B shows an exemplary trace of the 2-amino-4,5,6,7-tetrahydro-6-(propylamino)benzothiazole product following purification. In FIG. 3B, a large (6R)2-amino-4,5,6,7-tetrahydro-6-(propylamino)benzothiazole peak is observed at about 6 minutes, and no (6S)2-amino-4,5,6,7-tetrahydro-6-(propylamino)benzothiazole peak is observed. It is additionally of note that several other minor peaks are also reduced or eliminated in the product trace, and the table below the trace indicates that (6R)-4,5,6,7-tetrahydro-N6-propyl-2,6-benzothiazole-diamine makes up 99.9% of the product solution which is within the limits of analytical detectability. Results for each exemplary reaction are provided in Table 3:

TABLE 3

Experiments for preparation of the (6R)-4,5,6,7-tetrahydro-N6-propyl-2,6-benzothiazole-diamine

| Salt/Acid | Solvent | Batch Size | Results |
|---|---|---|---|
| p-TSA | ethanol | 298.7 mg | Yield = 489.5 mg (90.3%) Start Chiral Purity = 91% AUC (6R) by HPLC Final Chiral Purity = 100% AUC by HPLC |
| MSA | acetonitrile | 300.0 mg | Yield = 431.8 mg (98.9%) Start Chiral Purity = 91% AUC (6R) by HPLC Final Chiral Purity = 99.23% AUC by HPLC |
| fumaric (hot ethanol) | acetonitrile | 301.0 mg | Yield = 532 mg (84.2%) Start Chiral Purity = 91% AUC (6R) by HPLC Final Chiral Purity = 99.26% AUC by HPLC |
| phosphoric | acetonitrile | 299.4 mg | Yield = 592 mg (~100%) Start Chiral Purity = 91% AUC (6R) by HPLC Final Chiral Purity = 100% AUC by HPLC |

The solids obtained by this trituration step were isolated by filtration and dried under high vacuum at room temperature. These products were analyzed by HPLC, NMR, thermal gravimetric analysis, differential scanning calorimetry, X-ray powder diffraction (XPRD), Fourier transform infrared spectroscopy and moister-sorption analysis. The XPRD patterns showed that the p-TSA, MSA and fumarate salt forms of the (6R)-4,5,6,7-tetrahydro-N6-propyl-2,6-benzothiazole-diamine were crystalline, while the phosphate salt form of the (6R)-4,5,6,7-tetrahydro-N6-propyl-2,6-benzothiazole-diamine was amorphous.

Example 19

Industrial Scale Resolution of Racemic Diamine

A 72 L, unjacketed reactor was charged with racemic 2,6 diamino-4,5,6,7-tetrahydro-benzothiazole (4.5 kg; 26.6 mol) and 58.5 L water, and heated as a suspension to a temperature of about 60° C. to 65° C. Resolution of the enantiomers was achieved by addition of one equivalent of (D)-(-)-Tartaric acid (3991 grams; 26.6 mol) in 4.5 L of water, after which the resulting solution was heated to a temperature of about 70° C. to 75° C. and maintained at this temperature for about 1 hour. The mixture was allowed to cool to a temperature of about 20° C. to 25° C. and stirred for an additional 15 hours, after which the mixture was filtered and the solids were washed 3× with water (6.3 L each wash).

The wet solids, which contain the (6R) enantiomer of the diamine, were charged to the reactor followed by 54 L of water, and the mixture was heated to a temperature of about 70° C. to 75° C. for 2 hours. The mixture was allowed to cool to a temperature of about 20° C. to 25° C. and stirred for 17 hours. The mixture was then filtered and the solids were washed 2× with water (4.5 L each wash). The wet solids were transferred to a jacketed reactor and the reactor was charged with 8.1 L of water. The mixture was cooled to a temperature of about 0° C. to 5° C. and cautiously charged with concentrated 1.6 L of HCl, followed by 1.2 L of 50% NaOH to achieve a pH of about 9-10. During the addition, the temperature was maintained at about 0° C. to 5° C., and stirred for an additional hour at temperature. The resulting mixture was then filtered and the solids were washed 2× with cold (0° C. to 5° C.) water (1.1 L each wash). The solids were transferred to a jacketed reactor and were reslurried once more with 4.5 L of water at 0° C. to 5° C. The solids were filtered and dried under warm air (40° C. to 45° C.) to give 1940 grams of the product ((6R) diamine) as a white solid, with an 86% yield for the (6R) enantiomer.

The mother liquors of the initial resolution step, which contain the (6S) enantiomer of the diamine, were concentrated to afford diamine with a 95.5% yield for the (6S) enantiomer. Results of reactions performed using 1000, 4500 and 41.00 grams of starting material are provided in Table 4

TABLE 4

Experiments for industrial scale resolution of the (6R) enantiomer of diamine

| Input (grams) | Yield (%) of (6R) enantiomer | Chemical Purity (AUC % by HPLC) | Chiral Purity (AUC % by HPLC) |
| --- | --- | --- | --- |
| 1000 | 76 | >99 | 98.3 |
| 4500 | 86 | >99 | 98.5 |
| 4100 | 54 | >99 | 98.5 |

Example 20

Industrial Scale Preparation of Propyl Tosylate

A 100 L glass, jacketed reactor was charged with 1-propanol (2.098 kg; 34.9 mol), triethylamine (4.585 kg; 45.3 mol; 1.3 equivalents) and DCM (20.1 L). The mixture was cooled to a temperature of about 5° C. to 15° C. and cautiously charged with a solution of p-toluenesulfonyl chloride (6 kg; 31.47 mol; 0.9 equivalents) in DCM (10.5 L) over 30 minutes. Once the addition was complete, the mixture was warmed to a temperature of about 18° C. to 22° C. and stirred for 12 hours. The reaction mixture was assayed by $^1$H NMR (in $CDCl_3$) and deemed complete. HCl (6 N; 2.98 L) was cautiously charged while maintaining the temperature below 25° C. The aqueous phase was removed, and the organic phase was washed 2× with water (21 L each wash), dried with $MgSO_4$, and filtered over Celite®. The filtered solids were then washed with DCM (4 L) and concentrated to a residue. The residue was dissolved in heptane and concentrated again to afford a final propyl tosylate product (6.385 kg, 95% yield).

Example 21

Industrial Scale Preparation of (6R)-4,5,6,7-tetrahydro-N6-propyl-2,6-benzothiazole-diamine p-TSA Salt: Condition C A 72 liter unjacketed reactor was charged with 1.84 kg (10.87 mol) of (6R)-2,6 diamino-4,5,6,7-tetrahydro-benzothiazole ((6R) diamine), followed by 14.7 L of dimethyl formamide (DMF). Under continuous stirring, the mixture was heated to a temperature of between 65° C. and 68° C. A solution of 2926 grams propyl tosylate and 1761 grams diisopropylethyleamine in 3.5 L DMF was added slowly over a period of 2 hours. The reaction was continued at 67° C. for an additional 4 hours, after which the solution was gradually cooled to room temperature (18° C. to 22° C.) and stirred for an additional 15 hours. The solution was diluted with 14.7 L of MTBE over a time period of 30 minutes, and stirred for an additional 1 hour. The precipitated material was collected by filtration and washed with 7.3 L MTBE, followed by 3 washes of 3.7 L each of ethanol, and a wash with 9.2 L heptane. The washed precipitated cake was dried under high vacuum at 30° C. to 35° C. The final weight of the dried product was 2090 grams, representing a 50% yield.

Example 22

Purity of (6R)-4,5,6,7-tetrahydro-N6-propyl-2,6-benzothiazole-diamine

The Limit of Quantitation (LOQ) to 0.05% precision was determined from six replicate preparations of (6R)-4,5,6,7-tetrahydro-N6-propyl-2,6-benzothiazole-diamine. The RSD was measured to be 6.3% and the S/N (signal to noise ratio) was measured to be 61:1. The pre-defined acceptance criteria at LOQ was to have a S/N≥10:1 and for the RSD to be ≤20.0%. These results exceeded the acceptance criteria by a wide margin.

Signal-to-noise levels can vary for numerous reasons, including pump behavior, air in lines, extent of mobile phase degassing, system-to-system variations and electronic fluctuations. The LOD had previously been estimated to be 0.03% based upon the 0.1% preparation which produced a S/N of 30:1. Although the recent 0.05% levels produced a S/N of 61:1, based upon the overall history of the method, the estimated LOD will remain at the stated 0.03%.

Linearity was determined over the range 0.05%-150% of nominal (0.2 µg/mL-600 µg/mL). The correlation coefficient over this expanded range was determined to be 0.9999. This exceeded the pre-defined linearity acceptance criterion of ≥0.995.

The weight percent assay is on an as-is basis versus the current standard which has a purity of 94.0%. Each sample was prepared in duplicate with single injections. Purity data is provided in the Table 5:

TABLE 5

(6R)-4,5,6,7-tetrahydro-N6-propyl-2,6-benzothiazole-diamine Purity Data

| Sample | % area | ave | % wt/wt | ave |
|---|---|---|---|---|
| Sample 118 | 100.0 | | 95.1 | |
| Sample 118 | 100.0 | 100.0 | 95.0 | 95.1 |
| Sample 105 | 100.0 | | 94.7 | |
| Sample 105 | 100.0 | 100.0 | 94.7 | 94.7 |
| Sample 061 | 100.0 | | 94.5 | |
| Sample 061 | 100.0 | 100.0 | 94.6 | 94.5 |
| Sample 326A | 100.0 | | 95.0 | |
| Sample 326A | 100.0 | 100.0 | 94.7 | 94.8 |

Figure 4B:
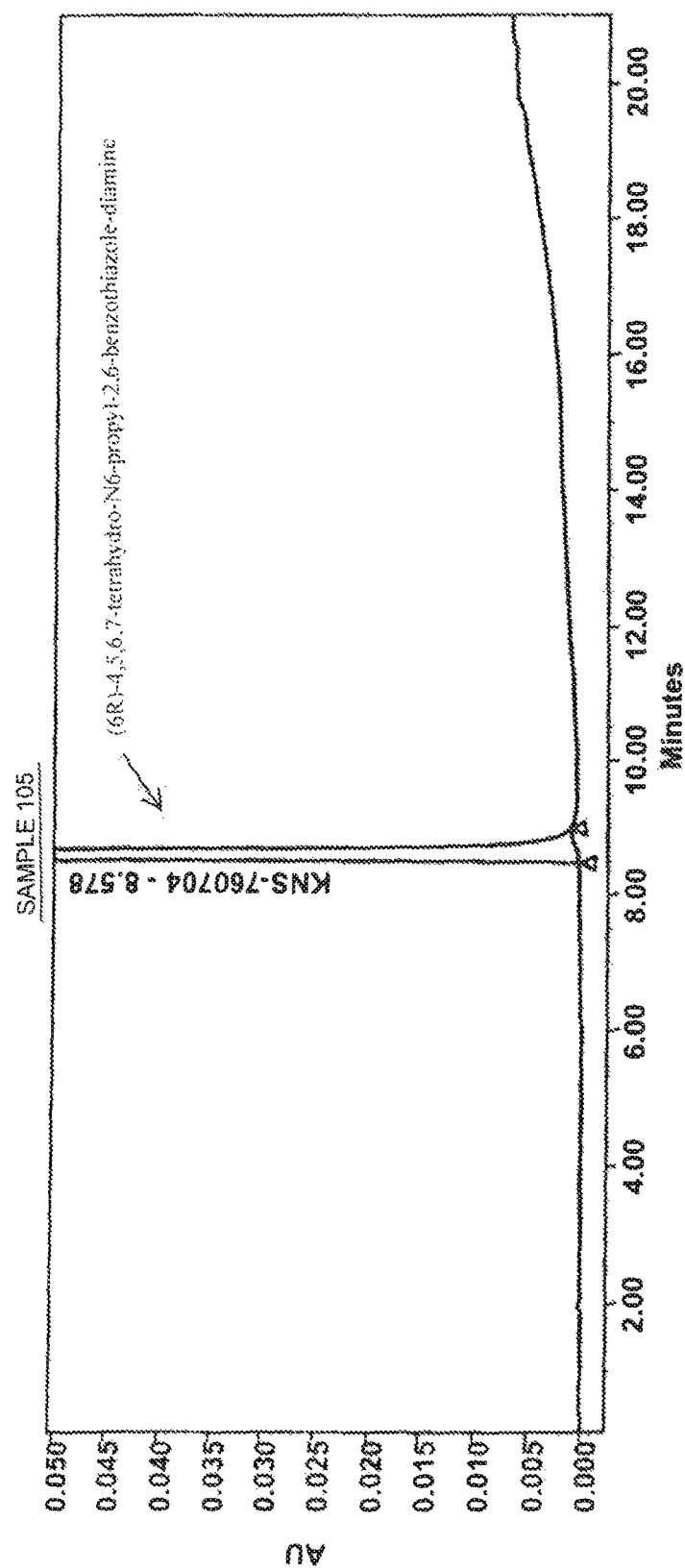
FIG. 4B shows an exemplary HPLC trace of Sample 105.
Figure 4C:
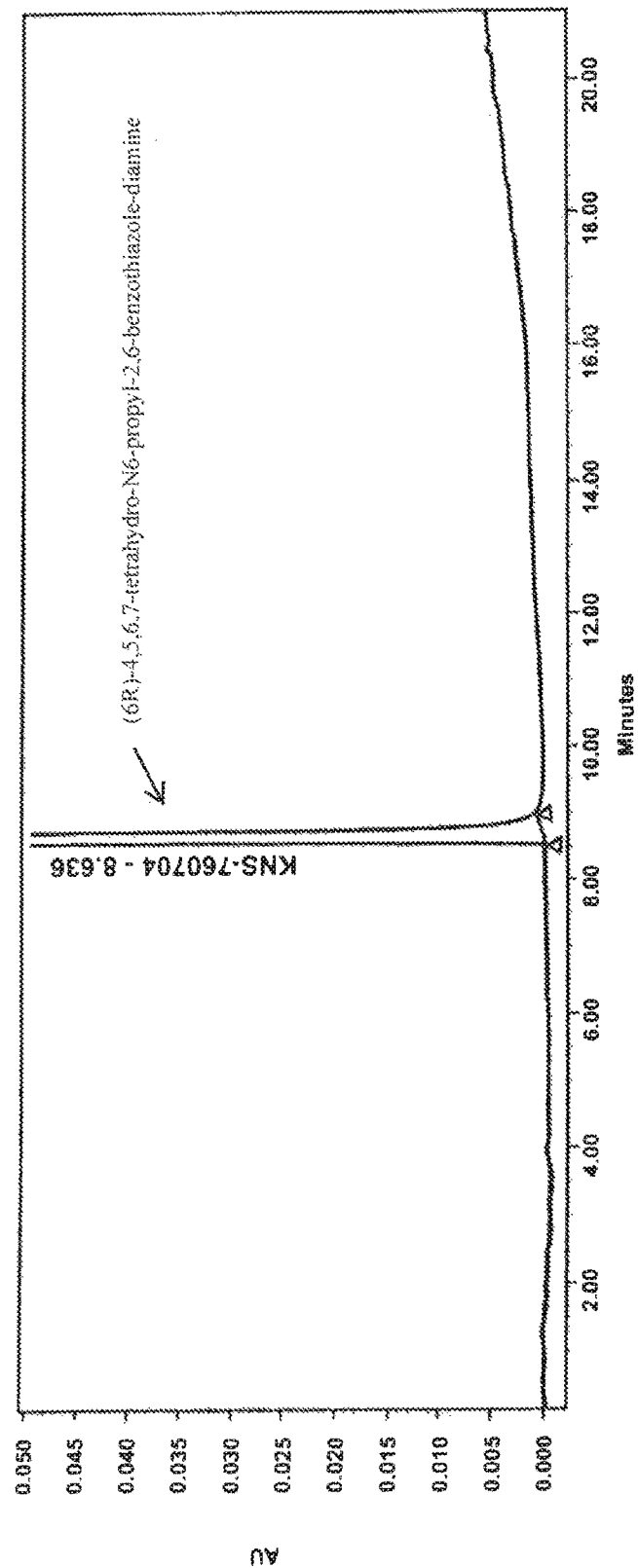
FIG. 4C shows an exemplary HPLC trace of Sample 061.
Figure 4D:
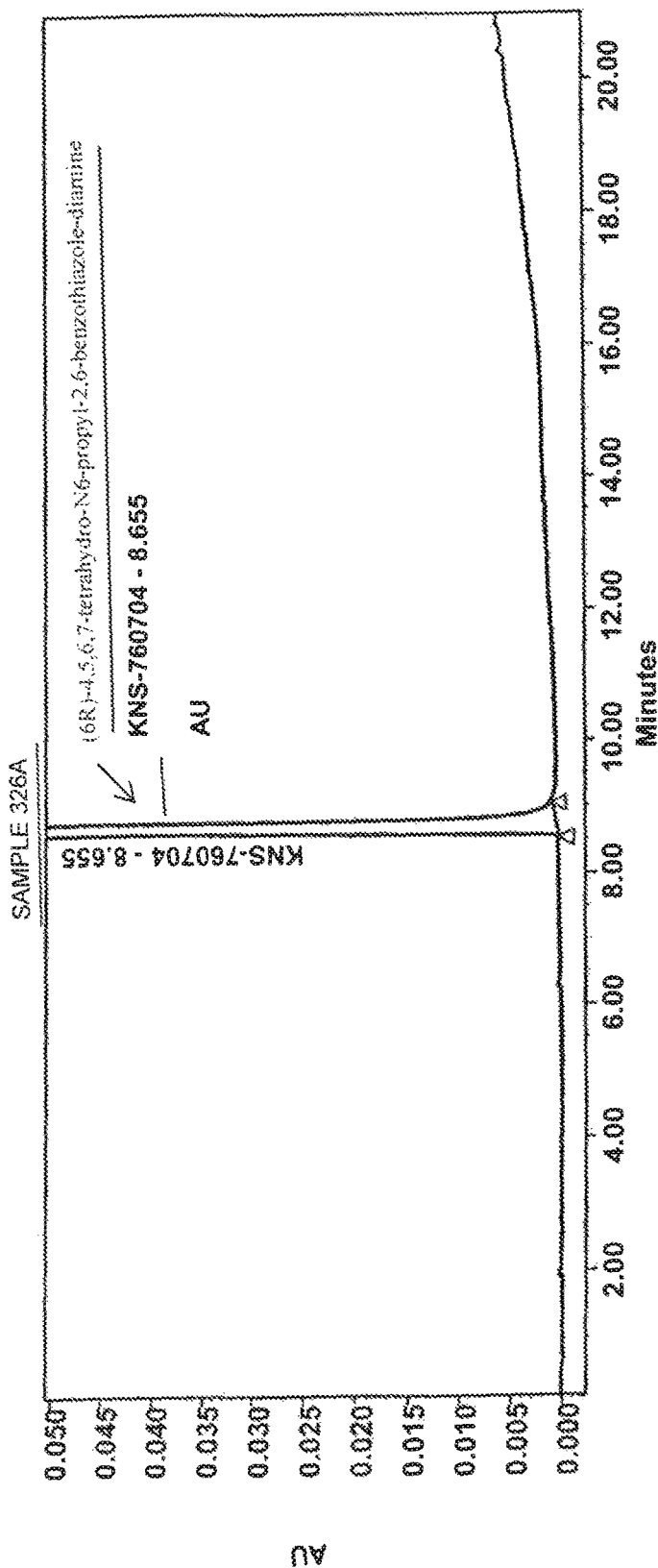
FIG. 4D show an exemplary HPLC trace of Sample 326A.

Example chromatographs are provided in FIG. 4A-D. Specifically, FIG. 4A is an HPLC Chromatograph of Sample 118; FIG. 4B is an HPLC Chromatograph of Sample 105; FIG. 4C is an HPLC Chromatograph of Sample 061; and FIG. 4 D is an HPLC Chromatograph of Sample 326A. These data show preparation of (6R)-4,5,6,7-tetrahydro-N6-propyl-2,6-benzothiazole-diamine at 100% purity.

Example 23

Propyl tosylate Concentration of (6R)-4,5,6,7-tetrahydro-N6-propyl-2,6-benzothiazole-diamine A solid phase extraction (SPE) procedure was developed to remove the high levels of (6R)-4,5,6,7-tetrahydro-N6-propyl-2,6-benzothiazole-diamine prior to analysis while maintaining recovery of propyl tosylate spiked at 1.5 ppm. The SPE cartridges (Supelco Discovery DSC-18, 6 mL, 1 g) are pre-activated and washed with 6 mL acetonitrile (MeCN) followed by 6 mL of water. Five milliliters of 100 mg/mL solutions of KNS-760704 prepared in 5:95, MeCN/water with 0.5% phosphoric acid are then introduced into the SPE cartridges. The acid sufficiently maintains the polarity of the (6R)-4,5,6,7-tetrahydro-N6-propyl-2,6-benzothiazole-diamine so that it can be readily washed from the SPE cartridge with an additional 5 mL of 5:95, MeCN/water with 0.5% phosphoric acid while retaining any propyl tosylate. Any propyl tosyate is then eluted from the SPE cartridges using 5 mL of 95:5 MeCN/water. Fortunately, due to the sensitivity gained from method development experiments, no further sample enrichment is needed and the samples are analyzed as-is. The samples are compared to a standard of 1.5 ppm (0.15 μg/mL) propyl tosylate prepared in 95:5 MeCN/water.

Figure 5:
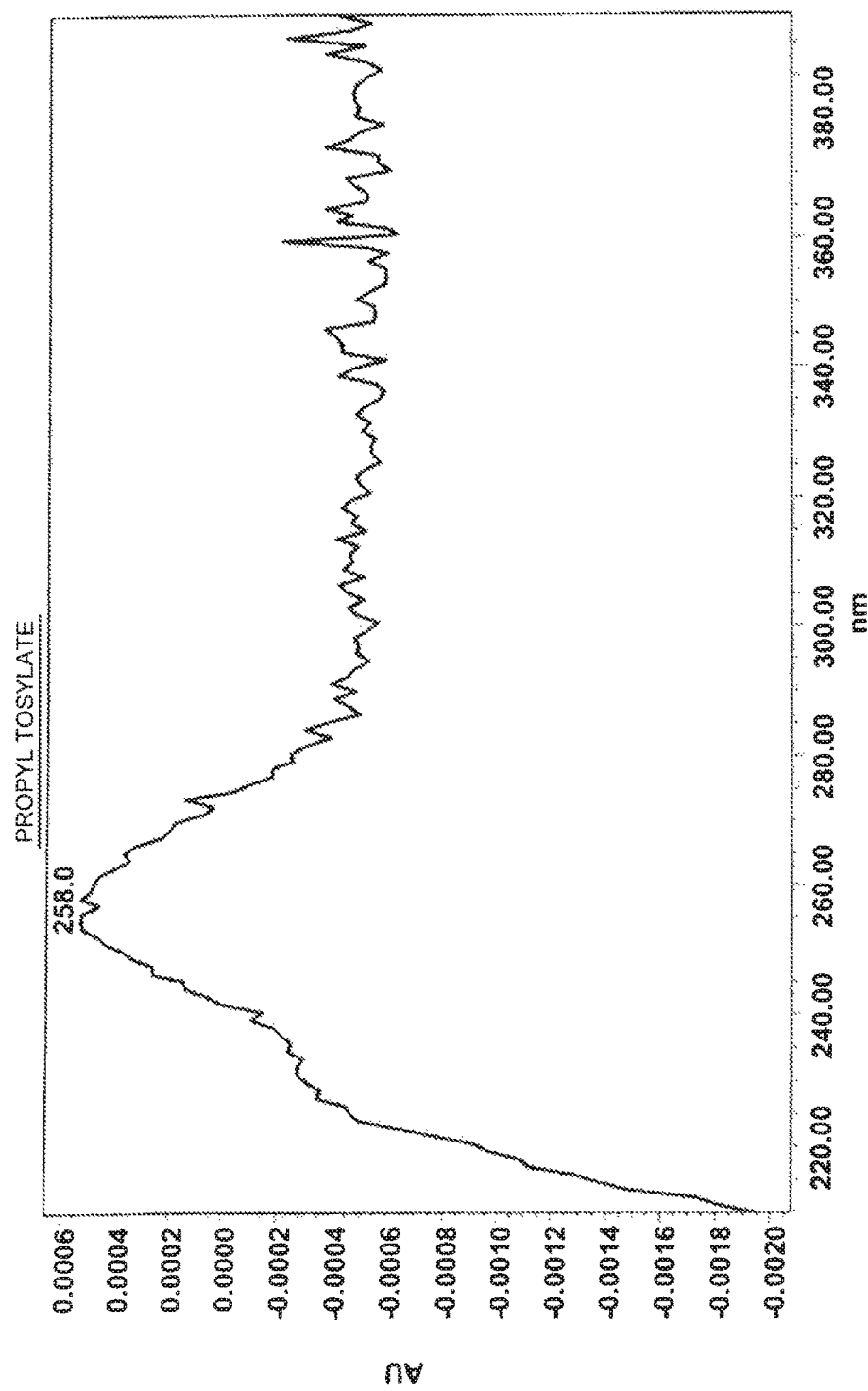
FIG. 5 shows an exemplary UV spectrum of a propyl tosylate peak eluted from an SPE column.

An examplary UV spectrum of propyl tosylate eluted from the SPE cartridges is shown in FIG. 5.

Figure 6A:
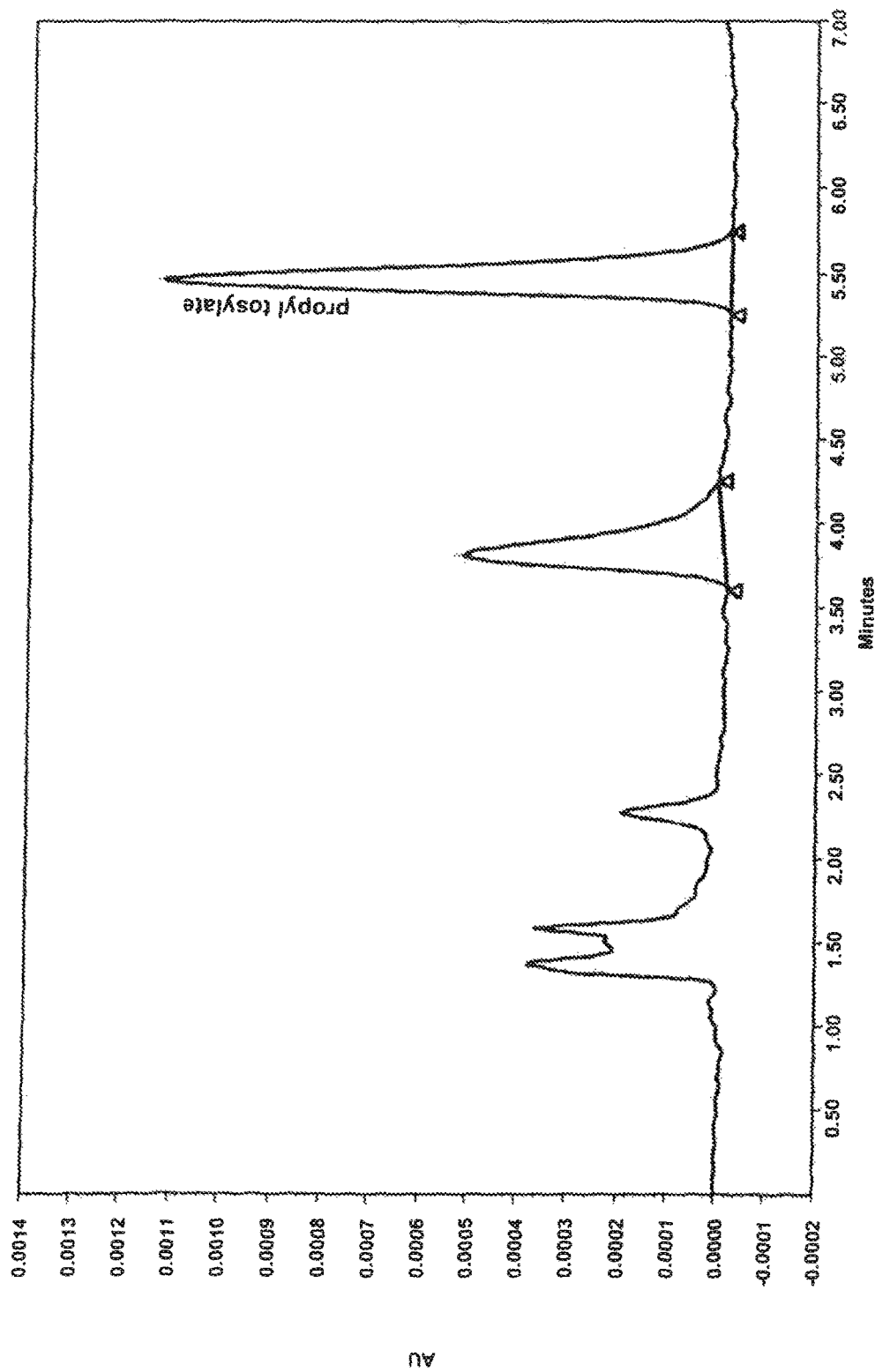
FIG. 6A shows an exemplary HPLC trace of a propyl tosylate standard.
Figure 6B:
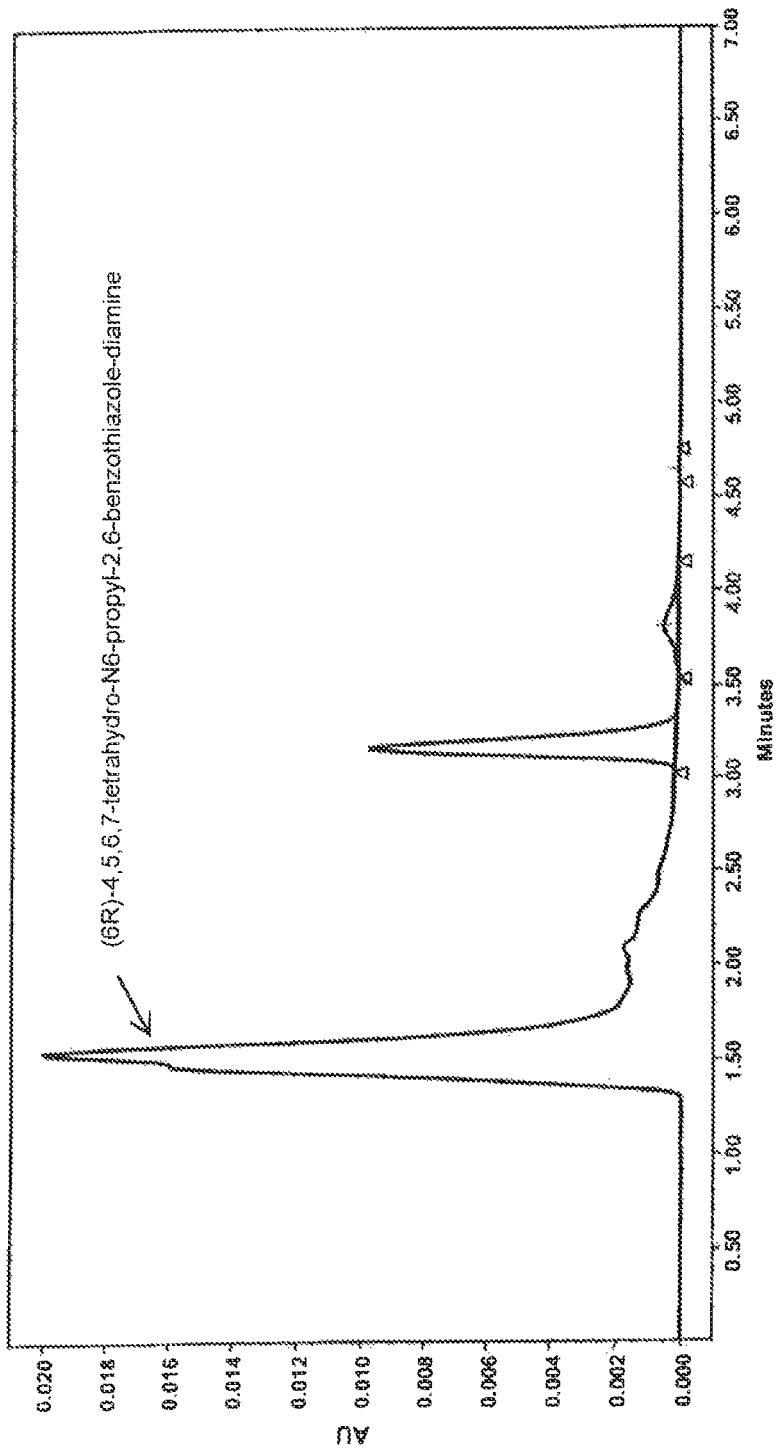
FIG. 6B shows an exemplary HPLC trace of a (6R)-4,5,6,7-tetrahydro-N6-propyl-2,6-benzothiazole-diamine sample.

Exemplary HPLC data from of the (6R)-4,5,6,7-tetrahydro-N6-propyl-2,6-benzothiazole-diamine eluted from the SPE cartridge is provided in FIGS. 6A and 6B. FIG. 6A shows an HPLC chromatograph of a propyl tosylate standard prepared from 100 mg of propyl tosylate. FIG. 6B shows an HPLC chromatograph of a 1 g sample of (6R)-4,5,6,7-tetrahydro-N6-propyl-2,6-benzothiazole-diamine prepared by the method of embodiments of the invention. No propyl tosylate is evident based on the data provided in FIG. 6B as indicated by the absence of a peak corresponding to propyl tosylate (right).

Example 24

Chiral Purity of (6S)-4, 5,6,7-tetrahydro-N6-propyl-2,6-benzothiazole-diamine

Figure 7A:
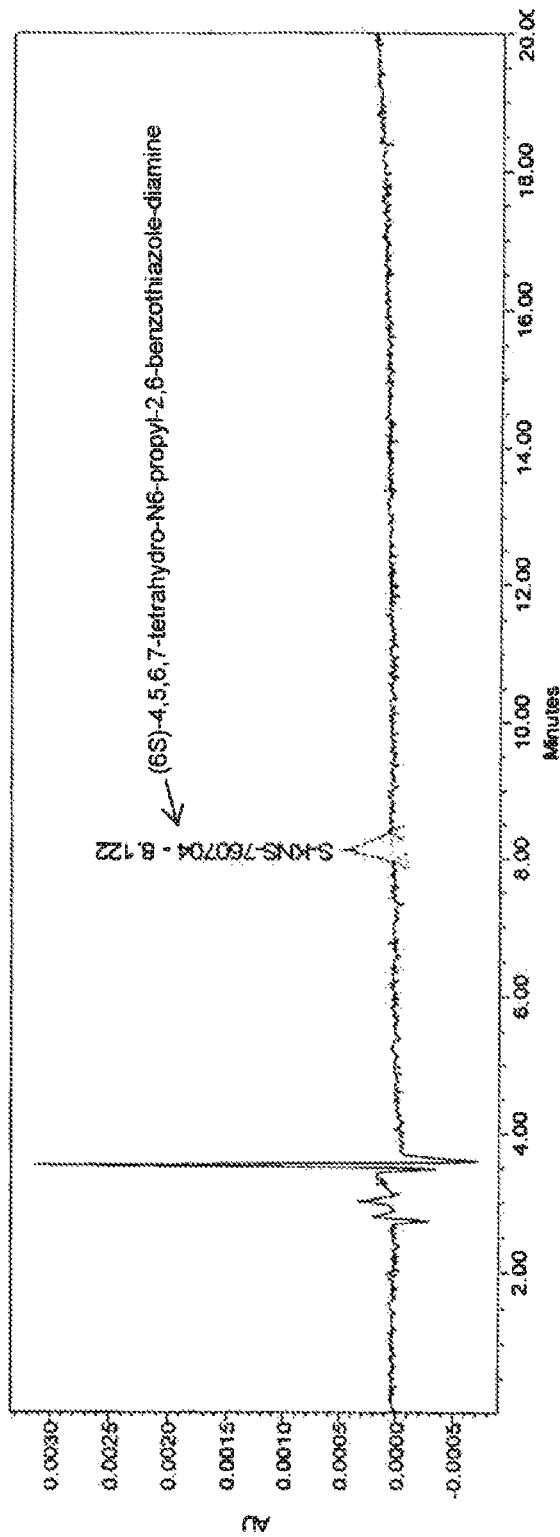
FIG. 7A shows an exemplary HPLC trace of a standard (6S)-4,5,6,7-tetrahydro-N6-propyl-2,6-benzothiazole-diamine.
Figure 7B:
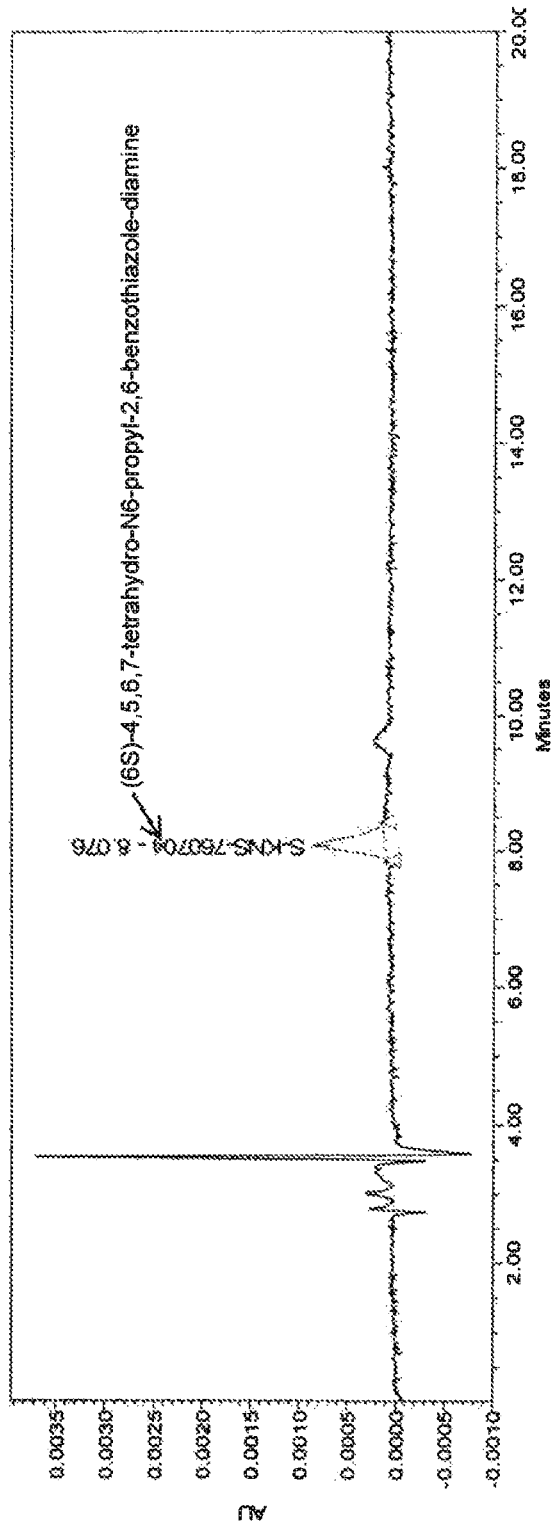
FIG. 7B shows an exemplary HPLC trace of a sample (6S)-4,5,6,7-tetrahydro-N6-propyl-2,6-benzothiazole-diamine.

The chirality of the (6S)-4,5,6,7-tetrahydro-N6-propyl-2,6-benzothiazole-diamine prepared as described above was tested using a Chiralpak IA column under HPLC conditions. About 25 mg of (6S)-4,5,6,7-tetrahydro-N6-propyl-2,6-benzothiazole-diamine were applied to the column. Exemplary HPLC traces of a (6S)-4,5,6,7-tetrahydro-N6-propyl-2,6-benzothiazole-diamine standard are provided in FIG. 7A and an HPLC trace of a sample (6S)-4,5,6,7-tetrahydro-N6-propyl-2,6-benzothiazole-diamine is provided in FIG. 7B. Test data is provided in Table 6.

TABLE 6

% Recovery of (6S)-4,5,6,7-tetrahydro-N6-propyl-2,6-benzothiazole-diamine

| Level | Preparation | % Recovery |
|---|---|---|
| 100% | 1 | 91.13 |
| | 2 | 91.18 |
| | 3 | 97.61 |
| | Average | 93.3 |
| | % RSD | 4.0 |

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A process for preparing a chirally purified substituted 4,5,6,7,-tetrahydro-benzothaizole diamine dihydrochloride comprising:
   a. heating a solution to a temperature of from about 65° C. to about 125° C., the solution comprising enantiomerically enriched 4,5,6,7-tetrahydro-benzothiazole diamine of formula (1):

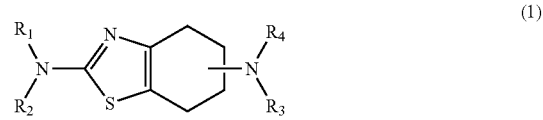

wherein:
   $R_1$ is a hydrogen atom, an alkyl group having 1 to 6 carbon atoms, an alkenyl or alkynyl group having 3 to 6 carbon atoms, an alkanoyl group having 1 to 6 carbon atoms, a phenyl alkyl or phenyl alkanoyl group having 1 to 3 carbon atoms in the alkyl part;
   $R_2$ is a hydrogen atom or an alkyl group having 1 to 4 carbon atoms;
   $R_3$ is a hydrogen atom, an alkyl group having 1 to 7 carbon atoms, a cycloalkyl group having 3 to 7 carbon atoms, an alkenyl or alkynyl group having 3 to 6 carbon atoms, an alkanoyl group having 2 to 7 carbon atoms, a phenyl alkyl or phenyl alkanoyl group having 1 to 3 carbon atoms in the alkyl part;
   $R_4$ is a hydrogen atom, an alkyl group having 1 to 4 carbon atoms, an alkenyl or alkynyl group having 3 to 6 carbon atoms; and at least one or $R_1$, $R_2$, $R_3$ or $R_4$ is a hydrogen in an organic solvent; and a propyl sulfonate or a propyl halide in a solvent to form a reaction mixture;

b. reacting the reaction mixture at a temperature of from about 65° C. to about 125° C.;

c. recovering a chirally purified substituted 4,5,6,7-tetrahydro-benzothiazole diamine or salt thereof and d. converting the chirally purified substituted 4,5,6,7-tetrahydro-benzothiazole diamine to the chirally purified substituted 4,5,6,7-tetrahydro-benzothiazole diamine dichloride salt.

2. The process of claim 1, wherein the steps of heating in step a., and reacting in step b., are carried out from about 65° C. to about 100° C.

3. The process of claim 1, wherein the steps of heating in step a., and reacting in step b., are carried out from about 65° C. to about 95° C.

4. The process of claim 1, wherein the propyl halide selected from an n-propyl bromide, n-propyl chloride, n-propyl iodide, and combinations thereof.

5. The process of claim 4, wherein the propyl chloride is n-propyl chloride.

6. The process of claim 1, wherein the propyl sulfonate is n-propyl tosylate.

7. The process of claim 1, wherein the chirally purified substituted 4,5,6,7-tetrahydro-benzothiazole diamine is at least greater than about 90% chirally pure.

8. The process of claim 1, wherein the chirally purified substituted 4,5,6,7-tetrahydro-benzothiazole diamine is at least greater than about 99% chirally pure.

9. The process of claim 1, wherein the chirally purified substituted 4,5,6,7-tetrahydro-benzothiazole diamine is at least about 99.9% chirally pure.

10. The process of claim 1, wherein the chemical purity of the substituted 4,5,6,7-tetrahydro-benzothiazole diamine is greater than about 98%.

11. The process of claim 1, wherein the chemical purity of the substituted 4,5,6,7-tetrahydro-benzothiazole diamine is greater than about 99%.

12. The process of claim 1, wherein the chemical purity of the substituted 4,5,6,7-tetrahydro-benzothiazole diamine is 97%.

13. The process of claim 1, wherein the enantiomerically enriched 4,5,6,7-tetrahydro-benzothiazole diamine is enantiomerically enriched for an R-enantiomer and chirally purified substituted 4,5,6,7-tetrahydro-benzothiazole diamine is chirally purified for an R-enantiomer.

14. The process of claim 1, wherein the enantiomerically enriched 4,5,6,7-tetrahydro-benzothiazole diamine is enantiomerically enriched for (6R)-2,6 diamino-4,5,6,7-tetrahydro-benzothiazole and the chirally purified substituted 4,5,6,7-tetrahydro-benzothiazole diamine is (6R)-4,5,6,7-tetrahydro-N6-propyl-2,6-benzothiazole-diamine.

15. The process of claim 1, wherein the enantiomerically enriched 4,5,6,7-tetrahydro-benzothiazole diamine is enantiomerically enriched for an S-enantiomer and the chirally purified substituted 4,5,6,7-tetrahydro-benzothiazole diamine is chirally purified for an S-enantiomer.

16. The process of claim 1, wherein the enantiomerically enriched 4,5,6,7-tetrahydro-benzothiazole diamine is enantiomerically enriched for (6S)-2,6 diamino-4,5,6,7-tetrahydro-benzothiazole and the chirally purified substituted 4,5,6,7-tetrahydro-benzothiazole diamine is (6S)-4,5,6,7-tetrahydro-N6-propyl-2,6-benzothiazole-diamine.

17. The process of claim 1, wherein the enantiomerically enriched 4,5,6,7-tetrahydro-benzothiazole diamine comprises a ratio of greater than about 1:4 R-enantiomer to S-enantiomer to about 4:1 R-enantiomer to S-enantiomer.

18. The process of claim 1, wherein the solvent is selected from an organic solvent and an organic solvent mixed with water.

19. The process of claim 1, wherein steps a., b., and each further comprise stirring.

20. The process of claim 1, wherein step c. comprises one or more steps selected from filtering the reaction mixture to isolate a precipitate, washing a precipitate, and drying a precipitate.

21. The process of claim 1, wherein the solution of step a. comprises enantiomerically enriched 4,5,6,7-tetrahydro-benzothiazole diamine of formula (1) and a propyl halide and the chirally purified substituted 4,5,6,7-tetrahydro-benzothiazole diamine of step c. is a chirally purified substituted 4,5,6,7-tetrahydro-benzothiazole diamine monohydrochloride salt.

22. The process of claim 1, wherein the solution of step a. comprises enantiomerically enriched 4,5,6,7-tetrahydro-benzothiazole diamine of formula (1) and a propyl sulfonate and the chirally purified substituted 4,5,6,7-tetrahydro-benzothiazole diamine of step c. is a chirally purified substituted 4,5,6,7-tetrahydro-benzothiazole diamine sulfonic acid salt.

23. The process of claim 1, wherein step d comprises i) dissolving the 4,5,6,7-tetrahydro-benzothiazole diamine or salt thereof of step c. in a solvent; ii) adding hydrochloric acid and iii) isolating the 4,5,6,7,-tetrahydro-benzothaizole diamine dihydrochloride.

24. The process of claim 23 wherein the 4,5,6,7-tetrahydro-benzothiazole diamine or salt thereof of step c. is the 4,5,6,7-tetrahydro-benzothiazole diamine sulfonic acid salt and step i) comprises i-a) dissolving the 4,5,6,7-tetrahydro-benzothiazole diamine sulfonic acid salt in a solvent selected from dichloromethane/water or water i-b)adding NaOH to increase the pH, i-c) isolating the 4,5,6,7-tetrahydro-benzothiazole diamine, and i-d) dissolving the 4,5,6,7-tetrahydro-benzothiazole diamine in a solvent.

25. The process of claim 20, wherein steps a. and b. further comprise stirring.

26. The process of claim 20 wherein step c. comprises one or more steps selected from filtering the reaction mixture to isolate a precipitate, washing a precipitate, and drying a precipitate.

27. A process for preparing a chirally purified (6R)-4,5,6,7,-tetrahydro-N6-propyl-2,6-benzothiazole-diamine dihydrochloride comprising:

a. heating a solution to a temperature of from about 65° C. to about 125° C., the solution comprising entantiomerically enriched (6R)2,6 diamino-4,5,6,7-tetrahydro-benzothiazole in an organic solvent; and an n-propyl halide in a solvent to form a reaction mixture;

b. reacting the reaction mixture at a temperature of from about 65° C. to about 125° C.;

c. recovering a chirally purified substituted (6R)-4,5,6,7,-tetrahydro-N6-propyl-2,6-benzothiazole-diamine monohydrochloride salt, and d. converting the chirally purified substituted (6R)-4,5,6,7,-tetrahydro-N6-propyl-2,6-benzothiazole-diamine monohydrochloride salt to the chirally purified (6R)-4,5,6,7,-tetrahydro-N6-propyl-2,6-benzothiazole-diamine dihydrochloride.

28. The process of claim 23, wherein the steps of heating in step a., and reacting in step b., are carried out from about 65° C. to about 100° C.

29. The process of claim 23, wherein the steps of heating in step a., and reacting in step b., are carried out from about 65° C. to about 95° C.

30. The process of claim 23, wherein the n-propyl halide is n-propyl chloride.

31. The process of claim 23, wherein the solvent is selected from an organic solvent and an organic solvent mixed with water.

32. The process of claim 23, wherein steps a., b., and each further comprise stirring.

33. The process of claim 23, wherein step c. comprises one or more steps selected from filtering the reaction mixture to isolate a precipitate, washing a precipitate, and drying a precipitate.

34. The process of claim 23, wherein step d comprises i) dissolving the (6R)-4,5,6,7,-tetrahydro-N6-propyl-2,6-benzothiazole-diamine or salt thereof of step c. in a solvent; ii) adding hydrochloric acid and iii) isolating the (6R)-4,5,6,7,-tetrahydro-N6-propyl-2,6-benzothiazole-diamine dihydrochloride.

35. The process of claim 30, wherein steps a. and b further comprise stirring.

36. The process of claim 30 wherein step c. comprises one or more steps selected from filtering the reaction mixture to isolate a precipitate, washing a precipitate, and drying a precipitate.

\* \* \* \* \*

UNITED STATES PATENT AND TRADEMARK OFFICE
CERTIFICATE OF CORRECTION

PATENT NO. : 10,179,774 B2  
APPLICATION NO. : 15/369230  
DATED : January 15, 2019  
INVENTOR(S) : Raje et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 74 days.

Signed and Sealed this  
Twenty-seventh Day of August, 2019

Andrei Iancu  
*Director of the United States Patent and Trademark Office*